(12) United States Patent
Pei et al.

(10) Patent No.: US 7,205,409 B2
(45) Date of Patent: Apr. 17, 2007

(54) PHARMACEUTICAL COMPOSITIONS AS INHIBITORS OF DIPEPTIDYL PEPTIDASE-IV (DPP-IV)

(75) Inventors: Zhonghua Pei, Libertyville, IL (US); Xiaofeng Li, Gurnee, IL (US); Kenton L. Longenecker, Grayslake, IL (US); Hing L. Sham, Vernon Hills, IL (US); Paul E. Wiedeman, Deerfield, IL (US)

(73) Assignee: Abbott Laboratories, Abbott Park, IL (US)

( * ) Notice: Subject to any disclaimer, the term of this patent is extended or adjusted under 35 U.S.C. 154(b) by 207 days.

(21) Appl. No.: 10/935,053

(22) Filed: Sep. 7, 2004

(65) Prior Publication Data

US 2005/0131019 A1    Jun. 16, 2005

Related U.S. Application Data

(60) Provisional application No. 60/500,079, filed on Sep. 4, 2003.

(51) Int. Cl.
*C07D 215/38* (2006.01)
*C07D 295/00* (2006.01)

(52) U.S. Cl. .................. 546/153; 546/268.1; 548/518

(58) Field of Classification Search ................ 514/312, 514/343, 422; 546/153, 268.1; 548/518
See application file for complete search history.

(56) References Cited

U.S. PATENT DOCUMENTS

| | | | |
|---|---|---|---|
| 6,011,155 | A | 1/2000 | Villhauer |
| 6,110,949 | A | 8/2000 | Villhauer |
| 6,124,305 | A | 9/2000 | Villhauer |
| 6,395,767 | B2 | 5/2002 | Robl et al. |

FOREIGN PATENT DOCUMENTS

| | | |
|---|---|---|
| WO | 9515309 | 6/1995 |
| WO | 9819998 | 5/1998 |
| WO | 0134594 | 5/2001 |
| WO | 0140180 | 6/2001 |
| WO | 0168603 | 9/2001 |
| WO | 0196295 | 12/2001 |
| WO | 0214271 | 2/2002 |
| WO | 0230890 | 4/2002 |
| WO | 0304468 | 1/2003 |
| WO | 0416587 | 2/2004 |
| WO | 0426822 | 4/2004 |

OTHER PUBLICATIONS

Villhauer et al., "1-[[(3-Hydroxy-1-adamantyl)amino]acetyl]-2-cyano-(S)-pyrrolidine: a potent, selective, and orally bioavailable dipeptidyl peptidase IV inhibitor with antihyperglycemic properties," Journal of Medicinal Chemistry 46(13):2774-2789 (2003).
Ashworth et al., "2-cyanopyrrolidides as potent, stable inhibitors of dipeptidyl peptidase IV," Bioorganic & Medicinal Chemistry Letters 6(10):1163-1166 (1996).

*Primary Examiner*—D. Margaret Seaman
(74) *Attorney, Agent, or Firm*—Andrew Parial; Johana Corbin

(57) ABSTRACT

The present invention relates to compounds of formula (I),

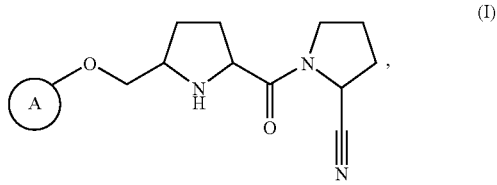

which inhibit dipeptidyl peptidase IV (DPP-IV) and are useful for the prevention or treatment of diabetes, especially type II diabetes, as well as hyperglycemia, syndrome X, hyperinsulinemia, β-cell failure, obesity, satiety disorders, atherosclerosis, and various immunomodulatory diseases.

25 Claims, No Drawings

PHARMACEUTICAL COMPOSITIONS AS INHIBITORS OF DIPEPTIDYL PEPTIDASE-IV (DPP-IV)

CROSS-REFERENCE SECTION TO RELATED APPLICATIONS

This application claims the benefit of priority of U.S. Provisional Application No. 60/500,079, which was filed on Sep. 4, 2003, which is incorporated by reference in its entirety.

FIELD OF THE INVENTION

The present invention relates to compounds which inhibit dipeptidyl peptidase IV (DPP-IV) and are useful for the prevention or treatment of diabetes, especially type II diabetes, as well as hyperglycemia, syndrome X, hyperinsulinemia, β-cell failure, obesity, satiety disorders, atherosclerosis, and various immunomodulatory diseases.

BACKGROUND OF THE INVENTION

Dipeptidyl peptidase IV (DPP-IV, CD26, EC 3.4.14.5) is a serine protease with specificity for cleaving Xaa-Pro and, to a lesser extent, Xaa-Ala dipeptides from the N-termini of polypeptides and proteins. DPP-IV is a non-classical serine protease in that the catalytic triad of Ser-Asp-His, found in the C-terminal region of the enzyme, is in reverse order to that found in classical serine proteases. DPP-IV is widely expressed in mammalian tissue as a type II integral membrane protein. DPP-IV is expressed on the surface of differentiated epithelial cells of the intestine, liver, kidney proximal tubules, prostate, corpus luteum, and on leukocyte subsets such as lymphocytes and macrophages. A soluble form of the enzyme is found in serum that has structure and function identical to the membrane-bound form of the enzyme but lacks the hydrophobic transmembrane domain.

DPP-IV has many physiologically relevant substrates such as chemokines, RANTES (regulated on activation normal T cell expressed and secreted), eotaxin, and macrophage-derived chemokine, neuropeptides such as NPY (neuropeptide Y) and substance P, vasoactive peptides, and incretins such as GLP-1 (glucagon-like peptide-1) and GIP (gastric inhibitory peptide/glucose-dependent insulinotropic polypeptide). GLP-1 is a 30 amino acid peptide hormone produced in the L cells of the distal small intestine in response to ingested nutrients. GLP-1 binding to its receptor on various tissues stimulates insulin gene expression, biosynthesis and glucose-dependent insulin secretion, inhibits glucagon secretion, promotes satiety, slows gastric emptying and promotes growth of pancreatic beta cells. Based on this profile, GLP-1-based therapies are expected to be beneficial in the treatment of type II diabetes and obesity. Studies in which type II diabetic patients have been infused with GLP-1 have demonstrated efficacy in normalizing both fasted and prandial glycemia. However, active GLP-1 (7-36) amide is rapidly converted by DPP-IV to GLP-1 (9-36), which is inactive or is a receptor antagonist. The short half-life of GLP-1 in the circulation (1–1.5 minutes) is a major obstacle to its use as a therapeutic agent. To circumvent the drawback of the short half-life of GLP-1, inhibitors of DPP-IV, the primary degradative enzyme of GLP-1, increase the level of active circulating GLP-1 (7-36) amide. DPP-IV inhibitors have been demonstrated to improve glucose tolerance in type II diabetes.

For a DPP-IV inhibitor to be optimally useful in a human therapeutic setting, it should ideally be delivered as a once-daily oral dose. To accomplish this goal, the compound in question must exhibit both potent inhibition of the enzyme and a desirable pharmacokinetic profile. Because DPP-IV plays a critical role in controlling the degradation of GLP-1, and because the enzyme is ubiquitously expressed at high levels in a variety of tissues as well as within the vasculature, only a potent inhibitor will be capable of impacting circulating GLP-1 levels in a therapeutically relevant manner. In vivo studies suggest that continuous inhibition of DPP-IV leads to a maximal increase in circulating GLP-1, and thus to the greatest improvement in overall glucose control. These results suggest that an inhibitor with a long half-life is most therapeutically desirable.

Several issues complicate the task of preparing a DPP-IV inhibitor that is both highly potent and has an in vivo half-life consistent with once-daily dosing. Many potent inhibitors contain a 2-cyanopyrrolidide functionality in the P1 (catalytic binding site) position. The cyano group of the 2-cyanopyrrolidide forms a covalent linkage with the enzyme through the catalytic Serine that confers increased potency to the inhibitors that contain it by slowing the release of inhibitor.

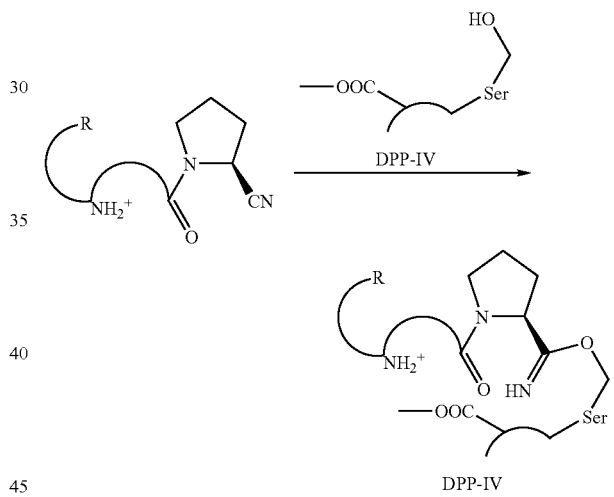

But the 2-cyanopyrrolidide moiety has liabilities as well. In particular, the cyano-group is found in close proximity to a P2-amine functionality that serves as a marker for the substrate amino-terminus in the DPP-IV inhibitory pharmacophore. When these two groups are held in such proximity, they tend to react to form a cyclic amidine, destroying the pharmacophore. Thus, cyanopyrrolidide-containing DPP-IV inhibitors tend to have limited chemical stability, which is reflected in poor pharmacokinetic profiles.

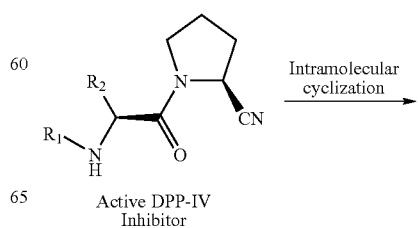

Active DPP-IV Inhibitor

-continued

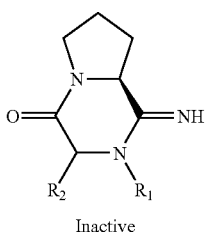

Inactive

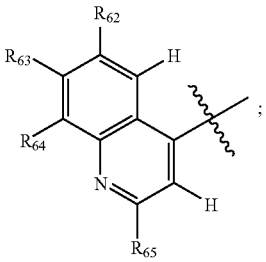

Compounds of the instant invention are both highly potent and chemically stable, and thus provide unique therapeutic benefit and an improved dosing profile for the treatment of human diseases.

SUMMARY OF THE INVENTION

The present invention is directed to compounds of formula (I),

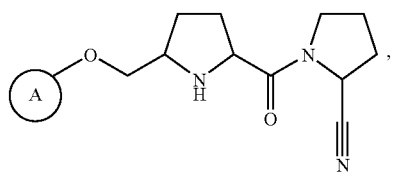

or a therapeutically acceptable salt or prodrug thereof, wherein

A is selected from the group consisting of

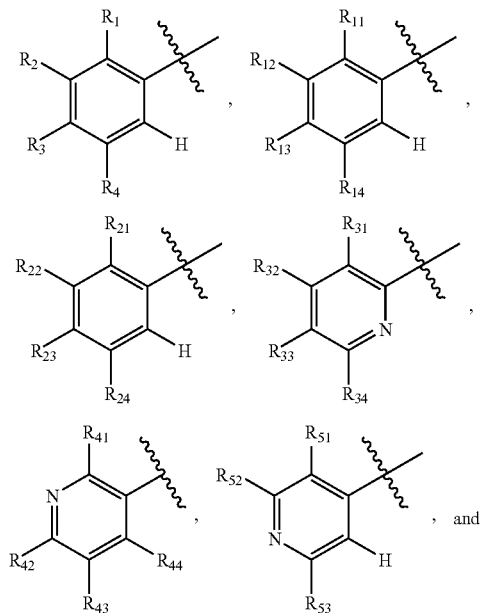

or therapeutically suitable salt, ester or prodrug, thereof, wherein $R_1$ is selected from the group consisting of halo, haloalkyl, haloalkoxy, haloalkylthio, $R_aR_bN-$, $R_aR_bN$carbonyl, $R_aR_bN$carbonylalkyl, $R_aR_bN$sulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, carboxyalkoxy, alkylcarbonyl, alkylsulfonyl, aryl, heteroaryl, heterocycle, cycloalkyl, arylalkyl, heteroarylalkyl, heterocyclealkyl, hydroxyalkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_2$ is selected from the group consisting of hydrogen, halo, haloalkyl, haloalkoxy, haloalkylthio, $R_aR_bN-$, $R_aR_bN$carbonyl, $R_aR_bN$carbonylalkyl, $R_aR_bN$sulfonyl, alkoxy, alkoxyalkoxy, alkoxyalkyl, alkoxycarbonyl, cyano, cyanoalkyl, hydroxy, hycoxyalkyl, alkyl, alkenyl, alkynyl, alkylthio, carboxy, carboxyalkyl, carboxyalkoxy, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

or $R_1$ and $R_2$, together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, naphthalene, furan, imidazole, isothiazole, isoxazole, 1,3-dioxolane, 1,2,3-oxadiazole, 1,2,5-oxadiazole, oxazole, pyrazine, pyrazole, pyridazine, pyrimidine, pyrrole, thiazole, thiophene, triazine, 1,2,3-triazole or unsubstituted pyridine;

$R_3$ is selected from the group consisting of hydrogen, halo, haloalkyl, haloalkoxy, haloalkylthio, $R_aR_bN-$, $R_aR_bN$carbonyl, $R_aR_bN$carbonylalkyl, $R_aR_bN$sulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_4$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, alkoxy cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

with the proviso that if $R_1$ and $R_2$ and the carbon atoms to which they are attached form a benzene ring, then $R_4$ is not carboxylic acid;

$R_a$ and $R_b$ are independently selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl;

$R_{11}$ is selected from the group consisting of halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{12}$ and $R_{13}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole;

$R_{14}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{21}$ is selected from the group consisting of halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{22}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{23}$ and $R_{24}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, naphthalene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole;

$R_{31}$ is selected from the group consisting of halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{32}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{33}$ is selected from the group consisting of hydrogen, halo, haloalkyl, haloalkoxy, haloalkylthio, $R_aR_bN—$, $R_aR_bNcarbonyl$, $R_aR_bNcarbonylalkyl$, $R_aR_bNsulfonyl$, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{34}$ is selected from the group consisting of hydrogen, halo, haloalkyl, haloalkoxy, haloalkylthio, $R_aR_bN—$, $R_aR_bNcarbonyl$, $R_aR_bNcarbonylalkyl$, $R_aR_bNsulfonyl$, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{41}$ is selected from the group consisting of hydrogen, halo, haloalkyl, haloalkoxy, haloalkylthio, $R_aR_bN—$, $R_aR_bNcarbonyl$, $R_aR_bNcarbonylalkyl$, $R_aR_bNsulfonyl$, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{42}$ is selected from the group consisting of hydrogen, halo, haloalkyl, haloalkoxy, haloalkylthio, $R_aR_bN—$, $R_aR_bNcarbonyl$, $R_aR_bNcarbonylalkyl$, $R_aR_bNsulfonyl$, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{43}$ is selected from the group consisting of hydrogen, halo, haloalkyl, haloalkoxy, haloalkylthio, $R_aR_bN—$, $R_aR_bNcarbonyl$, $R_aR_bNcarbonylalkyl$, $R_aR_bNsulfonyl$, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{44}$ is selected from the group consisting of hydrogen, halo, haloalkyl, haloalkoxy, haloalkylthio, $R_aR_bN—$, $R_aR_bNcarbonyl$, $R_aR_bNcarbonylalkyl$, $R_aR_bNsulfonyl$, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{51}$ is selected from the group consisting of halo, haloalkyl, haloalkoxy, haloalkylthio, $R_aR_bN—$, $R_aR_bNcarbonyl$, $R_aR_bNcarbonylalkyl$, $R_aR_bNsulfonyl$, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{52}$ is selected from the group consisting of hydrogen, halo, haloalkyl, haloalkoxy, haloalkylthio, $R_aR_bN—$, $R_aR_bNcarbonyl$, $R_aR_bNcarbonylalkyl$, $R_aR_bNsulfonyl$, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

or $R_{51}$ and $R_{52}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole;

$R_{53}$ is selected from the group consisting of hydrogen, halo, haloalkyl, haloalkoxy, haloalkylthio, $R_aR_bN—$, $R_aR_bNcarbonyl$, $R_aR_bNcarbonylalkyl$, $R_aR_bNsulfonyl$, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{62}$, $R_{63}$, $R_{64}$ and $R_{65}$ are each independently selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl; and wherein When A is selected from the group consisting of

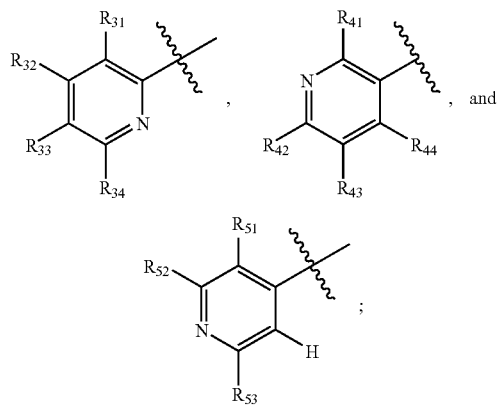

the nitrogen of the pyridine group of A may be optionally substituted with an N-oxide;

provided that exactly one of $R_{41}$ or $R_{44}$ is hydrogen.

Accordingly, the present invention is directed to methods to improve glucose tolerance in type II diabetes comprising administering a therapeutically effective amount of a compound of formula (I). According to another embodiment of the present invention, there is provided a method for treating type 2 diabetes, insulin resistance, hyperinsulinemia, impaired glucose tolerance, β-cell failure, obesity, satiety disorders, hypercholesterolemia, and hypertriglyceridemia comprising administering a therapeutically effective amount of a compound of formula (I).

According to still another embodiment, the present invention is directed to a pharmaceutical composition comprising a therapeutically effective amount of a compound of formula (I) in combination with a pharmaceutically suitable carrier.

DETAILED DESCRIPTION OF THE INVENTION

Accordingly, the principle embodiment of the present invention is directed toward a compound of formula (I),

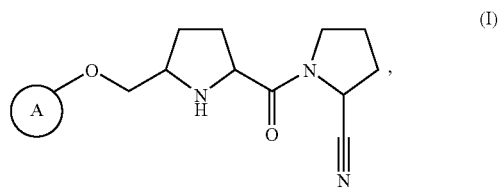

or a therapeutically acceptable salt or prodrug thereof, wherein

A is selected from the group consisting of

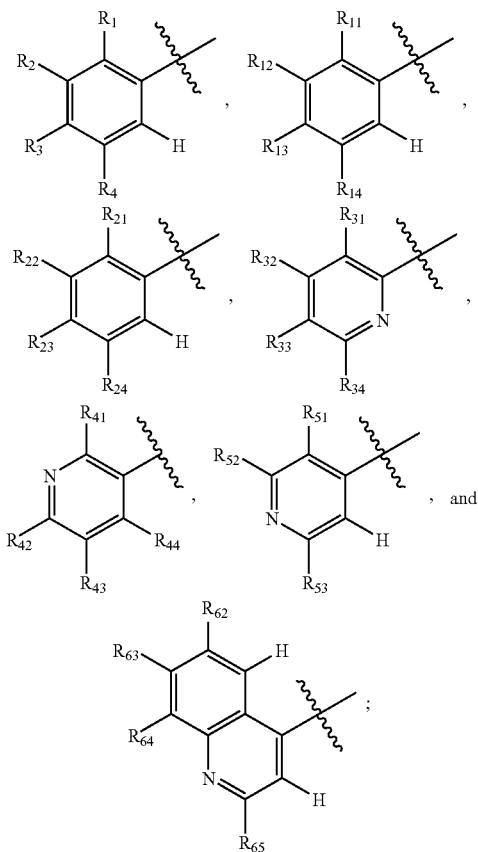

or therapeutically suitable salt, ester or prodrug, thereof, wherein $R_1$ is selected from the group consisting of halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, carboxyalkoxy, alkylcarbonyl, alkylsulfonyl, aryl, heteroaryl, heterocycle, cycloalkyl, arylalkyl, heteroarylalkyl, heterocyclealkyl, hydroxyalkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_2$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, carboxyalkyl, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

or $R_1$ and $R_2$, together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, naphthalene, furan, imidazole, isothiazole, isoxazole, 1,3-dioxolane, 1,2,3-oxadiazole, 1,2,5-oxadiazole, oxazole, pyrazine, pyrazole, pyridazine, pyrimidine, pyrrole, thiazole, thiophene, triazine, 1,2,3-triazole or unsubstituted pyridine;

$R_3$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_4$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, alkoxy cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

with the proviso that if $R_1$ and $R_2$ and the carbon atoms to which they are attached form a benzene ring, then $R_4$ is not carboxylic acid;

$R_a$ and $R_b$ are independently selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl;

$R_{11}$ is selected from the group consisting of halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrolyl, tetrazolyl, thiazolyl, thiophenyl, triazinyl and 1,2,3-triazolyl;

$R_{12}$ and $R_{13}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole;

$R_{14}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{21}$ is selected from the group consisting of halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{22}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{23}$ and $R_{24}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, naphthalene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole;

$R_{31}$ is selected from the group consisting of halo, haloalkyl, haloalkoxy, haloalkylthio, $R_aR_bN—$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{32}$ is selected from the group consisting of hydrogen, halo, haloalkyl, haloalkoxy, haloalkylthio, $R_aR_bN—$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{33}$ is selected from the group consisting of hydrogen, halo, haloalkyl, haloalkoxy, haloalkylthio, $R_aR_bN—$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{34}$ is selected from the group consisting of hydrogen, halo, haloalkyl, haloalkoxy, haloalkylthio, $R_aR_bN—$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{41}$ is selected from the group consisting of hydrogen, halo, haloalkyl, haloalkoxy, haloalkylthio, $R_aR_bN—$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{42}$ is selected from the group consisting of hydrogen, halo, haloalkyl, haloalkoxy, haloalkylthio, $R_aR_bN—$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{43}$ is selected from the group consisting of hydrogen, halo, haloalkyl, haloalkoxy, haloalkylthio, $R_aR_bN—$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{44}$ is selected from the group consisting of hydrogen, halo, haloalkyl, haloalkoxy, haloalkylthio, $R_aR_bN—$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{51}$ is selected from the group consisting of halo, haloalkyl, haloalkoxy, haloalkylthio, $R_aR_bN—$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

R_{52} is selected from the group consisting of hydrogen, halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

or $R_{51}$ and $R_{52}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole;

$R_{53}$ is selected from the group consisting of hydrogen, halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{62}$, $R_{63}$, $R_{64}$ and $R_{65}$ are each independently selected from the group consisting of hydrogen, halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl; and wherein A is selected from the group consisting of

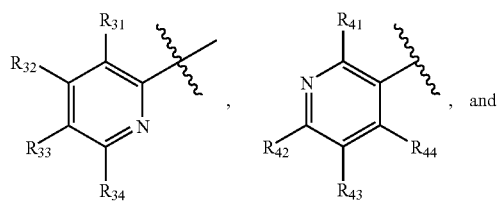, and

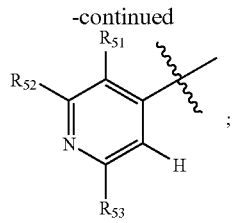;

the nitrogen of the pyridine group of A may be optionally substituted with an oxide;

provided that exactly one of $R_{41}$ or $R_{44}$ is hydrogen.

Another embodiment of the present invention discloses compounds of formula (I), or therapeutically suitable salt, ester or prodrug, thereof, wherein A is

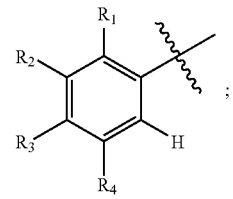;

$R_1$ is selected from the group consisting of halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, carboxyalkoxy, alkylcarbonyl, alkylsulfonyl, aryl, heteroaryl, heterocycle, cycloalkyl, arylalkyl, heteroarylalkyl, heterocyclealkyl, hydroxyalkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl; $R_2$ is selected from the group consisting of hydrogen, halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; $R_3$ is selected from the group consisting of hydrogen, halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; $R_4$ is selected from the group consisting of hydrogen, halo, haloalkyl, haloalkoxy, haloalkylthio, $R_aR_bN-$, $R_aR_bNcarbonyl$, $R_aR_bNcarbonylalkyl$, $R_aR_bNsulfonyl$, alkoxy, alkoxyalkoxy, alkoxyalkyl, alkoxycarbonyl, alkoxycyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; and $R_a$ and $R_b$ are independently selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl.

Another embodiment of the present invention discloses compounds of formula (I), or therapeutically suitable salt, ester or prodrug, thereof, wherein A is

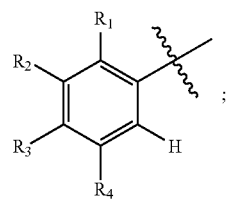

$R_1$ is selected from the group consisting of halo, haloalkyl, haloalkoxy, $R_aR_bN-$, $R_aR_bNcarbonyl$, alkoxy, alkoxycarbonyl, cyano, hydroxyalkyl, alkyl, alkenyl, carboxy, carboxyalkyl, carboxyalkoxy, alkylcarbonyl, alkylsulfonyl, aryl, heteroaryl, heterocycle, hydroxyalkyl, nitro, wherein the heteroaryls are selected from the group consisting of furanyl, imidazolyl, isothiazolyl, isoxazolyl, 1,2,3-oxadiazoyl, 1,2, oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl; $R_2$ is selected from the group consisting of hydrogen, halo, haloalkyl, haloalkoxy, $R_aR_bN-$, $R_aR_bNcarbonyl$, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyrimidinyl, pyrrolyl, tetrazolyl, thiazolyl, thiophenyl, triazinyl and 1,2,3-triazolyl; $R_3$ is selected from the group consisting of hydrogen, halo, haloalkyl, haloalkoxy, $R_aR_bN-$, $R_aR_bNcarbonyl$, $R_aR_bNcarbonylalkyl$, $R_aR_bNsulfonyl$, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; $R_4$ is selected from the group consisting of hydrogen, halo, haloalkyl, haloalkoxy, $R_aR_bN-$, $R_aR_bNcarbonyl$, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; and $R_a$ and $R_b$ are independently selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl.

Another embodiment of the present invention discloses compounds of formula (I), or therapeutically suitable salt, ester or prodrug, thereof, wherein A is

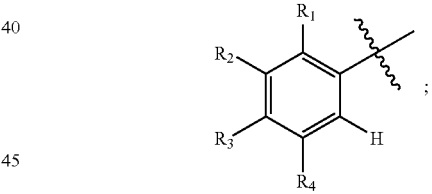

$R_1$ is selected from the group consisting of halo, alkoxy, cyano, alkyl, carboxy, carboxyalkyl, carboxyalkoxy, alkylsulfonyl, heteroaryl and hydroxyalkyl, wherein the heteroaryl is pyrazolyl; $R_2$ is selected from the group consisting of hydrogen, halo and alkylsulfonyl; $R_3$ is selected from the group consisting of hydrogen, halo, haloalkyl, $R_aR_bN-$, $R_aR_bNcarbonyl$, alkoxy, alkoxycarbonyl, cyano, carboxy, carboxyalkoxy, alkylsulfonyl, heteroaryl and heterocycle, wherein the heteroaryl is tetrazolyl; $R_4$ is selected from the group consisting of hydrogen, $R_aR_bN-$, alkoxycarbonyl, cyano, carboxy, alkylsulfonylNH and nitro; and $R_a$ and $R_b$ are independently selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl.

Another embodiment of the present invention discloses compounds of formula (I), or therapeutically suitable salt, ester or prodrug, thereof, wherein A is

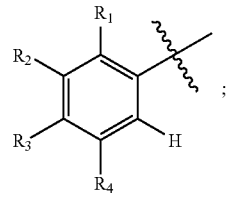

$R_1$ and $R_2$, together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, naphthalene, furan, imidazole, isothiazole, isoxazole, 1,3-dioxolane, 1,2,3-oxadiazole, 1,2,5-oxadiazole, oxazole, pyrazine, pyrazole, pyridazine, pyrimidine, pyrrole, thiazole, thiophene, triazine, 1,2,3-triazole or unsubstituted pyridine; $R_3$ is selected from the group consisting of hydrogen, halo, haloalkyl, haloalkoxy, haloalkylthio, $R_aR_bN-$, $R_aR_bN$carbonyl, $R_aR_bN$carbonylalkyl, $R_aR_bN$sulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; $R_4$ is selected from the group consisting of hydrogen, halo, haloalkyl, haloalkoxy, haloalkylthio, $R_aR_bN-$, $R_aR_bN$carbonyl, $R_aR_bN$carbonylalkyl, $R_aR_bN$sulfonyl, alkoxy, alkoxyalkoxy, alkoxyalkyl, alkoxycarbonyl, alkoxy cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2, 5oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; with the proviso that if $R_1$ and $R_2$ and the carbon atoms to which they are attached form a benzene ring, then $R_4$ is not carboxylic acid; and $R_a$ and $R_b$ are independently selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl.

Another embodiment of the present invention discloses compounds of formula (I), or therapeutically suitable salt, ester or prodrug, thereof, wherein A is

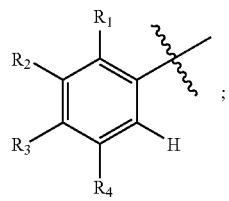

$R_1$ and $R_2$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, naphthalene, furan, imidazole, isothiazole, isoxazole, 1,3dioxolane, 1,2,3-oxadiazole, 1,2,5-oxadiazole, oxazole, pyrazine, pyrazole, pyridazine, pyrimidine, pyrrole, thiazole, thiophene, triazine, 1,2,3-triazole or unsubstituted pyridine; $R_3$ is selected from the group consisting of hydrogen, halo, haloalkyl, haloalkoxy, $R_aR_bN-$, $R_aR_bN$carbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; $R_4$ is selected from the group consisting of hydrogen, halo, haloalkyl, haloalkoxy, RAN—, $R_aR_bN$carbonyl, alkoxy, alkoxycarbonyl, alkoxy cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; with the proviso that if $R_1$ and $R_2$ and the carbon atoms to which they are attached form a benzene ring, then $R_4$ is not carboxylic acid; and $R_a$ and $R_b$ are independently selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl.

Another embodiment of the present invention discloses compounds of formula (I), or therapeutically suitable salt, ester or prodrug, thereof, wherein A is

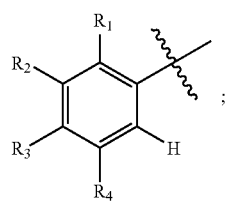

$R_1$ and $R_2$, together with the carbon atoms to which they are attached, form a substituted or unsubstituted heterocycle or a substituted or unsubstituted aryl, heteroaryl or cycloalkyl selected from the group consisting of benzene, thiophene or unsubstituted pyridine; $R_3$ is selected from the group consisting of hydrogen, halo, haloalkyl, RAN—, $R_aR_b$Ncarbonyl, alkoxy, alkoxycarbonyl, cyano, carboxy, carboxyalkoxy, alkylsulfonyl, heteroaryl, heterocycle, wherein the heteroaryl is tetrazolyl; $R_4$ is selected from the group consisting of hydrogen, $R_aR_bN$—, alkoxycarbonyl, alkoxy cyano, alkylsulfonylNH and nitro; and $R_a$ and $R_b$ are independently selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl.

Another embodiment of the present invention discloses compounds of formula (I), or therapeutically suitable salt, ester or prodrug, thereof, wherein A is

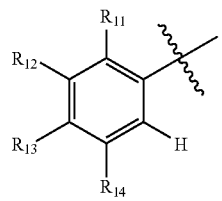

$R_{11}$ is selected from the group consisting of halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl; $R_{12}$ and $R_{13}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole; and $R_{14}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl.

Another embodiment of the present invention discloses compounds of formula (I), or therapeutically suitable salt, ester or prodrug, thereof, wherein A is

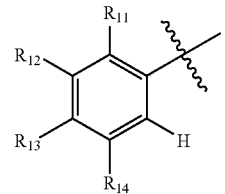

$R_{11}$ is selected from the group consisting of halo, haloalkyl, haloalkoxy, $R_aR_bN$—, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, nitro, wherein the heteroaryls are selected from the group consisting of furanyl, imidazolyl, isothiazolyl, isoxazolyl, 1,2,3-oxadiazoyl, 1,2,5oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl; $R_{12}$ and $R_{13}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole; and $R_{14}$ is selected from the group consisting of hydrogen, halo, haloalkyl, haloalkoxy, $R_aR_bN$—, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl.

Another embodiment of the present invention discloses compounds of formula (I), or therapeutically suitable salt, ester or prodrug, thereof, wherein A is

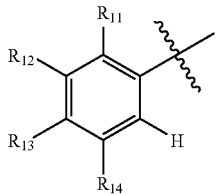

$R_{11}$ is selected from the group consisting of halo, alkoxy, cyano and carboxy; $R_{12}$ and $R_{13}$ together with the carbon atoms to which they are attached, form a substituted or unsubstituted benzene; and R$_{14}$ is hydrogen.

Another embodiment of the present invention discloses compounds of formula (I), or therapeutically suitable salt, ester or prodrug, thereof, wherein A is

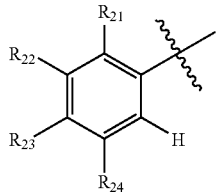

R$_2$, is selected from the group consisting of halo, haloalkyl, haloalkoxy, haloalkylthio, R$_a$R$_b$N—, R$_a$R$_b$Ncarbonyl, R$_a$R$_b$Ncarbonylalkyl, R$_a$R$_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl; R$_{22}$ is selected from the group consisting of hydrogen, halo, haloalkyl, haloalkoxy, haloalkylthio, R$_a$R$_b$N—, R$_a$R$_b$Ncarbonyl, R$_a$R$_b$Ncarbonylalkyl, R$_a$R$_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; R$_{23}$ and R$_{24}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, naphthalene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazolyl.

Another embodiment of the present invention discloses compounds of formula (I), or therapeutically suitable salt, ester or prodrug, thereof, wherein A is

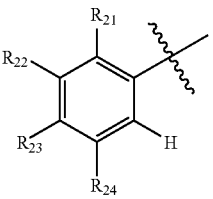

R$_{21}$ is selected from the group consisting of halo, haloalkyl, haloalkoxy, R$_a$R$_b$N—, R$_a$R$_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, nitro, wherein the heteroaryls are selected from the group consisting of furanyl, imidazolyl, isothiazolyl, isoxazolyl, 1,2,3-oxadiazoyl, 1,2,5oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl; R$_{22}$ is selected from the group consisting of hydrogen, halo, haloalkyl, haloalkoxy, R$_a$R$_b$N—, R$_a$R$_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; R$_{23}$ and R$_{24}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, naphthalene, furan, imidazole, isothiazole, isoxazole, 1,3dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazolyl.

Another embodiment of the present invention discloses compounds of formula (I), or therapeutically suitable salt, ester or prodrug, thereof, wherein A is

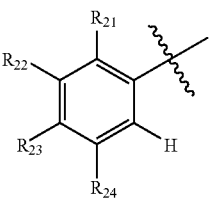

R$_{21}$ is selected from the group consisting of halo and carboxy; R$_{22}$ is selected from the group consisting of hydrogen and halo; and R$_{23}$ and R$_{24}$ together with the carbon atoms to which they are attached, form 1,3-dioxolane.

Another embodiment of the present invention discloses compounds of formula (I), or therapeutically suitable salt, ester or prodrug, thereof, wherein A is

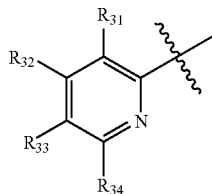

R₃₁ is selected from the group consisting of halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl; R₃₂ is selected from the group consisting of hydrogen, halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; R₃₃ is selected from the group consisting of hydrogen, halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; R₃₄ is selected from the group consisting of hydrogen, halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3triazolyl; and wherein the nitrogen of the pyridine group of A may be optionally substituted with an oxide.

Another embodiment of the present invention discloses compounds of formula (I), or therapeutically suitable salt, ester or prodrug, thereof, wherein A is

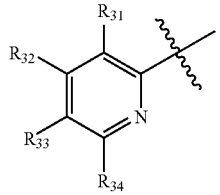

R₃₁ is selected from the group consisting of halo, haloalkyl, haloalkoxy, $R_aR_bN$, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, nitro, wherein the heteroaryls are selected from the group consisting of furanyl, imidazolyl, isothiazolyl, isoxazolyl, 1,2,3-oxadiazoyl, 1,2,5oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl; R₃₂ is selected from the group consisting of hydrogen, halo, haloalkyl, haloalkoxy, $R_aR_bN-$, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; R₃₃ is selected from the group consisting of hydrogen, halo, haloalkyl, haloalkoxy, $R_aR_bN-$, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; R₃₄ is selected from the group consisting of hydrogen, halo, haloalkyl, haloalkoxy, $R_aR_bN-$, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2, 5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; and wherein the nitrogen of the pyridine group of A may be optionally substituted with an oxide.

Another embodiment of the present invention discloses compounds of formula (I), or therapeutically suitable salt, ester or prodrug, thereof, wherein A is

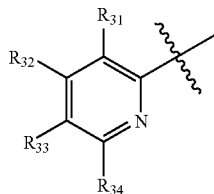

$R_{31}$ is halo; $R_{32}$ is hydrogen; $R_{33}$ is hydrogen; $R_{34}$ is hydrogen; and wherein the nitrogen of the pyridine group of A may be optionally substituted with an oxide.

Another embodiment of the present invention discloses compounds of formula (I), or therapeutically suitable salt, ester or prodrug, thereof, wherein A is

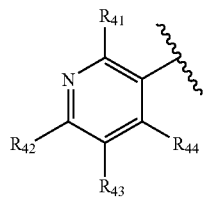

$R_{41}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl; $R_{42}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; $R_{43}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; $R_{44}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; and wherein the nitrogen of the pyridine group of A may be optionally substituted with an oxide; provided that exactly one of $R_{41}$ or $R_{44}$ is hydrogen.

Another embodiment of the present invention discloses compounds of formula (I), or therapeutically suitable salt, ester or prodrug, thereof, wherein A is

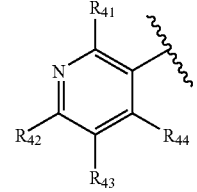

$R_{41}$ is selected from the group consisting of hydrogen, halo, haloalkyl, haloalkoxy, $R_aR_bN$—, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, nitro, wherein the heteroaryls are selected from the group consisting of furanyl, imidazolyl, isothiazolyl, isoxazolyl, 1,2,3-oxadiazoyl, 1,2,5oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl; $R_{42}$ is selected from the group consisting of hydrogen, halo, haloalkyl, haloalkoxy, $R_aR_bN$—, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; $R_{43}$ is selected from the group consisting of hydrogen, halo, haloalkyl, haloalkoxy, $R_aR_bN$—, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; $R_{44}$ is selected from the group consisting of hydrogen, halo, haloalkyl, haloalkoxy, $R_aR_bN-$, $R_aR_bNcarbonyl$, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; and wherein the nitrogen of the pyridine group of A may be optionally substituted with an oxide; provided that exactly one of $R_{41}$ or $R_{44}$ is hydrogen.

Another embodiment of the present invention discloses compounds of formula (I) or therapeutically suitable salt, ester or prodrug, thereof, wherein A is

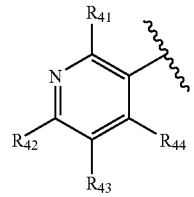

$R_{41}$ is selected from the group consisting of hydrogen, halo and carboxy; $R_{42}$ is hydrogen; $R_{43}$ is selected from the group consisting of hydrogen, halo, alkoxycarbonyl and carboxy; $R_{44}$ is hydrogen; and wherein the nitrogen of the pyridine group of A may be optionally substituted with an oxide; provided that exactly one of $R_{41}$ or $R_{44}$ is hydrogen.

Another embodiment of the present invention discloses compounds of formula (I), or therapeutically suitable salt, ester or prodrug, thereof, wherein A is

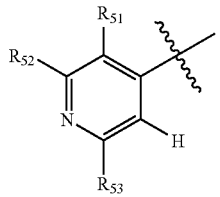

$R_{51}$ is selected from the group consisting of halo, haloalkyl, haloalkoxy, haloalkylthio, $R_aR_bN-$, $R_aR_bNcarbonyl$, $R_aR_bNcarbonylalkyl$, $R_aR_bNsulfonyl$, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl; $R_{52}$ is selected from the group consisting of hydrogen, halo, haloalkyl, haloalkoxy, haloalkylthio, $R_aR_bN-$, $R_aR_bNcarbonyl$, $R_aR_bNcarbonylalkyl$, $R_aR_bNsulfonyl$, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; or $R_{51}$ and $R_{52}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole; $R_{53}$ is selected from the group consisting of hydrogen, halo, haloalkyl, haloalkoxy, haloalkylthio, $R_aR_bN-$, $R_aR_bNcarbonyl$, $R_aR_bNcarbonylalkyl$, $R_aR_bNsulfonyl$, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; and wherein the nitrogen of the pyridine group of A may be optionally substituted with an oxide.

Another embodiment of the present invention discloses compounds of formula (I), or therapeutically suitable salt, ester or prodrug, thereof, wherein A is

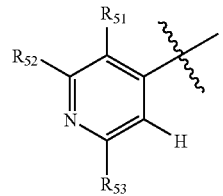

$R_{51}$ is selected from the group consisting of halo, haloalkyl, haloalkoxy, $R_aR_bN$, $R_aR_bNcarbonyl$, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, nitro, wherein the heteroaryls are selected from the group consisting of furanyl, imidazolyl, isothiazolyl, isoxazolyl, 1,2,3-oxadiazoyl, 1,2,5oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl; $R_{52}$ is selected from the group consisting of hydrogen, halo, haloalkyl, haloalkoxy, $R_aR_bN-$, $R_aR_bN$carbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; or $R_{51}$ and $R_{52}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, furan, imidazole, isothiazole, isoxazole, 1,3-dioxolane, 1,2,3-oxadiazole, 1,2,5oxadiazole, oxazole, pyrazine, pyrazole, pyridazine, pyridine, pyrimidine, pyrrole, thiazole, thiophene, triazine and 1,2,3-triazole; $R_{53}$ is selected from the group consisting of hydrogen, halo, habalkyl, haloalkoxy, $R_aR_bN-$, $R_aR_bN$carbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; and wherein the nitrogen of the pyridine group of A may be optionally substituted with an oxide.

Another embodiment of the present invention discloses compounds of formula (I), or therapeutically suitable salt, ester or prodrug, thereof, wherein A is

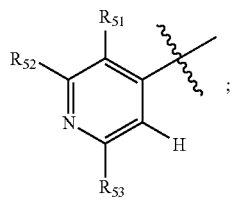

$R_{51}$ and $R_{52}$ together with the carbon atoms to which they are attached, form a benzene; and $R_{53}$ is hydrogen.

Another embodiment of the present invention discloses compounds of formula (I), or therapeutically suitable salt, ester or prodrug, thereof, wherein A is

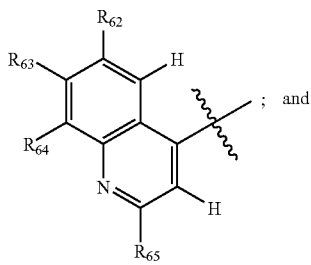

$R_{62}$, $R_{63}$, $R_{64}$ and $R_{65}$ are each independently selected from the group consisting of hydrogen, halo, haloalkyl, haloalkoxy, haloalkylthio, $R_aR_bN-$, $R_aR_bN$carbonyl, $R_aR_bN$carbonylalkyl, $R_aR_bN$sulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl.

Another embodiment of the present invention discloses compounds of formula (I), or therapeutically suitable salt, ester or prodrug, thereof, wherein A is

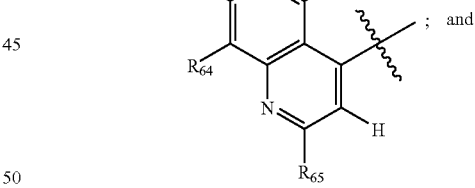

$R_{62}$, $R_{63}$, $R_{64}$ and $R_{65}$ are hydrogen.

Another embodiment of the present invention is directed toward a method of treating diabetes, comprising administering of a therapeutically effective amount of a compound of formula (I).

Another embodiment of the present invention is directed toward a method of treating type II diabetes, comprising administering of a therapeutically effective amount of a compound of formula (I).

Another embodiment of the present invention is directed toward a method of treating hyperglycemia, comprising administering of a therapeutically effective amount of a compound of formula (I).

Another embodiment of the present invention is directed toward a method of treating Syndrome X, comprising administering of a therapeutically effective amount of a compound of formula (I).

Another embodiment of the present invention is directed toward a method of treating hyperinsulinemia, comprising administering of a therapeutically effective amount of a compound of formula (I).

Another embodiment of the present invention is directed toward a method of treating β-cell failure, comprising administering of a therapeutically effective amount of a compound of formula (I).

Another embodiment of the present invention is directed toward a method of treating obesity, comprising administering of a therapeutically effective amount of a compound of formula (I).

Another embodiment of the present invention is directed toward a method of treating satiety disorders, comprising administering of a therapeutically effective amount of a compound of formula (I).

Another embodiment of the present invention is directed toward a pharmaceutical composition comprising a therapeutically effective amount of a compound of formula (I) and a pharmaceutically suitable carrier.

Another embodiment of the present invention is directed toward a method of treating inflammatory bowel syndrome, including Crohn's disease and ulcerative colitis, comprising administration of a therapeutically effective amount of a compound of formula (I).

Another embodiment of the present invention is directed toward a method of treating short bowel disease, comprising administration of a therapeutically effective amount of a compound of formula (I).

Another embodiment of the present invention is directed toward a method of increasing bone marrow transplant efficiency, comprising administration of a therapeutically effective amount of a compound of formula (I).

Another embodiment of the present invention is directed toward a method of treating neurodegenerative and cognitive disorders, including Alzheimer's Disease, comprising administration of a therapeutically effective amount of a compound of formula (I).

DEFINITIONS

As used throughout this specification and the appended claims, the following terms have the following meanings:

DEFINITIONS

As used throughout this specification and the appended claims, the following terms have the following meanings:

The term "alkenyl," as used herein, refers to a straight or branched chain hydrocarbon containing from 2 to 10 carbons and containing at least one carbon-carbon double bond formed by the removal of two hydrogens. The term "alkenyl," as related to the compounds of the present invention, refer to $C_2$-alkenyl, $C_3$-alkenyl, $C_4$-alkenyl, $C_5$-alkenyl, $C_6$-alkenyl, $C_7$-alkenyl, $C_8$-alkenyl, $C_9$-alkenyl or $C_{10}$-alkenyl. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylcarbonyl," as used herein, refers to an alkenyl group, as defined herein, appended to the parent molecular moiety through a carbonyl group, as defined herein.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxyalkylcarbonyl," as used herein, refers to an alkoxyalkyl group, as defined herein, appended to the parent molecular moiety through a carbonyl group, as defined herein.

The term "alkoxyalkoxy," as used herein, refers to an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxycarbonyl," as used herein, refers to an alkoxyalkoxy group, as defined herein, appended to the parent molecular moiety through a carbonyl group, as defined herein.

The term "alkoxyalkoxyalkyl" as used herein, refers to an alkoxyalkoxy group, as defined herein, appended to the parent molecular moiety through an alkyl group, as defined herein.

The term "alkoxyalkoxyalkylcarbonyl" as used herein, refers to an alkoxyalkoxyalkyl group, as defined herein, appended to the parent molecular moiety through a carbonyl group, as defined herein.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylsulfonyl," as used herein, refers to an alkyl group, as defined herein, appended appended to the parent molecular moiety through a sulfonyl group, as defined herein.

The term "alkoxysulfonyl," as used herein, refers to an alkoxy group, as defined herein, appended appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkylthio," as used herein, refers to an alkyl group, as defined herein, appended to the parent molecular moiety through a sulfur atom. Representative examples of alkylthio include, but are not limited, methylsulfanyl, ethylsulfanyl, tert-butylsulfanyl, and hexylsulfanyl.

The term "alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, refers to a monocyclic-ring system, or a bicyclic- or a tricyclic-fused ring system wherein one or more of the fused rings are aromatic. Representative examples of aryl include, but are not limited to, anthracenyl, azulenyl, fluorenyl, indanyl, indenyl, naphthyl, phenyl, and tetrahydronaphthyl.

The aryl groups of the present invention can be substituted with 0, 1, 2, or 3 substituents wherein each substituent occurrence is independently selected from alkenyl, alkoxy, alkoxyalkoxy, alkoxyalkyl, alkoxycarbonyl, alkyl, alkylcarbonyl, alkylsulfonyl, alkynyl, alkylthio, aryl, arylalkyl, carboxy, carboxyalkyl, carboxyalkoxy, carboxyalkoxy, cyano, cyanoalkyl, cycloalkyl, cycloalkylalkyl, formyl, formylalkyl, halo, haloalkyl, haloalkoxy, haloalkylthio, heteroaryl, heterocycle, heteroarylalkyl, heterocyclealkyl, hydroxy, hydroxyalkyl, mercapto, mercaptoalkyl, nitro, $R_aR_bN-$, $R_aR_b$Ncarbonyl, $R_aR_b$Ncarbonylalkyl and $R_aR_b$Nsulfonyl, wherein $R_a$ and $R_b$ are independently selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl, and wherein the substitutuent aryl, heteroaryl, heterocycle, cycloalkyl, the aryl of arylalkyl, the heteroaryl of heteroarylalkyl, the heterocycle of heterocyclealkyl, and the cycloalkyl of cycloalkylalkyl may be substituted with 0, 1 or 2 substituents selected from the group consisting of halo, haloalkyl, haloalkoxy, $R_aR_bN-$, $R_aR_b$Ncarbonyl, alkoxy, alkoxyalkoxy, alkoxyalkyl, alkoxycarbonyl, cyano, cyanoalkyl, hydroxy, hydroxyalkyl, alkyl, alkenyl, carboxy, carboxyalkyl, carboxyalkoxy, carboxyalkoxy, and alkylcarbonyl, wherein $R_a$ and $R_b$ are defined herein.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylcarbonyl," as used herein, refers to an aryl group, as defined herein, appended to the parent molecular moiety through a carbonyl group, as defined herein.

The term "arylalkylsulfonyl," as used herein, refers to an arylalkyl group, as defined herein, appended to the parent molecular moiety through a sulfonyl group, as defined herein.

The term "arylsulfonyl," as used herein, refers to an aryl group, as defined herein, appended to the parent molecular moiety through a sulfonyl group, as defined herein.

The term "carbonyl," as used herein, refers to a —C(O)— group.

The term "carboxy," as used herein, refers to a HO$_2$C— group.

The term "carboxyalkyl," as used herein, refers to a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "carboxyalkoxy," as used herein, refers to a carboxy group, as defined herein, appended to the parent molecular moiety through an alkoxy group, as defined herein.

The term "cyano," as used herein, refers to a NC— group.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl," as used herein, refers to a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo(3.1.1)heptane, bicyclo(2.2.1)heptane, bicyclo(2.2.2)octane, bicyclo(3.2.2)nonane, bicyclo(3.3.1) nonane, and bicyclo(4.2.1)nonane. Tricyclic ring systems are exemplified by a bicyclic ring system in which two nonadjacent carbon atoms of the bicyclic ring are linked by a bond or an alkylene bridge of between one and three carbon atoms. Representative examples of tricyclic-ring systems include, but are not limited to, tricyclo(3.3.1.0$^{3,7}$) nonane and tricyclo(3.3.1.1$^{3,7}$)decane (adamantane).

The cycloalkyl groups of this invention may be substituted with 0, 1, 2 or 3 substituents wherein each substituent occurrence is selected from alkenyl, alkoxy, alkoxyalkoxy, alkoxyalkyl, alkoxycarbonyl, alkyl, alkylcarbonyl, alkylsulfonyl, alkynyl, alkylthio, aryl, carboxy, carboxyalkyl, carboxyalkoxy, carboxyalkoxy, cyano, cyanoalkyl, cycloalkyl, cycloalkylalkyl, formyl, formylalkyl, halo, haloalkyl, haloalkoxy, haloalkylthio, heteroaryl, heterocycle, hydroxy, hydroxyalkyl, mercapto, mercaptoalkyl, nitro, $R_aR_bN-$, $R_aR_b$Ncarbonyl, $R_aR_b$Ncarbonylalkyl and $R_aR_b$Nsulfonyl, wherein $R_a$ and $R_b$ are defined herein, and wherein the substituent aryl, heteroaryl and heterocycle groups may be optionally substituted with 0, 1, 2 or 3 substituents wherein each substitutent occurrence is selected from alkenyl, alkoxy, alkoxyalkoxy, alkoxyalkyl, alkoxycarbonyl, alkyl, alkylcarbonyl, alkylsulfonyl, alkynyl, alkylthio, carboxy, carboxyalkyl, carboxyalkoxy, carboxyalkoxy, cyano, cyanoalkyl, cycloalkyl, cycloalkylalkyl, formyl, formylalkyl, halo, haloalkyl, haloalkoxy, haloalkylthio and hydroxy.

The term "cycloalkylalkyl," as used herein, refers to a cycloalkyl group, as defined herein, appended to the parent molecular moiety through an alkyl group, as definedherein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "cycloalkylcarbonyl," as used herein, refers to a cycloalkyl group, as defined herein, appended to the parent molecular moiety through a carbonyl group, as defined herein.

The term "dialkylsulfonyl," as used herein, refers to two independent alkyl groups, as defined herein, appended to the parent molecular moiety through a sulfonyl group, as defined herein.

The term "formyl," as used herein, refers to a —C(O)H group.

The term "formylalkyl," as used herein, refers to a formyl group, as defined herein, appended to the parent molecular moiety through an alkyl group, as defined herein. Representative examples of formylalkyl include, but are not limited to, formylmethyl and 2-formylethyl.

The term "halo" or "halogen," as used herein, refers to Cl—, Br—, I— or F—.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkoxy," as used herein, refers to at least one halogen, as defined herein, appended to the parent molecular moiety through an alkoxy group, as defined herein.

The term "haloalkylthio," as used herein, refers to at least one halogen, as defined herein, appended to the parent molecular moiety through an alkylthio group, as defined herein.

The term "heteroaryl," as used herein, means a monocyclic or a bicyclic ring. The monocyclic heteroaryl rings of the present invention may exist as a 5 or 6 membered ring. The 5 membered heteroaryl ring has two double bonds and contains one, two, three or four heteroatoms independently selected from the group consisting of N, O, and S. The 6 membered heteroaryl ring has three double bonds and contains one, two, three or four heteroatoms independently selected from the group consisting of N, O, and S. The bicyclic heteroaryl ring consists of the 5 or 6 membered heteroaryl ring fused to a distal ring, wherein the distal ring is selected from the group consisting of aryl, cycloalkyl, cycloalkenyl, heteroaryl, and a 5 or 6 membered heterocycle ring. Nitrogen heteroatoms contained within the heteroaryl may be optionally oxidized to the N-oxide or optionally protected with a nitrogen protecting group known to those of skill in the art. The heteroaryl is connected to the parent molecular moiety through any carbon atom or any nitrogen atom contained within the heteroaryl. Representative examples of heteroaryl include, but are not limited to, benzothienyl, benzoxadiazolyl, cinnolinyl, 5,6-dihydroisoquinolinyl, 7,8-dihydroisoquinolinyl, 5,6-dihydroquinolinyl, 7,8-dihydroquinolinyl, furopyridinyl, furyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, pyridinium N-oxide, quinolinyl, 5,6,7,8-tetrahydroisoquinolinyl, 5,6,7,8-tetrahydroquinolinyl, tetrazolyl, thiadiazolyl, thiazolyl, thienopyridinyl, thienyl, triazolyl, and triazinyl.

According to the present invention, heteroaryls of the present invention can be substituted with 0, 1, 2,or 3 substituents independently selected from alkenyl, alkoxy, alkoxyalkoxy, alkoxyalkyl, alkoxycarbonyl, alkyl, alkylcarbonyl, alkylsulfonyl, alkynyl, alkylthio, aryl, arylalkyl, carboxy, carboxyalkyl, carboxyalkoxy, carboxyalkoxy, cyano, cyanoalkyl, cycloalkyl, cycloalkylalkyl, formyl, formylalkyl, halo, haloalkyl, haloalkoxy, haloalkylthio, heteroaryl, heterocycle, heteroarylalkyl, heterocyclealkyl, hydroxy, hydroxyalkyl, mercapto, mercaptoalkyl, nitro, $R_aR_bN$—, $R_aR_b$Ncarbonyl, $R_aR_b$Ncarbonylalkyl and $R_aR_b$Nsulfonyl, wherein $R_a$ and $R_b$ are independently selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl, and wherein the substituent aryl, heteroaryl, heterocycle, cycloalkyl, the aryl of arylalkyl, the heteroaryl of heteroarylalkyl, the heterocycle of heterocyclealkyl, and the cycloalkyl of cycloalkylalkyl may be substituted with 0, 1 or 2 substituents selected from the group consisting of halo, haloalkyl, haloalkoxy, $R_aR_bN$—, $R_aR_b$Ncarbonyl, alkoxy, alkoxyalkoxy, alkoxyalkyl, alkoxycarbonyl, cyano, cyanoalkyl, hydroxy, hydroxyalkyl, alkyl, alkenyl, carboxy, carboxyalkyl, carboxyalkoxy, carboxyalkoxy, and alkylcarbonyl.

The term, "heteroarylalkyl," as used herein, refers to a heteroaryl group as defined herein, appended to the parent molecular moiety through an alkyl group, as defined herein.

The term "heterocycle" or "heterocyclic" as used herein, means a monocyclic ring or a bicyclic ring or a tricyclic ring. The monocyclic ring consists of a 3, 4, 5, 6 or 7 membered ring which contains at least one heteroatom independently selected from the group consisting of oxygen, nitrogen and sulfur. The 3 or 4 membered ring contains 1 heteroatom. The 5 membered ring contains zero or one double bond and one, two or three heteroatoms. The 6 or 7 membered ring contains zero, one or two double bonds and one, two or three heteroatoms. Representative examples of the monocyclic heterocyclic ring include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocyclic ring consists of the monocyclic heterocyclic ring fused to a distal ring, wherein the distal ring is selected from the group consisting of aryl, cycloalkyl, cycloalkenyl, heteroaryl and another monocyclic heterocyclic ring. Representative examples of the bicyclic heterocyclic ring include, but are not limited to, 1,3-benzodioxolyl, 1,3-benzodithiolyl, 2,3dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. The tricyclic heterocyclic ring consists of the bicyclic heterocyclic ring fused to a phenyl group or the bicyclic heterocyclic ring fused to a cycloalkyl group or the bicyclic heterocyclic ring fused to a cycloalkenyl group or the bicyclic heterocyclic ring fused to another monocyclic heterocyclic ring. Representative examples of tricyclic heterocyclic ring include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl.

According to the present invention, heterocycles can be substituted with 0, 1, 2 or 3 substituents wherein each substitutent occurrence is independently selected from alkenyl, alkoxy, alkoxyalkoxy, alkoxyalkyl, alkoxycarbonyl, alkyl, alkylcarbonyl, alkylsulfonyl, alkynyl, alkylthio, arylalkyl, carboxy, carboxyalkyl, carboxyalkoxy, carboxyalkoxy, cyano, cyanoalkyl, cycloalkyl, cycloalkylalkyl, formyl, formylalkyl, halo, haloalkyl, haloalkoxy, haloalkylthio, heteroaryl, heterocycle, heteroarylalkyl, heterocyclealkyl, hydroxy, hydroxyalkyl, mercapto, mercaptoalkyl, nitro, phenyl, $R_aR_bN$—, $R_aR_b$Ncarbonyl, $R_aR_b$Ncarbonylalkyl and $R_aR_b$Nsulfonyl, wherein $R_a$ and $R_b$ are independently selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl, and wherein phenyl, heteroaryl, heterocycle, cycloalkyl, the aryl of arylalkyl, the heteroaryl of heteroarylalkyl, the heterocycle of heterocyclealkyl, and the cycloalkyl of cycloalkylalkyl can be substituted with 0, 1 or 2 substituents selected from the group consisting of halo, haloalkyl, haloalkoxy, $R_aR_bN-$, $R_aR_b$Ncarbonyl, alkoxy, alkoxyalkoxy, alkoxyalkyl, alkoxycarbonyl, cyano, cyanoalkyl, hydroxy, hydroxyalkyl, alkyl, alkenyl, carboxy, carboxyalkyl, carboxyalkoxy, carboxyalkoxy, and alkylcarbonyl.

The term "heterocyclealkyl," as used herein, refers to a heterocycle, as defined herein, appended to the parent molecular moiety through an alkyl group, as defined herein. Representative examples of heterocyclealkyl include, but are not limited to, pyridin-3 ylmethyl and 2-pyrimidin-2-ylpropyl and the like.

The term "heterocyclecarbonyl," as used herein, refers to a heterocycle, as defined herein, appended to the parent molecular moiety through an carbonyl group, as defined herein. Representative examples of heterocyclecarbonyl include, but are not limited to, pyridin-3-ylcarbonyl and 2-pyrimidin-2-ylcarbonyl and the like.

The term "hydroxy," as used herein, refers to an —OH group.

The term "hydroxyalkyl," as used herein, refers to a hydroxy group, as defined herein, appended to the parent molecular moiety through an alkyl group, as defined herein. Representative examples of hydroxyalkyl include, but are not limited to, 2-hydroxyethyl, 2-hydroxypropyl, 3-hydroxybutyl and the like.

The term "mercapto," as used herein, refers to a —SH group.

The term "mercaptoalkyl," as used herein, refers to a mercapto group, as defined herein, appended to the parent molecular moiety through an alkyl group, as defined herein. Representative examples of mercaptoalkyl include, but are not limited to, 2-mercaptoethyl and 3-mercaptopropyl.

The term "nitro," as used herein, refers to a —NO₂ group.

The term "sulfonyl," as used herein, refers to a —SO₂— group.

The term "$R_aR_bN-$," as used herein, refers to both $R_a$ and $R_b$, which are independently defined as a member selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl, appended to the parent molecular moiety through a nitrogen atom.

The term "$R_aR_b$Ncarbonyl," as used herein, refers to $R_aR_bN$, as defined herein, appended to the parent molecular moiety through a carbonyl group, as defined herein.

The term "$R_aR_b$Ncarbonylalkyl," as used herein, refers to $R_aR_b$Ncarbonyl, as defined herein, appended to the parent molecular moiety through an alkyl group, as defined herein.

The term "$R_aR_b$Nsulfonyl," as used herein, refers to $R_aR_bN$, as defined herein, appended to the parent molecular moiety through a sulfonyl group, as defined herein.

The present invention is also directed to a method of treating disorders mediated by DPP-IV through inhibition of enzymatic activity. Disorders known to be regulated through enzymatic activity are diabetes, especially type II diabetes, as well as hyperglycemia, Syndrome X, hyperinsulinemia, β-cell failure, obesity, atherosclerosis, and various immunomodulatory diseases. Therefore, according to an embodiment of the present invention there are provided compounds of formula (I), which are useful for the treatment of diabetes, especially type II diabetes, as well as hyperglycemia, Syndrome X, hyperinsulinemia, β-cell failure, obesity, satiety disorders, atherosclerosis, and various immunomodulatory diseases.

The present compounds can exist as therapeutically suitable salts. The term "therapeutically suitable salt," refers to salts or zwitterions of the compounds which are water or oil-soluble or dispersible, suitable for treatment of disorders without undue toxicity, irritation, and allergic response, commensurate with a reasonable benefit/risk ratio, and effective for their intended use. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetic, trifluoroacetic, glutamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like. The present invention contemplates pharmaceutically suitable salts formed at the nitrogen of formula (I–II).

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

The present compounds can also exist as therapeutically suitable prodrugs. The term "therapeutically suitable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds that are rapidly transformed in vivo to the parent compounds of formula (I–II) for example, by hydrolysis in blood.

Asymmetric centers can exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described herein and resolved by techniques well-known in the art.

Geometric isomers can exist in the present compounds. The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration.

Therapeutic compositions of the present compounds comprise an effective amount of the same formulated with one or more therapeutically suitable excipients. The term "therapeutically suitable excipient," as used herein, represents a non-toxic, solid, semi-solid or liquid filler, diluent, encapsulating material, or formulation auxiliary of any type. Examples of therapeutically suitable excipients include sugars; cellulose and derivatives thereof; oils; glycols; solutions; buffering, coloring, releasing, coating, sweetening, flavoring, and perfuming agents; and the like. These therapeutic compositions can be administered parenterally, intracisternally, orally, rectally, or intraperitoneally.

Liquid dosage forms for oral administration of the present compounds comprise formulations of the same as emulsions, microemulsions, solutions, suspensions, syrups, and elixirs. In addition to the compounds, the liquid dosage forms can contain diluents and/or solubilizing or emulsifying agents. Besides inert diluents, the oral compositions can include wetting, emulsifying, sweetening, flavoring, and perfuming agents. Injectable preparations of the present compounds comprise sterile, injectable, aqueous and oleaginous solutions, suspensions or emulsions, any of which can be optionally formulated with parenterally suitable diluents, dispersing, wetting, or suspending agents. These injectable preparations can be sterilized by filtration through a bacterial-retaining filter or formulated with sterilizing agents that dissolve or disperse in the injectable media.

Inhibition of DPP-IV by the compounds of the present invention can be delayed by using a liquid suspension of crystalline or amorphous material with poor water solubility. The rate of absorption of the compounds depends upon their rate of dissolution which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions that are compatible with body tissues.

Solid dosage forms for oral administration of the present compounds include capsules, tablets, pills, powders, and granules. In such forms, the compound is mixed with at least one inert, therapeutically suitable excipient such as a carrier, filler, extender, disintegrating agent, solution retarding agent, wetting agent, absorbent, or lubricant. With capsules, tablets, and pills, the excipient can also contain buffering agents. Suppositories for rectal administration can be prepared by mixing the compounds with a suitable nonirritating excipient that is solid at ordinary temperature but fluid in the rectum.

The present compounds can be micro-encapsulated with one or more of the excipients discussed previously. The solid dosage forms of tablets, dragees, capsules, pills, and granules can be prepared with coatings and shells such as enteric and release controlling. In these forms, the compounds can be mixed with at least one inert diluent and can optionally comprise tableting lubricants and aids. Capsules can also optionally contain opacifying agents that delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

Disorders that can be treated or prevented in a patient by administering to the patient, a therapeutically effective amount of compound of the present invention in such an amount and for such time as is necessary to achieve the desired result. The term "therapeutically effective amount," refers to a sufficient amount of a compound of formula (I) to effectively ameliorate disorders by inhibiting DPP-IV at a reasonable benefit/risk ratio applicable to any medical treatment. The specific therapeutically effective dose level for any particular patient will depend upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The total daily dose of the compounds of the present invention necessary to inhibit the action of DPP-IV in single or divided doses can be in amounts, for example, from about 0.01 to 50 mg/kg body weight. In a more preferred range, compounds of the present invention inhibit the action of DPP-IV in a single or divided doses from about 0.05 to 25 mg/kg body weight. Single dose compositions can contain such amounts or submultiple doses thereof of the compounds of the present invention to make up the daily dose. In general, treatment regimens comprise administration to a patient in need of such treatment from about 1 mg to about 1000 mg of the compounds per day in single or multiple doses.

BIOLOGICAL DATA

Isolation of Rat DPP-IV

DPP-IV was purified to homogeneity (electrophoretic) from rat kidney as described in *Arch. Biochem. Biophy.* 1995, 323, 148–154. Rat kidney (120 g) was homogenized in 4 volumes of water and the homogenate centrifuged for 15 minutes at 1000g. The pH of the supernatant was adjusted to 3.9 with 1 M HCl and the enzyme solubilized by autolysis for 18 hours at 37° C. The pH of the supernatant collected after centrifugation was adjusted to 7.2 with 1 M Trizma base and the enzyme was precipitated with $(NH_4)_2SO_4$ at 90% saturation (662 g solid ammonium sulfate per liter of solution). The solubilized precipitate was chromatographed on Sephadex G-200 (1 m×5 cm) equilibrated with a 10 mM Tris-HCl buffer pH 7.5 containing NaCl at a final concentration of 0.1 M and developed from the bottom. Fractions containing enzymatic activity were pooled, chromatographed on DE-52 (16×2.5 cm) equilibrated with 10 mM Tris-HCl, pH 7.5, and eluted with a 250-mL linear 0–0.4 M NaCl gradient prepared in 10 mM Tris-HCl. DPP-IV was then resolved from other brush border peptidases by chromatography on a phenyl Sepharose column (12×2 cm) equilibrated with 25% $(NH_4)_2SO_4$ at saturation(144 g ammonium sulfate per liter of 0.05 M Tris-HCl, pH 7.5). The enzyme was eluted in a homogeneous form with a 200-mL linear gradient of 25–0% $(NH_4)_2SO_4$, prepared in 0.05 M Tris HCl buffer.

Partial Purification of Human DPP-IV

Caco-2 cells were obtained from American Type Culture Collection (P.O. Box 3605, Manassas, Va.), cultured and maintained at 37° C. with 5% $CO_2$ in low glucose DMEM media supplemented with 10% Fetal Bovine Serum and antibiotic/antimycotic. In preparation for making an extract, cells were seeded at a density to achieve confluence within 7 days. The cells were cultured for an additional 14 days to allow for maximal DPPIV expression. On the day of harvest, cells were washed once with Dulbecco's PBS and solubilized in a 10 mM NaCl containing 50 mM Tris HCl, 0.5% Nonidet P40 and 0.3 ug/mL aprotinin at pH 8.0. The extract was clarified by centrifugation at 35,000 g for 30 minutes at 4° C.

Inhibition Constant Determination for DPP-IV

DPP-IV activity was determined by measuring the rate of hydrolysis of a surrogate substrate Gly-Pro-7-amido-methylcoumarin (Gly-Pro-AMC, Catalogue #G-2761, Sigma, St. Louis, Mo.). The assay is carried out at room temperature in black 96 well polypropylene or polyethylene plates in a total volume of 100 µL per well. Appropriate dilutions of the compounds are made in DMSO and then diluted ten fold into water. 10 µL of 5 concentrations of the compound of formula (I) (inhibitor) or 10% DMSO in water are added to individual wells containing 80 µL of DPP-IV diluted in assay buffer containing 25 mM HEPES (pH 7.5), 150 mM NaCl and 0.12 mg/mL BSA. After 10 minutes at room temperature, the reaction is initiated by adding 10 µL of either 280, 700, 1750, or 3500 µM Gly-Pro-AMC in water. The DPP-IV activity results in the formation of the fluorescent product amido-methylcoumarin (AMC) which is continuously monitored by excitation at 350 nm and measurement of fluorescent emission at 460 nm every 112 seconds for 37 minutes using an appropriate plate reader. The fluorescence at 460 nm is converted to nanomoles of AMC using a standard curve and the initial rate of AMC formation is calculated. For each concentration of compound of formula (I) (inhibitor) or DMSO control, the initial rates are used to fit the rectangular hyperbola of Michaelis-Menten by non-linear regression analysis (GraphPad Software Prism 3.0). The ratio of the apparent Km/Vmax vs. inhibitor concentration is plotted and the competitive Ki is calculated by linear regression to be the negative x-intercept. The uncompetitve Ki is similarly calculated from the x-intercept of the plot of the reciprocal of the apparent Vmax versus the inhibitor concentration (Cornish Bowden, A. 1995. Fundamentals of Enzyme Kinetics. Revised edition. Portland Press, Ltd., London, U.K.).

The compounds of the present invention were found to inhibit DPP-IV induced fluorescence with inhibitory constants in a range of about 0.0003 µM to about 0.03 µM.

For the determination of chemical stability, compounds of the present invention are assayed using the following protocol:

Chemical Stability Assay

A solution of each DPP-IV compound was prepared in an appropriate mobile phase. This was injected and analyzed by HPLC to identify the parent drug peak in the chromatograms. Stability solutions were prepared in 50 mM phosphate buffer pH 7.4 adjusted to µ=0.155. Samples were weighed using a Mettler-Toledo microbalance and transferred into a 20 ml glass scintillation vial or a volumetric flask. The phosphate buffer pH 7.4 was added with an EDP Plus 10 ml electronic pipette. The samples were sonicated for approximately 2 minutes and filtered using a PTFE membrane syringe filter. The filtrate was transferred to amber HPLC vials and placed in an autosampler at 37° C. The first sample was immediately injected and counted as the time zero sample. The solution concentration was measured at various timepoints using an appropriate HPLC method. After data acquisition was completed, the chromatograms were processed for each compound. The rate and half-life were determined from a plot of $log_{10}$ peak area remaining/peak area at zero time vs. exposure time @37° C. using Microsoft® Excel 2000. Rates of reaction and half-lives were calculated using a pseudo-first order kinetic model.

Preferred compounds of the present invention are potent inhibitors of DPP-IV (with $K_I$ values <10 nM) and are resistant to the internal cyclization reaction described above ($T_{1/2}$>10 hours, suitable for once-daily dosing). These compounds are uniquely suited for the blockade of DPP-IV activity, and the treatment of diseases related to excessive DPP-IV activity, in a human therapeutic setting.

As disclosed in WO04/016587, compounds α, β and γ typify DPP-IV inhibitors where activity and stability are not simultaneously achieved. Thus, Comparative compound α is a relatively potent inhibitor of DPP-IV ($K_I$=8.3 nM), but suffers from poor intrinsic chemical stability ($T_{1/2}$=5.3 hrs). On the other hand, Comparative compound β and Comparative compound γ are sufficiently stable to cyclization (chemical stability half-lives of 16.4 and 12.2 hours, respectively), but neither is potent as a DPP-IV inhibitor ($K_I$=33 and 720 nM).

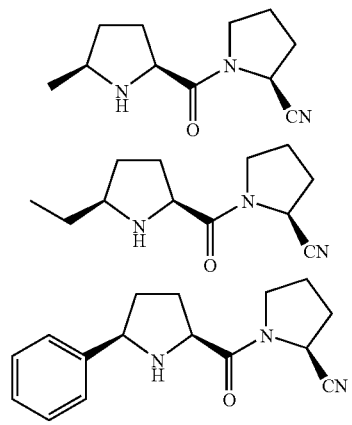

Comparative compound α Comparative compound β Comparative compound γ

Representative potency and chemical stability data of both the Comparative compounds and the compounds of the present invention are shown below in Table I. Compounds of the present invention are both potent and stable, as indicated for Compounds listed below.

TABLE I

DPP-IV inhibitory potency and chemical stability data for representative compounds

| Compound | Ki, uM | Chem stability (T½, hrs) |
|---|---|---|
| α | 0.0083 | 5.3 |
| β | 33 | 16.4 |
| γ | 720 | 12.2 |
| A1 | 0.0007 | 16.7 |
| B1 | 0.002 | 26.5 |
| C1 | 0.002 | >24 |
| D1 | 0.0025 | 10.8 |
| E1 | 0.0013 | 19.9 |
| F1 | 0.0033 | 65.4 |
| G1 | 0.0017 | >24 |
| H1 | 0.001 | 19.8 |
| I1 | 0.0015 | 9.7 |
| J1 | 0.0147 | |
| K1 | 0.0089 | 41 |
| L1 | 0.0076 | |
| M1 | 0.0007 | 23 |
| N1 | 0.0013 | |
| O1 | 0.0011 | |
| P1 | 0.0039 | |
| Q1 | 0.0013 | |
| R1 | 0.0021 | |
| S1 | 0.0024 | |
| T1 | 0.0022 | |
| U1 | 0.0016 | |
| V1 | 0.0059 | |
| W1 | 0.0009 | |
| X1 | 0.0035 | |
| Y1 | 0.0007 | |
| Z1 | 0.0035 | |
| A2 | 0.0105 | |
| B2 | 0.0101 | |
| C2 | 0.0008 | |
| D2 | 0.0011 | |
| E2 | 0.0056 | |
| F2 | 0.0099 | |
| G2 | 0.0013 | |
| H2 | 0.0003 | |
| I2 | 0.0009 | |
| J2 | 0.0064 | |
| K2 | 0.0013 | |
| L2 | 0.0069 | |
| M2 | 0.0089 | |
| N2 | 0.004 | |
| O2 | 0.0232 | |
| P2 | 0.0004 | |
| Q2 | 0.0007 | |
| R2 | 0.0247 | |
| S2 | 0.001 | |
| T2 | 0.0016 | |
| U2 | 0.0036 | |
| V2 | 0.0014 | |
| W2 | 0.0028 | |
| X2 | 0.0011 | |
| Y2 | 0.0007 | |
| Z2 | 0.002 | |
| A3 | 0.0052 | |
| B3 | 0.0025 | |
| C3 | 0.0036 | |
| D3 | 0.0005 | |
| E3 | 0.0015 | |
| F3 | 0.0238 | |
| G3 | 0.0081 | |
| H3 | 0.0026 | |
| I3 | 0.0017 | |
| J3 | 0.0026 | |
| K3 | 0.0013 | |
| L3 | 0.0007 | |
| M3 | 0.0046 | |
| N3 | 0.0006 | |
| O3 | 0.0012 | |
| P3 | 0.0031 | |
| Q3 | 0.002 | |
| R3 | 0.0013 | |
| S3 | 0.0007 | |
| T3 | 0.0046 | |
| U3 | 0.001 | |
| V3 | 0.0013 | |
| W3 | 0.0092 | |
| X3 | 0.0066 | |
| Y3 | 0.0008 | |
| Z3 | 0.0036 | |
| A4 | 0.0018 | |
| B4 | 0.0047 | |
| C4 | 0.0019 | |
| D4 | 0.0023 | |
| E4 | 0.002 | |
| F4 | 0.0055 | |
| G4 | 0.0009 | |
| H4 | 0.0015 | |
| I4 | 0.0151 | |
| J4 | 0.02 | |
| K4 | 0.0039 | |
| L4 | 0.0027 | |
| M4 | 0.0171 | |
| N4 | 0.0011 | |
| O4 | 0.001 | |
| P4 | 0.0014 | |
| Q4 | 0.0017 | |

As inhibitors of DPP-IV action, the compounds of the present invention are useful in treating disorders that are mediated by DPP-IV. Disorders that are mediated by DPP-IV include diabetes, type II diabetes, hyperglycemia, Syndrome X, hyperinsulinemia, β-cell failure and obesity. Therefore the compounds of the present invention are useful in treating the disorder of diabetes, type II diabetes, hyperglycemia, Syndrome X, hyperinsulinemia, β-cell failure and obesity.

Compounds of the present invention are evaluated for the ability to treat diabetes using an acute oral glucose tolerance test (OGTT) as follows: Insulin resistant female ZDF rats, 11 weeks of age, on a normal chow diet, are fasted overnight. A baseline tail snip blood sample is taken to measure glucose levels (Precision PCx glucose meter, Abbott Laboratories, Abbott Park, Ill.) at the beginning of the experiment. Immediately after this baseline sample, compounds of the present invention (or placebo) are dosed orally. Four hours later, a tail snip blood glucose measurement is taken, immediately followed by an oral glucose dose (OGTT, 2 gm/kg). The glucose excursion is followed for 2 hr with samples taken at 10, 20, 30, 60 and 120 min post OGTT. These timed glucose data are used to construct a glucose excursion curve, from which an area under the glucose curve (AUGC) is determined. Data are reported as the baseline-adjusted area under the glucose curve (deltaAUGC) for drug and control groups.

| Dose | δ AUGC |
|---|---|
| Control | 9,900 mg/mL/dL |
| Example 54 1.0 mg/kg | 7,600 (−24%) |
| Example 54 3.0 mg/kg | 7,300 (−27%) |

Dipeptidyl-peptidase IV (DPP-IV, EC 3.4.14.5; CD26) is a post-proline cleaving serine protease with significant homology to other alpha-beta hydroxylases (e.g. prolyl oligopeptidase). DPP-IV is found throughout the body, both circulating in plasma and as a type II membrane protein produced by a variety of tissues, including kidney, liver and intestine. DPP-IV plays a role in the cleavage of specific substrates with accessible amino-terminal Xaa-Pro- or Xaa-Ala-dipeptide sequences, resulting in their inactivation or alteration in their biological activities. Important DPP-IV substrates include growth hormone releasing hormone, glucagon-like peptides (GLP)-1 and 2, gastric inhibitory polypeptide (GIP) and certain chemokines like RANTES (regulated on activation, normal T cell expressed and secreted), stromal cell-derived factor, eotaxin, and macrophage-derived chemokine (Mentlein, R. *Regulatory Peptides,* 1999,85, 9–24).

The DPP-IV substrate, glucagon-like peptide (GLP)-1, is released from L cells in the distal small intestine and colon after oral ingestion of nutrients. The active GLP-1 (7-36) amide is an incretin that increases glucose stimulated insulin secretion (Drucker, D. J. *Diabetes,* 1998, 47, 159–169). Other activities attributed to GLP-1 (7-36) amide include stimulation of insulin gene expression, trophic effects on pancreatic beta cells, inhibition of glucagon secretion, promotion of satiety, inhibition of food intake, and slowing of gastric emptying (Drucker, D. J. *Diabetes,* 1998, 47, 159–169). These effects of GLP-1 (7-36) amide contribute to glucose homeostasis and the normalization of blood glucose levels in conditions of impaired glucose tolerance. In this regard, GLP-1 (7-36) amide has been demonstrated to reduce postprandial and fasting glycemia in patients with insulin-dependent and non-insulin-dependent diabetes mellitus (Nauck, et al., *Hormone Metab. Res.* 2002,29, 411–416; Gutniak et al., *J. Internal Medicine,* 2001, 250, 81–87; Rauchman, et al., *Diabetologia.* 1997, 40, 205–11; Ahren, B., *BioEssays* 1998, 20, 642–51). GLP-1 based therapy has therapeutic potential for the treatment of type 2 diabetes. However, active GLP-1 (7-36) amide is rapidly converted to GLP-1 (9-36) amide by DPP-IV cleavage of the amino-terminal His-Ala- dipeptide of GLP-1 (7-36) amide (Mentlein, et al., *Eur. J. Biochem.* 1993, 214, 829–835). The resulting GLP-1 (9-36) amide is inactive and is an antagonist of the GLP-1 receptor (Knudson, et al., *Eur. J. Pharmacol.* 1996, 318, 429–35). The short half-life of GLP-1 (7-36) amide in the circulation (1–1.5 minutes) makes it impractical as a therapeutic agent and has led to the development of alternative strategies to enhance the anti-diabetogenic activity of GLP-1. One strategy is to increase the circulating half-life of GLP-1, by inhibiting DPP-IV activity (Deacon, et al., *Diabetes* 1995, 44 1126–31). Inhibition of DPP-IV in vivo increases the level of circulating GLP-1 (7-36) amide with a concomitant increase in its insulinotropic effect (Deacon, et al., *Diabetes.* 1998, 47, 764–9). A DPP-IV inhibitor has been demonstrated to improve glucose tolerance in non-insulin-dependent diabetes mellitus (Ahren B, et al., *Diabetes Care* 2002, 25, 869–875). Therefore, the compounds of the present invention, including but not limited to those specified in the examples can be used in the treatment of conditions caused by or associated with impaired glucose tolerance including the prevention or treatment of diabetes, especially non-insulin-dependent diabetes mellitus, hyperglycemia, hyperinsulinemia and metabolic syndrome (Johannsson, et al., *J. Endocrinol. Invest* 1999, 22(5 Suppl), 41–6).

Striking similarities exist between the metabolic syndrome (syndrome X) and untreated growth hormone deficiency. Abdominal/visceral obesity and insulin resistance characterize both syndromes (Reaven, G M, *Physiol. Rev.* 1995, 75, 473–86; Johansson, et al., *Metabolism* 1995, 44, 1126–29). Growth hormone favorably effects some of the perturbations associated with abdominal/visceral obesity, including reduction in abdominal/visceral obesity, improved insulin sensitivity and lipoprotein metabolism and reduction in diastolic blood pressure (Barreto-Filho, et al., *J. Clin. EndocrinoL Metab.* 2002, 87(5), 2018–23; Colao et al., *J. Clin. Endocrinol. Metab.* 2002, 87(3), 1088–93; Gotherstrom, et al., *J. Clin. Endocrinol. Metab.* 2001, 86(10), 4657–65; Johannsson, et al., *J. Endocrinol. Invest.* 1999, 22(5 Suppl), 41–6; Johannsson, et al., *J. Clin. Endocrinol. Metab.* 1997, 82(3), 727–34).

For the treatment of diabetes or Syndrome X, compounds of the present invention may be used alone, or in combination with any existing anti-diabetic agent. Agents which may be used in combination with the compounds of the present invention include, but are not limited to insulin, an insulin analog such as mecasermin and the like, an insulin secretagogue such as nateglinide and the like, a biguanide such as metformin and the like, a sulfonylurea such as chlorpropamide, glipizide, glyburide, and the like, an insulin sensitizing agent such as a PPARγ agonist such as troglitazone, pioglitazone, rosiglitazone, and the like, an a-glucosidase inhibitor such as acarbose, voglibose, miglitol and the like, an aldose reductase inhibitor such as zopolrestat and the like, a metiglinide such as repaglinide and the like, a glycogen phosphorylase inhibitor, GLP-1 or a mimetic of GLP-1 such as exendin-4, or other such anti-diabetic agents that are known to one skilled in the art. The ability of the compounds of the present invention to treat diabetes, alone or in combination with another agent, can be demonstrated according to the methods described by Zander, M.; Mustafa, T.; Toft-Nielsen, M.-B.; Madsbad, S.; Holst, J. J. in *Diabetes Care* 2001, 24, 720–725; or, according to the methods described herein.

DPP-IV-mediated proteolysis has been established as a major route of growth hormone releasing hormone (GHRH) degradation and inactivation (Kubiak, et al., *Drug Metab. Dispos.* 1989, 17, 393–7). GHRH-derivatives that are resistant to DPP-IV cleavage are more potent in increasing serum growth hormone levels when administered i.v. due to longer stability in vivo. DPP-IV inhibition would be predicted to increase GHRH levels and thus serum growth hormone levels. Therefore, the compounds of the present invention, including but not limited to those specified in the examples can be used in the treatment of conditions associated with deficiency in growth hormone including metabolic disorders (central obesity, dyslipidemia), osteoporosis and frailty of aging.

Diabetic dyslipidemia is characterized by multiple lipoprotein defects including moderately high serum levels of cholesterol and triglycerides, small LDL particles and low levels of HDL cholesterol. The dyslipidemia associated with non-insulin-dependent diabetes mellitus is improved in conjunction with improved diabetic condition following treatment with GLP-1 (Junti-Berggren, et al., *Diabetes Care* 1996, 19, 1200–6). DPP-IV inhibition is predicted to increase the level of circulating GLP-1 (7-36) amide and thereby would be effective in the treatment of diabetic dyslipidemia and associated complications. Therefore, the compounds of the present invention, including but not limited to those specified in the examples can be used in the treatment hypercholesterolemia, hypertriglyceridemia and associated cardiovascular disease.

Parenteral injection of GLP-1 (7-36) amide in healthy men, obese men or patients with non-insulin-dependent diabetes mellitus has been reported to promote satiety and to suppress food intake (Flint, et al., *J. Clin. Invest.* 1998, 101, 515–520; Naslund, et al., *Am. J. Clin. Nutr.* 1998, 68, 525–530; Gutzwiller et al., *Am. J. Physiol.* 1999, 276, R1541–R1544.) DPP-IV inhibition is predicted to increase the level of circulating GLP-1 (7-36) amide and thereby increases satiety in obesity and non-insulin-dependent diabetes mellitus. Therefore, the compounds of the present invention, including but not limited to those specified in the examples can be used in the treatment of obesity.

For the treatment of obesity, compounds of the present invention may be used alone, or in combination with any existing anti-obesity agent as described by Flint, A.; Raben, A.; Astrup, A.; Holst, J. J. in *J. Clin. Invest* 1998,101, 515–520 or by Toft-Nielsen, M.-B.; Madsbad, S.; Holst, J. J. in *Diabetes Care* 1999, 22, 1137–1143. Agents which may be used in combination with the compounds of the present invention include, but are not limited to fatty acid uptake inhibitors such as orlistat and the like, monoamine reuptake inhibitors such as sibutramine and the like, anorectic agents such as dexfenfluramine, bromocryptine, and the like, sympathomimetics such as phentermine, phendimetrazine, mazindol, and the like, thyromimetic agents, or other such anti-obesity agents that are known to one skilled in the art.

DPP-IV is expressed on a fraction of resting T cells at low density but is strongly upregulated following T-cell activation. DPP-IV may have important fuctions on T cells and in the immune system. Synthetic inhibitors of the enzymatic activity of CD26 have been shown to suppress certain immune reactions in vitro and in vivo. In vitro recombinant soluble DPP-IV enhances proliferative responses of peripheral blood lymphocytes to stimulationwith soluble tetanus toxoid antigen. In addition, the enhancing effect requires DPP-IV enzyme activity (Tanaka, et al., *Proc. Natl. Acad. Sci.* 1994, 91, 3082–86; Tanaka, et al., *Proc. Natl. Acad. Sci.* 1993, 90, 4583). Soluble DPP-IV up-regulates the expression of the costimulatorymolecule CD86 on monocytes through its dipeptidyl peptidase IV activity suggesting that soluble DPP-IV enhances T cell immune response to recall antigen via its direct effect on antigen presenting cells (Ohnuma, et al., *J. Immunol.* 2001, 167(12), 6745–55). Consequently, DPP-IV inhibition would be predicted to suppress certain immune responses and thus have therapeutic benefit in the treatment of immunomodulatory diseases. Therefore, the compounds of the present invention, including but not limited to those specified in the examples can be used in the treatment of rheumatoid arthritis, multiple sclerosis, scleraderma, chronic inflammatory bowel disease or syndrome and allograft rejection in transplantation.

In addition to GLP-1, enteroendocrine L cells secrete glucagon-like peptide 2 (GLP-2) in response to food intake. GLP-2 has trophic effects on intestinal epithelium and has been demonstrated to promote nutrient absorption in rodents (Drucker, D J in *Gastroenterology* 2002, 122, 531–544) and to promote intestinal mucosal wound healing (Bulut, K., et. al., in *Regulatory Peptides*, 2004, 121, 137–143). GLP-2 is a likely in vivo substrate for DPP-IV and inhibitors of DPP-IV are predicted to potentiate the action of endogenous GLP-2. Therefore, the compounds of the present invention, including but not limited to those specified in the examples can be used in the treatment of inflammatory bowel syndrome, Crohn's disease and short bowel disease and other malabsorption disorders.

Chemokine receptors, especially CCR5 and CXCR4, act as cofactors for HIV-1 entry into CD4+ cells and their corresponding ligands can suppress HIV entry and thus replication. The CXC chemokine, stromal cell derived factor-1 (SDF-1) is a chemokine for resting T-lymphocytes and monocytes. SDF-1 exists as two splice variants, SDF-1alpha and SDF-1beta that differ by four additional C-terminal residues in SDF-1beta. Truncation of the N-terminal Lys-Pro- residues from both SDF-1 alpha and SDF-1 beta results in the loss of their chemotactic and antiviral activities in vitro (Ohtsuki, et al, *FEBS Lett.* 1998, 431, 236–40; Shioda, et al., *Proc. Natl. Acad. Sci.* 1998, 95(11), 6331–6; Proost, et al., *FEBS Lett.* 1998, 432, 73–6). DPP-IV inactivates SDF-1 alpha as a ligand for CXCR4 that is a T cell chemotactic receptor as well as the major co-receptor for T-tropic HIV-1 strains. DPP-IV inhibition would be predicted to increase full-length SDF-1 levels and thereby suppress HIV-1 entry into $CXCR_4+$ cells. Therefore, the compounds of the present invention, including but not limitd to those specified in the examples can be used in the treatment of HIV infection (AIDS).

DPP-IV inhibition may be useful in hematopoeitic stem cell (HSC) transplantation (Christopherson, K W, et.al., in *Science,* 2004, 305, 1000–10002). Expression of DPP-IV on the surface of HSC decreases homing and engraftment to bone marrow niches. DPP-IV inhibition greatly increases the efficiency of transplantation. Therefore, the compounds of the present invention, including but not limited to those specified in the examples can be used to improve bone marrow transplant efficiency.

Mice deficient in GLP-1 receptor signaling have learning deficits and increased neural injury after kainite administration (During, M J, et. al., in Nature Medicine, 2003, 9, 1173–1179). In contrast, GLP-1 receptor agonists prevent kainite-induced neuronal apoptosis in normal animals. DPP-1V inhibitors would be predicted to increase active GLP-1 and show similar effects. Therefore, the compounds of the present invention, including but not limited to those specified in the examples can be used for the treatment of Alzheimer's Disease and other neurodegenerative and cognitive disorders.

Synthetic Methods

The compounds and processes of the present invention will be better understood in connection with the following synthetic schemes that together illustrate the methods by which the compounds of the invention may be prepared. The synthesis of compounds of formula (I) wherein the groups $R_1$ and $R_2$ are as defined above unless otherwise noted below, are exemplified below.

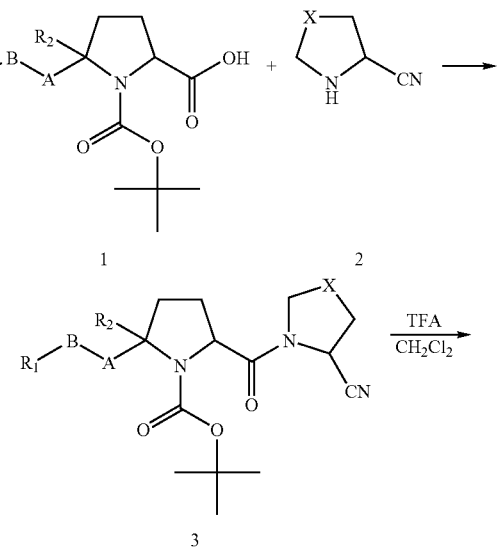

Scheme 1

-continued

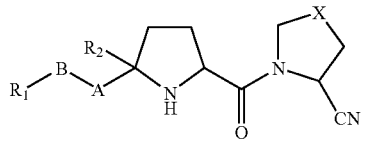

4

As shown in Scheme 1, compounds of the general formula 1, which may either be purchased directly or may be obtained by modifying commercially available starting material through methods commonly known to those skilled in the art, may be treated with compounds of general formula 2 along with reagents such as but not limited to benzotriazol-1-yl-oxy-tris-pyrrolidino-phosphonium-hexafluorophosphate (PyBOP), 1-(3-(dimethylamino)propyl)-3-ethylcarbodiimide hydrochloride (EDCI), 2-(1H-benzotriazol-1yl)-1,1,3,3-tetramethyluronium tetrafluoroborate (TBTU) in the presence of a base such as but not limited to N methylmorpholine or diisopropylethylamine in solvents such as but not limited to dichloromethane to provide compounds of general formula 3. Compounds of formula 3 may be treated trifluoroacetic acid in dichloromethane or with reagents known to deprotect the nitrogen protecting group as known to those skilled in the art or demonstrated in Greene, T. W. and Wuts, G. M. "Protective groups in Organic Synthesis", third ed. John Wiley & Sons, 1999, to provide compounds of general formula 4, which are representative of compounds of formula (I).

Scheme 2

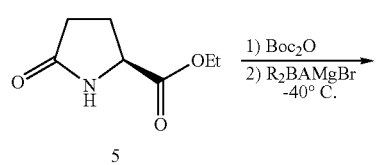

5

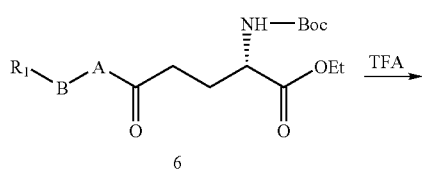

6

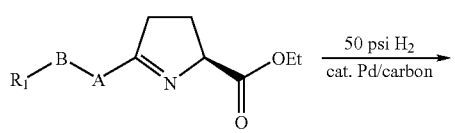

7

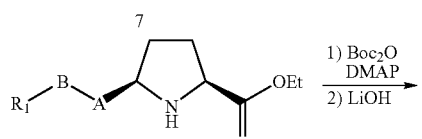

8

-continued

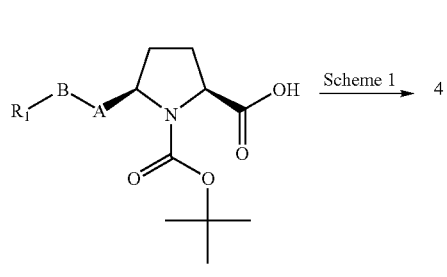

9

As shown in Scheme 2, ethyl (S)-(+)-2-pyrrolidone-5-carboxylate 5 can be treated with di-tert-butyl dicarbonate ((Boc)$_2$O) in solvents such as but not limited to THF, dioxane or acetonitrile followed by treatment with Grignard reagents of general formula R$_1$BAMgBr, wherein R$_1$, B and A are as defined in formula (I) in solvents such as but not limited to THF and diethyl ether to provide compounds of general formula 6. The treatment of compounds of general formula 6 with reagents that deprotect a nitrogen protecting group such as the removal of the Boc protecting group with TFA will provide compounds of general formula 7. The treatment of compounds of general formula 7 under conditions of 50 psi of hydrogen in the presence of a palladium catalyst such as 10% palladium on carbon with provide compounds of general formula 8. The protection of the nitrogen of compounds of general formula 8 using di-tert-butyl dicarbonate ((Boc)$_2$0) and a catalytic amount of DMAP in solvents such as but not limited to THF, dioxane or acetonitrile followed by the hydrolysis of the ester group using reagents such as but not limited to lithium hydroxide or sodium hydroxide in solvents such as aqueous ethanol or aqueous dioxane will provide compounds of general formula 9. The treatment of compounds of general formula 9 according to the conditions described in Scheme 1 outlining the coupling and deprotection will provide compounds of general formula 4, which are representative of compounds of the present invention.

Scheme 3

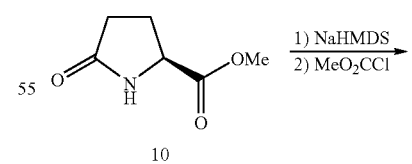

10

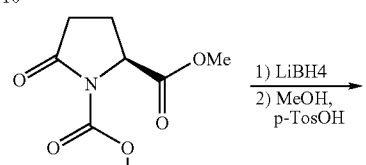

11

-continued

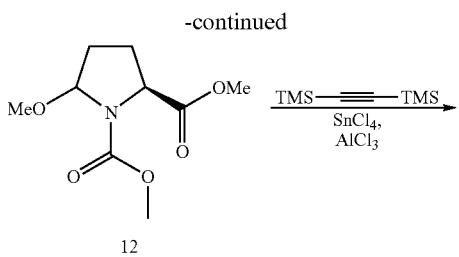

12

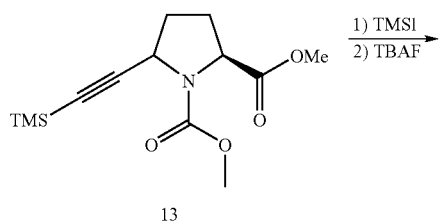

13

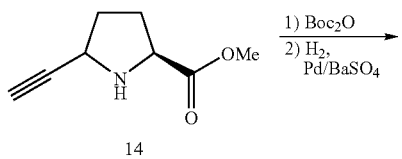

14

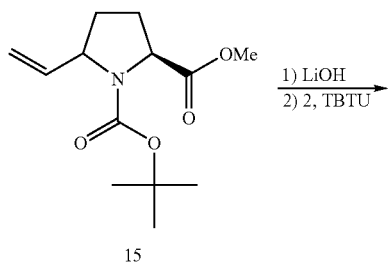

15

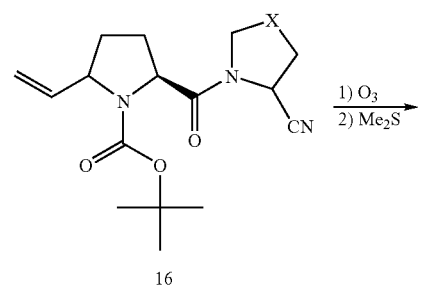

16

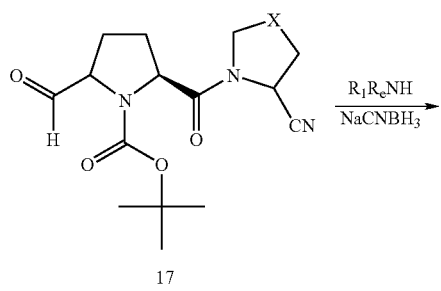

17

-continued

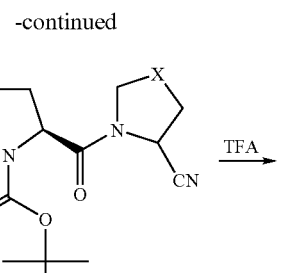

18

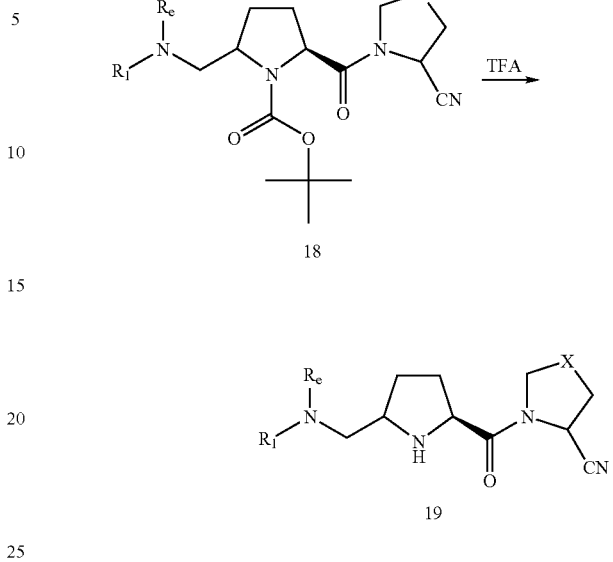

19

As shown in Scheme 3, compounds of general formula 10 when treated first with sodium bis(trimethylsilyl)amide followed by treatment with chloroformate such as but not limited to methyl chloroformate in solvents such as but not limited to THF will provide compounds of general formula 11. Compounds of general formula 11 when first treated with a reducing agent such as but not limited to lithium borohydride in THF followed by the treatment with methanol and p-toluene sulfonic acid under heated conditions will provide compounds of general formula 12. Compounds of general formula 12 when treated with bis(trimethylsilyl)acetylene, tin (IV) chloride and aluminum chloride in solvents such as toluene and the like to provide compounds of general formula 13. Compounds of general formula 13 when treated with iodotrimethylsilane to remove the methoxycarbonyl protecting group followed by treatment with tetrabutylammonium fluoride to remove the silyl group will provide compounds of general formula 14. The nitrogen of compounds of general formula 14 can be protected by treatment with di-tert-butyl dicarbonate and a catalytic amount of DMAP in solvents such as but not limited to THF and the acetylene group can be converted to an alkene by treatment under an atmosphere of hydrogen in the presence of 5% palladium on barium sulfate in solvent such as but not limited to THF to provide compounds of general formula 15. The hydrolysis of the ester of compounds of general formula 15 by treatment with lithium hydroxide in solvents such as aqueous methanol followed by treatment with compound of general formula 2 according to the conditions outlined in Scheme 1 to provide compounds of general formula 16. Compounds of general formula 16 can be treated first with ozone followed by treatment with methyl sulfide to provide compounds of general formula 17. The aldehyde functionality of compound of formula 17 can be treated with a primary or secondary amine such as $R_1R_eNH$ and sodium cyanoborohydride in solvents such as but not limited to THF to provide compound of general formula 18 wherein $R_1$ and $R_e$ are as defined in formula (I). Compounds of formula 18 can then be treated with trifluoroacetic acid to remove the Boc group to provide compound of general formula 19 which are representative of compounds of the present invention.

Scheme 4

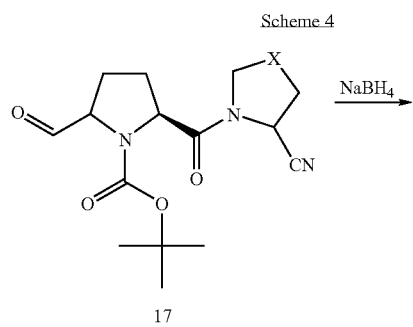
17

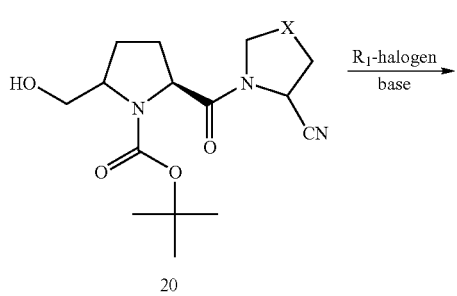
20

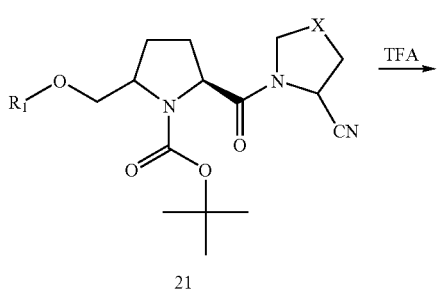
21

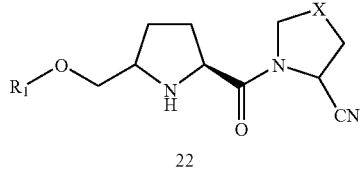
22

Scheme 4a

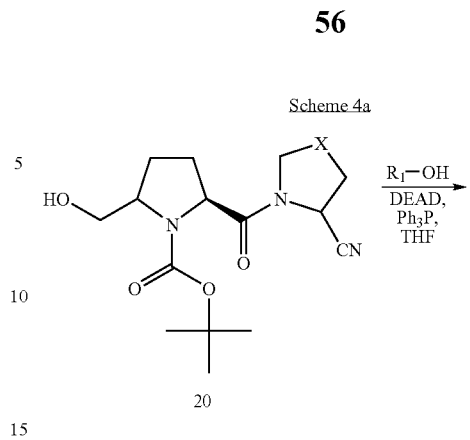
20

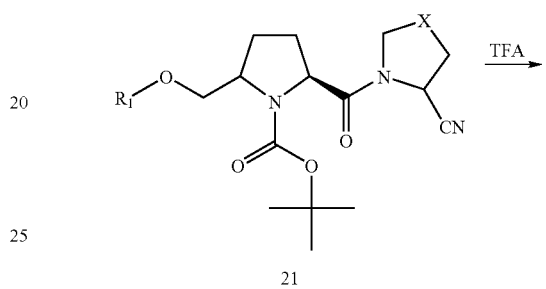
21

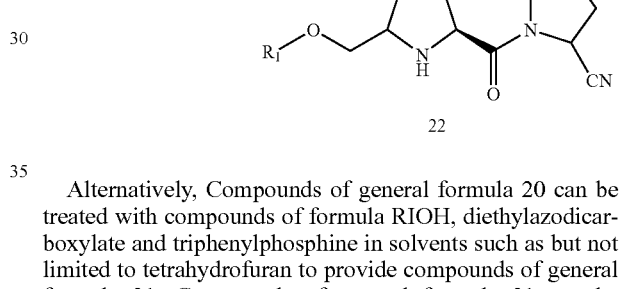
22

Alternatively, Compounds of general formula 20 can be treated with compounds of formula RIOH, diethylazodicarboxylate and triphenylphosphine in solvents such as but not limited to tetrahydrofuran to provide compounds of general formula 21. Compounds of general formula 21 can be converted into compounds of general formula 22 using conditions described in Scheme 4.

Scheme 5

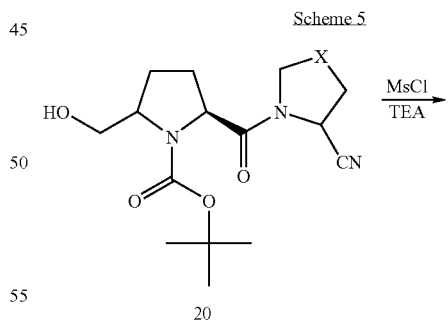
20

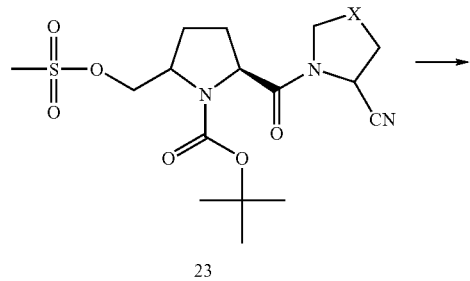
23

As shown in Scheme 4, compounds of general formula 17 which were described in Scheme 3, can be treated with sodium borohydride in solvents such as but not limited to THF and dioxane to provide compounds of general formula 20. Compounds of general formula 20 can be treated with compounds of general formula $R_1$-halogen and a base, wherein $R_1$ is alkyl, alkylcarbonyl, arylalkyl, arylcarbonyl, cycloalkylalkyl, heterocyclealkyl, heterocyclecarbonyl and hydroxyalkyl and halogen is chloro, bromo, or iodo to provide compounds of general formula 21. Typical bases for this transformation include but are not limited to triethylamine, diisopropylethylamine, sodium methoxide, sodium hydride but may include others depending upon $R_2$-halogen or as known to those skilled in the art. The transformation of compounds of general formula 21 to compounds of general formula 22 can be accomplished using trifluoroacetic acid or other methods known to remove Boc protecting groups from nitrogen atoms.

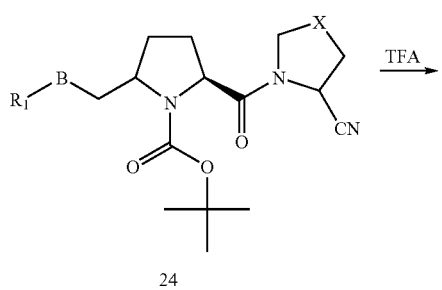

24

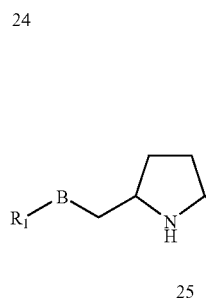

25

Alternatively, compounds of general formula 20 may be converted to a mesylate of general formula 23 upon treatment of compounds of formula 20 with methanesulfonyl chloride and triethylamine in dichloromethane. Mesylates of general formula 23 when treated with a nucleophile $R_1$-BH, which may be a heterocycle or aryl or heteroaryl or other group, will provide a compound of general formula 24. Typical conditions for this reaction include but are not limited to the treatment of compounds of general formula 23 with a nucleophile and a base such as sodium hydride in tetrahydrofuran or cesium carbonate in DMF will provide compounds of general formula 24. Alternatively, nucleophiles may also be treated with sodium hydride in tetrahydrofuran followed by treatment with compounds of general formula 23 to provide compounds of general formula 24. The conversion of compounds of general formula 24 to compounds of general formula 25 can be effected through conditions described above or are known to those skilled in the art.

Scheme 6

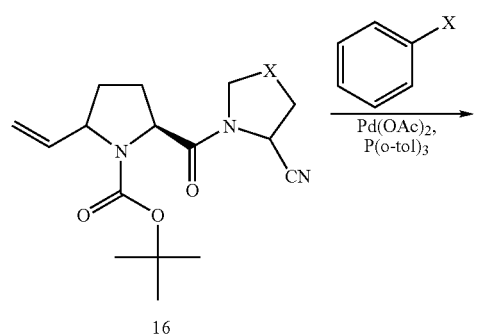

16

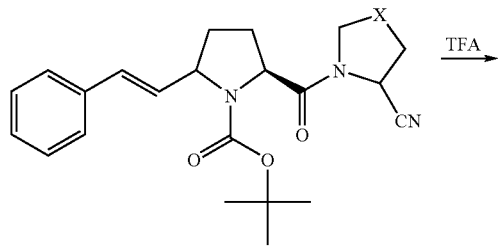

26

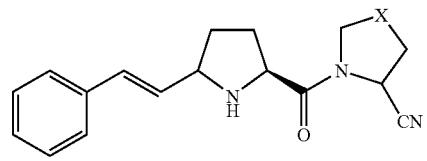

27

Compounds of general formula 16 which can be obtained as described in Scheme 3 can be treated with arylhalides, palladium acetate and tri-ortho-tolylphosphine in solvents such as but not limited to THF to provide compounds of general formula 26. Compounds of general formula 26 can be converted to compounds of general formula 27 through methods described above or through methods known to those skilled in the art for removing a Boc protecting group from a nitrogen.

Scheme 7

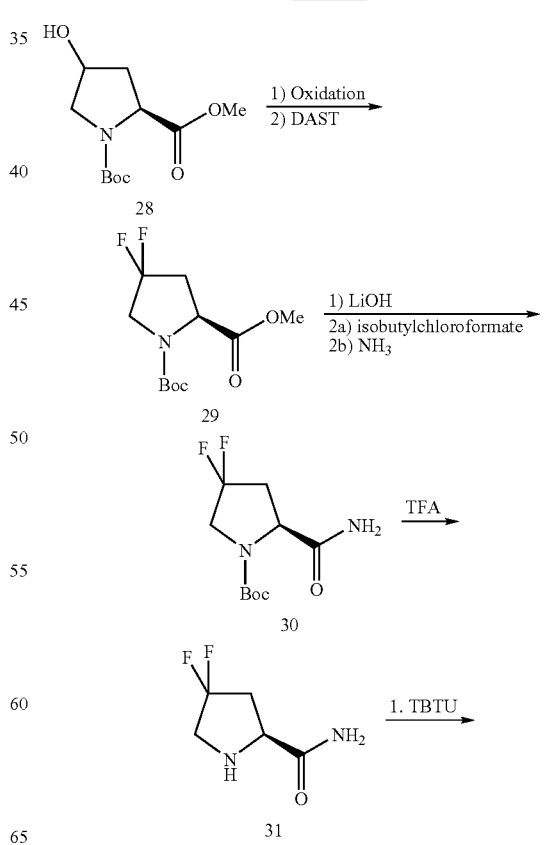

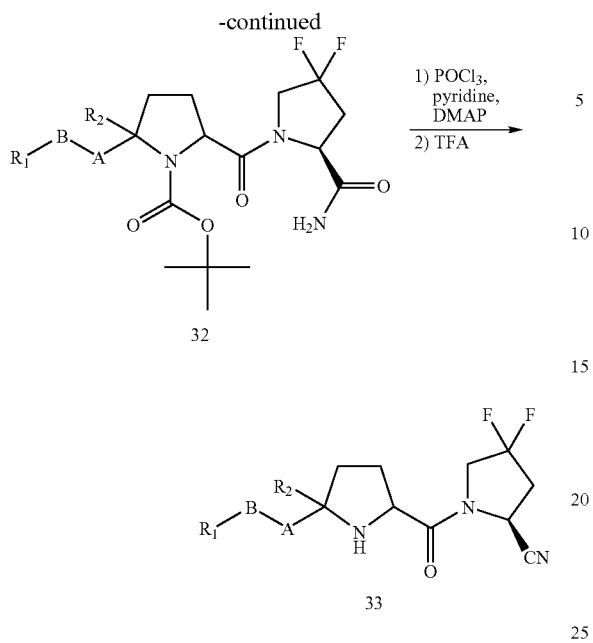

32

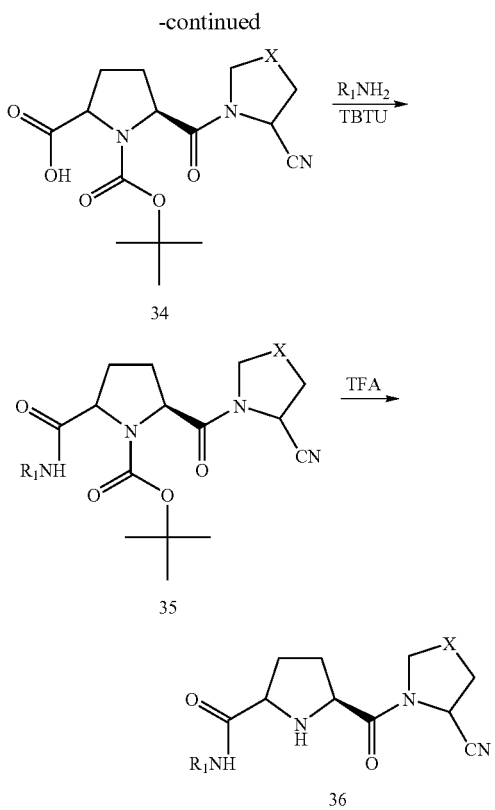

34

35

36

As shown in Scheme 7, compounds of general formula 28 can be oxidized through conditions such as but not limited to oxalyl chloride, DMSO and triethyl amine; pyridinium chlorochromate; pyridinium dichromate and the like followed the treatment with (diethylamino)sulfur trifluoride (DAST) to provide compounds of general formula 29. The ester functionality of compounds of general formula 29 can be hydrolyzed upon treatment with lithium hydroxide in aqueous methanol or through methods know to those skilled in the art, followed by first treatment with isobutyl chloroformate followed by addition of aqueous ammonia to the reaction mixture to provide compounds of general formula 30. Compounds of general formula 30 can be treated with trifluoroacetic acid to remove the Boc protecting group to provide compounds of general formula 31. Compounds of general formula 31 can be treated with compounds of general formula 1 and TBTU to provide compounds of general formula 32.

Compounds of general formula 32 can be treated with phosphorous oxychloride, pyridine and DMAP followed by treatment with trifluoroacetic acid to provide compounds of general formula 33.

Additionally, compounds of general formula 17 can be treated with reagents such as but not limited to KMnO4 to provide compounds of general formula 34. The acid functionality of compounds of general formula 34 can be activated with TBTU in the presence of an amine of formula $R_1NH_2$ to provide compounds of general formula 35. Compounds of general formula 35 can be treated with TFA to provide compounds of general formula 36.

Scheme 8

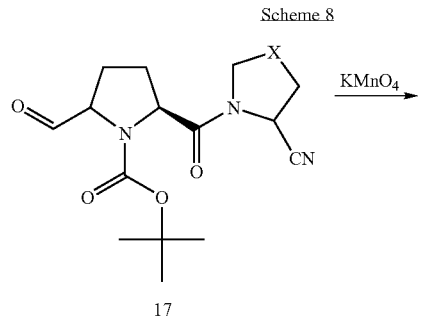

17

Scheme 9

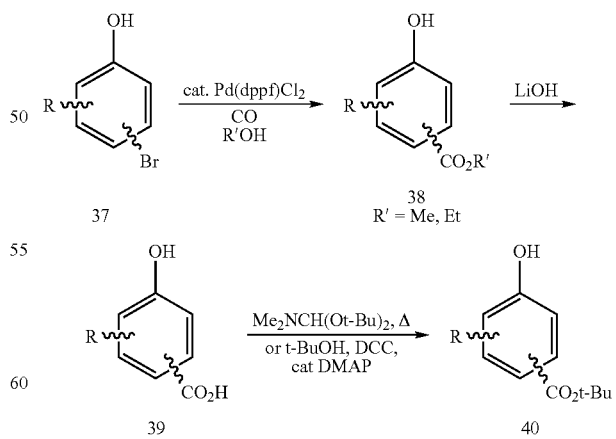

As shown in Scheme 9, the required tert-butyl ester phenol of general formula 40 can be synthesized form bromophenols of general formula 37. Bromophenols 37 can be carbonylated under carbon monoxide atmosphere in the presence of proper palladium catalyst. The resulting esters 38 can be hydrolyzed with proper base such as LiOH to afford the corresponding acids 39. Acids 39 can be treated with either N,N-dimethylformaldehyde di(tert-butyl)acetal or a proper coupling reagent such as DCC to afford tert-butyl ester phenol 40.

Scheme 10

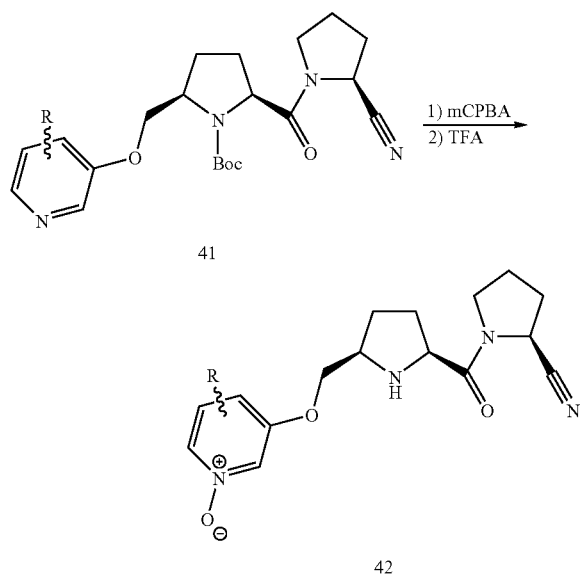

As shown in Scheme 10, the nitrogen atom of the pyridinyl group in general structure 41 can be oxidized with a proper reagent such as meta-chloroperoxybenzoic acid (mCPBA). Removal of the Boc group with a proper reagent such as trifluoroacetic acid (TFA) affords the desired N-oxides of general structure 42.

The compounds and processes of the present invention will be better understood by reference to the following examples, which are intended as an illustration of and not a limitation upon the scope of the invention. Further, all citations herein are incorporated by reference.

Compounds of the invention were named by ACD/ChemSketch version 5.01 (developed by Advanced Chemistry Development, Inc., Toronto, ON, Canada) or were given names consistent with ACD nomenclature.

Experimentals

EXAMPLE 1

(2S)-1-((5S)-5-ethyl-L-prolyl)pyrrolidine-2-carbonitrile

EXAMPLE 1A 2S-tert-butoxycarbonylamino-5-oxo-heptanoic acid ethyl ester

Ethyl N-Boc (S)-pyroglutamate (2.33 g, 9.06 mmol) prepared as described by: (a) St-Denis, Y,; Augelli-Szafran, C. E.; Bachand, B.; Berryman, K. A.; DiMaio, J.; Doherty, A. M.;Edmunds, J. J.;Leblond, L.; Levesque, S.; Narasimhan, L. S.; Penvose-Yi, J. R.; Rubin, J. R.; Tarazi, M.; Winocour, P. D.; Siddiqui, M. A. *Biorg. Med. Chem. Lett.* 1998, 8, 3193–3198. (b) Jain, R. *Org. Prep. Procd. Intl.* 2001, 33, 405–409; was dissolved in 6 mL of THF, and the mixture was cooled to −40° C. Ethyl magnesium bromide solution (1.0 M in THF, 10.84 mL, 10.84 mmol) was added slowly via syringe. After 2 hours, the reaction flask was placed in a freezer (approx −20° C.) overnight. Saturated aqueous NH$_4$Cl and 1 N HCl were added, and the mixture was extracted with ethyl acetate (3×). The combined organic extracts were dried over Na$_2$SO$_4$, concentrated and purified by flash chromatography (30% ethyl acetate/hexane) to provide the titled compound (2.018 g, 78%). MS (ESI) m/z 288 (M+H)+, 310 (M+Na)$^+$.

EXAMPLE 1B 5-ethyl-3,4dihydro-2H-pyrrole-(2S)-carboxylic acid ethyl ester

The ester from Example 1A was dissolved in 3 mL of CH$_2$Cl$_2$ and treated with 3 mL of trifluoroacetic acid at room temperature. After 3 hours, the volatiles were evaporated to provide the titled compound. MS (ESI) nl/z 170 (M+H)$^+$.

EXAMPLE 1C 5S-ethyl-pyrrolidine-2S-carboxylic acid ethyl ester

The material from Example 1B was dissolved in 32 mL of EtOH and mixed with 0.30 g of 10% Pd/C under 60 psi of H$_2$ overnight. The catalyst was removed by filtration, and the filtrate was concentrated to provide the titled compound. MS (CI) m/z=172 (M+H)$^+$.

EXAMPLE 1D

5S-Ethyl-pyrrolidine-1,2S-dicarboxylic acid 1-tert-butyl ester 2-ethyl ester

The material from Example 1C (18.08 mmol), 4(dimethylamino)pyridine (0.904 mmol) and triethylamine (36.16 mmol) were mixed in 40 mL of CH$_2$Cl$_2$, and then di-tert-butyl dicarbonate (19.89 mmol) was added. After stirring overnight, the mixture was washed with 1 N HCl and brine, and then purified by flash column chromatography (15–20% ethyl acetate/hexane) to provide the titled compound (3.73 g, overall 80%). MS (ESI) m/z 258(M+H)$^+$. $(\alpha)^{20}{}_D$=−35.860 (c 1.45, MeOH).

EXAMPLE 1E

5S-Ethyl-pyrrolidine-1,2S-dicarboxylic acid 1-tert-butyl ester

The material from Example 1D (3.69 g, 14.34 mmol) in 15 mL of EtOH was treated with 14.3 mL of 1.7 N LiOH. After 4 hours, the mixture was concentratedin vacuo, acidified with 1N HCl and extracted with ethyl acetate. The organic extracts were dried with Na$_2$SO$_4$ and concentrated to provide the title compound which was used without further purification in the next step.

EXAMPLE 1F 2S-(2S-Cyano-pyrrolidine-1-carbonyl)-5S-ethyl-pyrrolidine-1-carboxylic acid tert-butyl ester The material prepared in Example 1E (201 mg, 0.88 mmol), 2S-cyanopyrrolidine hydrochloride (1.1 mol) and PyBOP (641 mg, 1.23 mmol) were mixed in 3.5 mL of $CH_2Cl_2$ followed by addition of 422 µL of diisopropylethylamine (2.42 mmol). After 5 hours, acetonitrile (MeCN) (3 mL) was added and the mixture was purified by reverse-phase HPLC (50 mg of crude material dissolved in MeCN/MeOH was injected into a Waters C18 column (7 micron, 25×100 mm) and eluted using a linear gradient of 5% to 100% $CH_3CN/H_2O$). The aqueous phase contained 10 mM $NH_4OAc$. Fraction collection was trigered by UV absorption at 210 nm.) to provide 187 mg of title compound (69%).

EXAMPLE 1G (2S)-1-((5S)-5-ethyl-L-prolyl)pyrrolidine-2-carbonitrile

The sample of Example 1F (180 mg) dissolved in 1 mL of $CH_2Cl_2$ was treated with 1.5 mL of TFA. After 4 hours, the mixture was concentrated and the residue dissolved in 3 mL of MeOH, then purified by reverse-phase HPLC (0% to 70% $CH_3CN/H_2O$ contained 0.1% TFA.) to provide the title compound as the corresponding trifluoroacetic acid salt (147 mg). $^1H$ NMR (400 MHz, MeOH-$d_4$,) δ 1.07 (t, J=7.5 Hz, 3H), 1.70–1.82 (m, 2H), 1.95 (m, 1H), 2.10–2.38 (m, 6H), 2.52 (m, 1H), 3.60 (m, 1H), 3.64 (dd, $J_1=J_2=6.8$ Hz, 2H), 4.62(dd, J=5.4, 9.4 Hz, 1H), 4.82 (dd, J=4.3, 8.0 Hz, 1H) ppm. $^{13}C$ NMR (MeOH-$d_4$, 100 MHz)δ 11.2, 25.8, 26.1, 28.9, 30.0, 30.8, 47.6, 48.2, 60.3, 64.3, 119.2, 168.9 ppm. MS (ESI) m/z 222 (M+H)$^+$.

EXAMPLE 2

(2S)-1-((5R)-5-phenyl-L-prolyl)pyrrolidine-2-carbonitrile

The title compound was synthesized by substituting 5S-ethyl-N-Boc-2S-proline in Example 1 with 5R-phenyl-N-Boc-2S-proline. $^1H$ NMR (MeOH-d4, 500 MHz) δ 2.29 (m, 6H) 2.48 (m, 1H) 2.64 (m, 1H) 3.69 (m, 2H) 4.74 (m, 2H) 4.86 (dd, J=7.80, 4.37 Hz, 1H) 7.48 (m, 3H) 7.61 (m, 2H) ppm. MS (ESI) m/z 270 (M+H)$^+$.

EXAMPLE 3

(2S)-4,4-difluoro-1-((5!)-5-methyl-L-prolyl)pyrrolidine-2-carbonitrile

EXAMPLE 3A

4-Oxo-pyrrolidine-1,2S-dicarboxylic acid 1-tert-butyl ester 2-methyl ester

Oxalyl chloride (1.30 mL, 14.96 mmol) was added to 10 mL of $CH_2Cl_2$ and cooled to −78° C. DMSO (1.33 mL, 18.70 mmol) was added via syringe. After 5 minutes, 4R-hydroxy-pyrrolidine-1,2S-dicarboxylic acid 1-tert-butyl ester 2-methyl ester (1.83 g, 7.48 mmol) in 12 mL of $CH_2Cl_2$ was added. After 30 minutes, $Et_3N$ (3.64 mL) was added. The mixture was stirred at −78° C. for 40 minutes, then at 0° C. for 30 minutes. The mixture was diluted with $CH_2Cl_2$ (ca. 30 mL) and 1N HCl was added. The organic layer was washed with brine, dried with $Na_2SO_4$ and concentrated to provide the titled compound (2.20 g). MS (CI) m/z 244 (M+H)$^+$.

EXAMPLE 3B 4,4-Difluoro-pyrrolidine-1,2-dicarboxylic acid 1-tert-butyl ester 2-methyl ester The compound from Example 3A (2.20 g) in 15 mL of $CH_2Cl_2$ was cooled to −50° C., then $Et_2NSF_3$ (2.47 mL, 18.7 mmol) was added. After 10 minutes, the cooling bath was removed, and the mixture was stirred overnight. $NaHCO_3$ solution was added slowly to the mixture and the mixture was extracted with dichloromethane (3×). The combined organics were dried with $Na_2SO_4$ and purified with flash chromatography (10% ethyl acetate/hexane) to provide the difluoroester (1.81 g, 91%). MS (CI) m/z 266 (M+H)$^+$.

EXAMPLE 3C 4,4-Difluoro-pyrrolidine-1,2S-dicarboxylic acid 1-tert-butyl ester The compound from Example 3B (1.80 g, 6.78 mmol) was dissolved in 3 mL each of MeOH and THF, then 6.8 mL of 1.7 N LiOH was added. After stirring for 2 hours, the mixture was concentrated in vacuo, and ethyl acetate and 1N HCl were added. The organic extracts were dried with $Na_2SO_4$ and concentrated to provide the crude acid (1.82 g).

EXAMPLE 3D

2S-Carbamoyl-4,4-difluoro-pyrrolidine-1-carboxylic acid tert-butyl ester

The compound from Example 3C and triethylamine (1.7 mL) were mixed with 15 mL of THF and cooled to 0° C. Isobutyl chloroformate (1.14 mL) was added via syringe. After 30 minutes, 27.1 mL of 0.5 N $NH_3$ in dioxane were added. After stirring overnight, the mixture was concentrated in vacuo and extracted with ethyl acetate. The combined organic extracts were dried with $Na_2SO_4$, concentrated and purified by flash chromatography (70% ethyl acetate/hexane) to provide the title amide (0.82 g, 48%). MS (ESI) m/z 251 (M+H)$^+$.

EXAMPLE 3E 4,4-Difluoro-pyrrolidine-2S-carboxylic acid amide

The compound from Example 3D (802 mg, 3.2 mmol) in 1.5 mL of $CH_2Cl_2$ was treated with 2.0 mL of TFA. After 4 hours, the mixture was concentrated to provide the crude amino amide (1.05g).

EXAMPLE 3F 2S-(2S-Carbamoyl-4,4-difluoro-pyrrolidine-1-carbonyl)-5S-methyl-pyrrolidine-1-carboxylic acid tert-butyl ester The compound from Example 3E (303 mg, 0.93 mmol), 5-methyl-pyrrolidine-1,2S-dicarboxylic acid 1-tert-butyl ester (1eq, prepared as described in Example 5) and 2-(1H-benzotriazole-1-yl)-1, 1,3,3-tetramethyluronium tetrafluoroborate (TBTU, 1.4 eq.) were mixed in 2 mL of DMF, then Et₃N was added until the pH of the mixture reached 67 (wet pH paper). The mixture was stirred overnight and purified by reverse-phase HPLC to provide the titled compound. (170 mg, 56%).

EXAMPLE 3G 2S-(2S-Cyano-4,4-difluoro-pyrrolidine-1-carbonyl)-5S-methyl-pyrrolidine-1-carboxylic acid tert-butyl ester The compound of Example 3F (160 mg, 0.44 mmol) and imidazole (1.25 eq.) were mixed in 3 mL of pyridine and cooled to −30° C., then POC13 (2.5 eq.) was added via syringe. The mixture was then placed in a freezer (−20° C.) overnight. Saturated NH₄Cl solution was added, and the mixture was concentrated in vacuo. The mixture was taken up in ethyl acetate and washed with 1N HCl and then brine. The organic layer was dried with Na₂SO₄ and concentrated to provide the title compound (147 mg).

EXAMPLE 3H (2S)-4,4-difluoro-1-((5S)-5-methyl-L-prolyl)pyrrolidine-2-carbonitrile The Boc group of Example 3G was removed as described in Example 1G to provide the title compound. $^1$H NMR (500 MHz, MeOH-d₄) δ 1.48 (d, J=6.5 Hz, 3H), 1.78 (dq, J=8.7, 13.8 Hz, 1H), 2.10 (m, 1H), 2.25(m, 1H), 2.65 (m, 1H), 2.80–2.95 (m, 2H), 3.78 (m, 1H), 4.10 (m, 1H), 4.58 (dd, J=6.2, 12.0 Hz), 5.14 (dd, J=4.5, 9.2 Hz) ppm. $^{13}$C NMR (MeOH-d₄, 100 MHz) δ 17.0, 28.8, 32.0, 37.8 (t, J=25.4 Hz), 46.1, 53.2 (t, J=32.6 Hz), 58.6, 60.3, 117.7, 127.0 (t, J=249 Hz), 169.3 ppm. MS (ESI) m/z 244 (M+H)⁺.

EXAMPLE 4

3-{(((2S,5S)-5-methylpyrrolidin-2-yl)carbonyl}-1,3-thiazolidine

The title compound was synthesized by substituting 2S-cyanopyrrolidine in Example 1 with thiazolidine and using the methyl pyrrolidine prepared as described in Example 5. $^1$H NMR (500 MHz, MeOH-d₄) δ 1.48 (d, J=6.55 Hz, 3H) 1.73 (m, 1H) 2.13 (m, 1H) 2.24 (m, 1H), 2.51 (m, 1H) 3.09 (m, 1H) 3.16 (m, 1H) 3.75 (m, 2H) 3.88 (m, 1H) 4.52 (m, 1H) 4.61 (dd, J=9.51, 5.77 Hz) and 4.67 (m, 2H) ppm. MS (ESI) m/z 201 (M+H)⁺.

EXAMPLE 5

(2S)-1-((5S)-5-methyl-L-prolyl)pyrrolidine-2-carbonitrile

The title compound was synthesized by substituting EtMgBr in Example 1 with MeMgBr. $^1$H NMR (MeOH-d₄, 400 MHz) δ 1.49 (d, J=6.75 Hz, 3H), 1.75 (dq, J=13.08, 8.84 Hz, 1H), 2.16 (m, 3H), 2.28 (m, 3H), 2.54 (m, 1H), 3.64 (t, J=6.60 Hz, 2H), 3.80 (m, 1H), 4.61 (dd, J=9.51, 5.83 Hz, 1H), 4.83 (dd, J=7.98, 4.30 Hz, 1H) ppm. $^{13}$C NMR (MeOH-d₄, 100 MHz) δ 17.0, 26.1, 29.1, 30.8, 32.1, 47.6, 48.2, 58.6, 60.6, 119.2, 168.9 ppm. MS (ESI), m/z 208(M+H)⁺.

EXAMPLE 6

(2S)-1-((5S)-5-ethyl-L-prolyl)-4,4-difluoropyrrolidine-2-carbonitrile

The title compound was synthesized by substituting 5S-methyl-N-Boc-2S-proline in Example 3 with 5S-ethyl-N-Boc-2S-proline prepared as described in Example 1. $^1$H NMR (400 MHz, MeOH-d₄) δ 0.79 (t, J=7.52 Hz, 3H), 1.49 (m, 2H), 1.66 (m, 1H), 1.81 (m, 1H), 2.01 (m, 1H), 2.23 (m, 1H), 2.60 (m, 2H), 3.30 (dt, J=16.88, 6.90 Hz, 1H), 3.83 (m, 2H), 4.34 (dd, J=9.36, 5.68 Hz, 1H), 4.86 (dd, J=9.21, 4.30 Hz, 1H) ppm. MS (ESI) m/z 258 (M+H)⁺.

EXAMPLE 7

(2S)-1-((5R)-5-ethyl-L-prolyl)pyrrolidine-2-carbonitrile

EXAMPLE 7A 5R-ethyl-pyrrolidine-1,2S-dicarboxylic acid 1-tert-butyl ester 2-methyl ester 5S-Vinyl-pyrrolidine-1,2S-dicarboxylic acid 1-tert-butyl ester 2-methyl ester (Example 22B, 1 g) and 10% Pd/C (200 mg) were stirred in ethanol (20 mL) under an atmosphere of hydrogen at room temperature for 16 hours. The catalyst was removed by filtration, and the filtrate concentrated under reduced pressure to provide the title compound (1 g, 99%). MS (DCI) m/z 258 (M+H)⁺.

EXAMPLE 7B (2S)-1-{(5S)-5-((4-bromophenoxy)methyl)-L-prolyl}pyrrolidine-2-carbonitrile The title compound was synthesized by substituting 5S-ethyl-pyrrolidine-1,2S-dicarboxylic acid 1-tert-butyl ester 2-ethyl ester in Example 1 with 5R-ethyl-pyrrolidine-1,2S-dicarboxylic acid 1-tert-butyl ester 2-methyl ester prepared in Example 7A. $^1$H NMR (300 MHz, MeOH-d₄) δ 2.03 (m, 10H) 2.64 (m, 1H) 3.64 (t,J=6.61 Hz, 2H) 4.55 (t,J=8.31 Hz, 1H) 4.83 (m, 1H), 0.92 (t, J=7.46, 3H) ppm. MS (ESI) m/z 222 (M+H)⁺.

EXAMPLE 8

(2S)-1-((5R)-5-isopropyl-L-prolyl)pyrrolidine-2-carbonitrile

The title compound was synthesized by substituting EtMgBr in Example 1 with i-PrMgBr. $^1$H NMR (400 MHz, MeOH-d4) δ 1.05 (d, J=6.75 Hz, 3H) 1.14 (d, J=6.75 Hz, 3H) 1.77 (m, 1H) 2.19 (m, 7H) 2.50 (m, 1H) 3.33 (m, 1H) 3.64 (t, J=6.75 Hz, 2H) 4.62 (dd, J=9.51, 5.22 Hz, 1H) 4.82 (dd, partially overlapped with solvent peak,J=4.60 Hz, 1H) ppm. MS (ESI) m/z 236 (M+H)⁺.

EXAMPLE 9

(2S)-1-((5R)-5-{((4-methoxyphenyl)amino)methyl}-L-prolyl)pyrrolidine-2-carbonitrile

EXAMPLE 9A dimethyl (2S)-5-oxopyrrolidine-1,2-dicarboxylate

In a procedure adapted from Li, H.; Sakamoto, T.; Kato, M.; Kikugawa, Y. *Synth. Commun.* 1995, 25(24), 4045–4052, to a cold (-78° C) solution of methyl (S)-(+)-2-pyrrolidone-5-carboxylate (4.80 grams, 33.5 mmol) in tetrahydrofuran (90 mL) was added a solution of lithium bis(trimethylsilyl) amide (1 M solution in hexanes, 40.0 mL, 40.0 mmol) dropwise via syringe over 15 minutes; then methyl chloroformate (2.90 mL, 36.9 mmol) was added dropwise via syringe over 5 minutes. The resulting slurry was stirred at −78° C. for 1 hour after which the reaction was quenched with 1 M HCl (50 mL). The mixture was allowed to come to room temperature, concentrated under reduced pressure and the residue partitioned between ethyl acetate (200 mL) and 1 M HCl (200 mL). The aqueous layer was extracted with ethyl acetate (2×200 mL), and the combined organic layers were dried (sodium sulfate), filtered, and concentrated to provide the titled compound (5.85 g, 86% yield). MS (DCI/NH$_3$) m/e 202 (M+H)$^+$; $^1$H NMR (300 MHz, CDCl$_3$): δ ppm 4.70 (dd, 1H), 3.88 (s, 3H), 3.80 (s, 3H), 2.72–2.30 (m, 3H), 2.15–2.05 (m, 1H).

EXAMPLE 9B dimethyl (2S)-5-methoxypyrrolidine-1,2-dicarboxylate

To a cold solution (−78° C.) of dimethyl (2S)-5-oxopyrrolidine-1,2-dicarboxylate (5.80 g, 28.8 mmol) in tetrahydrofuran (100 mL) was added a solution of lithium triethylborohydride (1 M in THF, 35 mL, 35 mmol) dropwise via syringe over 10 minutes. The resulting solution was stirred at −78° C. for 30 minutes and then quenched by the careful addition of saturated sodium bicarbonate solution (50 mL). After warming to 0° C., 30% hydrogen peroxide (6 mL) was carefully added dropwise. The mixture was stirred for 30 minutes at room temperature, concentrated under reduced pressure, and diluted with ethyl acetate (300 mL) and brine (200 mL). The milky aqueous layer was separated and further extracted with ethyl acetate (2×300 mL). The combined organic layers were dried (sodium sulfate), filtered, and concentrated to a light yellow oil. The yellow oil was taken up in methanol (50 mL) containing para-toluenesulfonic acid hydrate (487 mg, 2.6 mmol) and stirred at room temperature for 16 hours. The reaction was diluted with aqueous sodium bicarbonate solution (40 mL), the volatile solvents were removed under reduced pressure and the residue partitioned between ethyl acetate (200 mL) and brine (200 mL). The aqueous layer was further extracted with ethyl acetate (200 mL). The combined organic layers were dried (sodium sulfate), filtered, and concentrated to an oil which was purified by flash chromatography using 60% hexane/40% ethyl acetate as eluent to provide the titled compound (3.80 g, 61% yield) as a mixture of diastereomers. (mixture of amide bond rotomers) $^1$H NMR (300 MHz, CDCl$_3$): δ ppm 5.37 (d, 1H), 5.33 (dd, 1H), 5.24 (d, 1H), 5.18 (dd, 1H), 4.44–4.31 (m, 2H), 3.76 (s, 3H), 3.73 (s, 3H), 3.72 (s, 3H), 3.42 (s, 3H), 3.34 (s, 3H).

EXAMPLE 9C dimethyl (2S,5R)-5-((trimethylsilyl)ethynyl)pyrrolidine-1,2-dicarboxylate and dimethyl (2S,5S)-5-((trimethylsilyl)ethynyl)pyrrolidine-1,2-dicarboxylate Using a procedure adapted from Beal, L. M.; Liu,B.; Chu, W.; Moeller, K. D. *Tetrahedron* 2000, 56, 10113–10125, to a cold −45° C. solution of dimethyl (2S-5-methoxypyrrolidine-1,2-dicarboxylate (3.30 g, 15.20 mmol) and bistrimethylsilylacetylene (5.20 g, 30.4 mmol, 2.0 equiv) in methylene chloride (45 mL) was added a solution of tin (IV) chloride (1 M in methylene chloride, 20.0 mL, 20.0 mmol, 1.3 equiv) dropwise via syringe over 15 minutes. To the dark yellow solution was added solid aluminum chloride (2.77 g, 20.8 mmol, 1.4 equiv) in one portion. The resulting mixture was allowed to warm to room temperature and stirred at room temperature for 48 hours. The reaction mixture was carefully poured into aqueous sodium bicarbonate solution (100 mL) with ice cooling. A white precipitate forms and 1 M HCl (ca. 50 niL) was added until the solids dissolved. This mixture was extracted with ethyl acetate (2×200 mL). The combined organic layers were filtered, dried (sodium sulfate), filtered, and concentrated. The residue was purified by flash chromatography eluting with 70% hexane/30% ethyl acetate to afford 1.9 grams of (2S,5S)-5-((trimethylsilyl)ethynyl)pyrrolidine-1,2-dicarboxylate (trans compound Rf of 0.3 in 70% hexane/30% ethyl acetate) and 1.7 grams of dimethyl (2S,5R)-5-((trimethylsilyl)ethynyl)pyrrolidine-1,2-dicarboxylate (cis compound Rf of 0.2 in 70% hexane/30% ethyl acetate). MS (DCI/NH$_3$) m/e 284 (M+H)$^+$; The compound exists as a mixture of rotomers. Data for trans isomer: $^1$H NMR (300 MHz, CDCl$_3$): δ ppm 4.60 (d, 1H), 4.51 (d, 1H), 4.30 (d, 1H), 4.24 (d, 1H), 3.62 (s, 3H), 3.59 (s, 3H), 3.57 (s, 3H), 3.54 (s, 3H), 2.40–2.28 (m, 2H), 2.11–2.04 (m, 2H), 1.90–1.81 (m, 4H), 0.0 (s, 18H). Data for cis isomer: $^1$H NMR (300 MHz, CDCl$_3$): δ ppm 4.55–4.40 (m, 1H), 4.20–4.15 (m, 1H), 3.59 (s, 6H), 2.15–1.89 (m, 4H), 0.00 (s, 9H). MS (DCI/NH$_3$) m/e 284 (M+H)$^+$.

EXAMPLE 9D

5R-Trimethylsilanylethynyl-pyrrolidine-2S-carboxylic acid methyl ester

Iodotrimethylsilane (6.4 mL, 42.9mmol) was added to the solution of the 2S,5R-isomer of Example 9C (10.15 g, 35.8 mmol) in chloroform (20 mL). The mixture was stirred for 1.5 hours at 65° C. The mixture was concentrated under reduced pressure, purified by chromatography (50%-60% EtOAc/Hexane) to give the title amine (7.4 g, 93%). MS (DCI) m/z 226 (M+H)$^+$.

EXAMPLE 9E

5R-Ethynyl-pyrrolidine-1,2S-dicarboxylic acid 1-tert-butyl ester 2-methyl ester

The compound of Example 9D (7.4 g, 32.9 mmol) and di-tert-butyl dicarbonate (8.6 g, 39.8 mmol) were dissolved in dichloromethane (20 mL) then triethylamine (7.2 mL) was added. After the reaction was over, the mixture was concentrated under reduced pressure to give the crude Boc-protected pyrrolidine (10.5 g), which was used in the next step without purification. MS (DCI) m/z 326 (M+H)$^+$.

This intermediate (32.9 mmol) was dissolved in THF (20 mL), and tetrabutylammonium fluoride (1 M solution in THF, 39.5 mL, 39.5 mmol ) was added to the mixture at 0° C. After 30 minutes, the solvent was removed under reduced pressure. The crude product was chromatographed on silica gel (30% EtOAc/Hexane) to provide the title product (6.9 g, 84%). MS (DCI) m/z 254 (M+H)$^+$.

EXAMPLE 9F

5R-Ethenyl-pyrrolidine-1,2S-dicarboxylic acid 1-tert-butyl ester 2-methyl ester

The above Boc-protected amine (6.9 g, 27.2 mmol) was dissolved in ethyl acetate (130 mL). 5% Pd/BaSO$_4$ (260 mg) and quinoline (6.5 rniL) were added. The mixture was stirred under H$_2$ (20 psi ) at room temperature for 45 minutes. The mixture was filtered, washed with 1 N HCl and concentrated to provide 5R-vinyl-pyrrolidine-1,2S-dicarboxylic acid 1-tert-butyl ester 2-methyl ester (6.2 g 100%). MS (DCI) m/z 256 (M+H)$^+$.

EXAMPLE 9G 2S-(2S-Cyano-pyrrolidine-1-carbonyl)-5R-vinyl-pyrrolidine-1-carboxylic acid tert-butyl ester The above vinyl starting material (6.9 g, 27.2 mmol) was was dissolved in 50 mL of ethanol and then 1.7 M LiOH (48 mmol) was added. The mixture was stirred at room temperature for 2 hours until the starting material was consumed. The mixture was acidified with 1 N HCl (pH=2) and then extracted with ethyl acetate (3×). The combined organic layers were dried (Na$_2$SO$_4$), filtered and concentrated under reduced pressure to provide the crude acid (6.9 g, 99%), which was used in the next step without purification. MS (DCI) m/z 242 (M+H)$^+$. 2S-cyanopyrrolidine HCl salt (22.6 mmol) and 2-(1H-benzotriazole-1-yl)-1,1,3,3-tetramethyluronium tetrafluoroborate (TBTU, 6.35 g, 26.8 mmol) were combined with the above intermediate in 10 mL of DMF, and then Et3N (4.4 mL, 30.6 mmol) was added. After stirring overnight, the mixture was concentrated and purified by flash chromatography (40%-50% EtOAc/Hexane) to provide the title compound (5.0 g, 74%). MS (ESI) m/z 320 (M+H)$^+$.

EXAMPLE 9H 2S-(2S-Cyano-pyrrolidine-1-carbonyl)-5R-formyl-pyrrolidine-1-carboxylic acid tert-butyl ester The compound of Example 9G (0.34 g, 1.06mmol) in 2 mL each of CH$_2$Cl$_2$ and MeOH was cooled to −78° C., and O$_3$ was bubbled into the mixture for 30 minutes. Then O$_2$ was bubbled for 5 minutes followed by the addition of Me$_2$S (2 mL). The cooling bath was then removed allowing the mixture to slowly warm over 1.5 hours. The mixture was concentrated in vacuo, and the resulting oil purified by column chromatography to provide the aldehyde product (270 mg, 78%). MS (DCI) m/z 322 (M+H)$^+$.

EXAMPLE 9I 2S-(2S-Cyano-pyrrolidine-1-carbonyl)-5R-{((4-methoxy-phenyl)-methyl-amino)-methyl}-pyrrolidine-1-carboxylic acid tert-butyl ester The compound from Example 9H (50 mg, 0.155 mmol), and 4methoxyaniline (2 eq.) were mixed in 1 mL each of MeOH and MeOH buffer (pH=4, NaOAc: HOAc, 1:1). The mixture was stirred for 0.5 hour and NaCNBH$_3$ (25 mg, 0.19 mmol) was added. The mixture was filtered after 2 hours and purified by reverse phase HPLC (linear gradient of 0% to 70% acetonitrile/ 0.1% aqueous trifluoroacetic acid) to provide the desired product.

EXAMPLE 9J (2S)-1-((5R)-5-{((4-methoxyphenyl)amino)methyl}-L-prolyl)pyrrolidine-2-carbonitrile The Boc group of Example 9I was removed as described in Example 1G to provide the title compound. $^1$H NMR (400 MHz, MeOH-d$_4$) δ 1.76 (m, 1H), 1.99 (m, 2H), 2.25 (m, 5H), 3.14 (m, 1H), 3.50 (m, 3H), 3.69 (s, 3H), 4.36 (m, 2H), 4.62 (m, 1H), 6.56 (d, J=9.21 Hz, 2 H), 6.73 (d, J=8.90 Hz, 2H) ppm. MS (DCI) m/z 329 (M+H)$^+$.

EXAMPLE 10

(2S)-1-((5R)-5-{((4-methylphenyl)amino)methyl}-L-prolyl)pyrrolidine-2-carbonitrile The title compound was synthesized by substituting 4-methoxyaniline in Example 9 with 4-methylaniline. $^1$H NMR (500 MHz, MeOH-d$_4$) δ 1.66 (m, 1H), 1.95 (m, 2H), 2.18 (m, 4H), 2.30 (m, 2H), 2.42 (m, 2H), 3.07 (m, 1H), 3.35 (m, 1H), 3.48 (m, 1H), 3.58 (dd, J=14.97, 4.68 Hz, 1H), 4.37 (m, 2H), 4.59 (m, 1H), 6.46 (d, J=8.42 Hz, 2H), 6.90 (d, J=8.42 Hz, 2H) ppm. MS (ESI) m/z 313 (M+H)$^+$.

EXAMPLE 11

6-((5-(2-cyano-pyrrolidine-1-carbonyl)-pyrrolidin-2-ylmethyl)-amino)-nicotinonitrile The title compound was synthesized by substituting 4-methoxyaniline in Example 9 with 6-aminonicotinonitrile. $^1$H NMR (400 MHz, MeOH-d$_4$) δ 1.92 (m, 1H), 2.22 (m, 6H), 2.60 (m, 1H), 3.63 (m, 2H), 4.02 (m, 2H), 4.55 (m, 1H), 4.67 (m, 1H), 4.84 (m, 1H), 6.70 (d, J=9.51 Hz, 1H), 7.69 (d, J=1.05 Hz, 1H), 8.43 (m, 1H) ppm. MS (ESI) m/z 325 (M+H)$^+$.

EXAMPLE 12

(2S)-1-((5R)-5-{((4-bromophenyl)amino)methyl}-L-prolyl)pyrrolidine-2-carbonitrile The title compound was synthesized by substituting 4-methoxyaniline in Example 9 with 4-bromolaniline. $^1$H NMR (500 MHz, MeOH-d$_4$) δ 1.92 (m, 1H), 2.23 (m, 6H), 2.54 (m, 1H), 3.52 (m, 2H), 3.63 (m, 2H), 3.95 (m, 1H), 4.62 (m,J=9.04, 5.93 Hz, 1H), 4.83 (dd, J=7.95, 4.52 Hz, 1H), 6.65 (d, J=9.04 Hz, 2H), 7.25 (d, J=9.04 Hz, 2H) ppm. MS (DCI) m/z 377, 379 (M+H)$^+$.

EXAMPLE 13

(2S)-1-((5R)-5-{((phenyl)amino)methyl}-L-prolyl) pyrrolidine-2-carbonitrile

The title compound was synthesized by substituting 4-methoxyaniline in Example 9 with aniline. $^1$H NMR (400 MHz, MeOH-d$_4$) δ 1.92 (m, 1H), 2.20 (m, 6H), 2.55 (m, 1H), 3.59 (m, 4 H), 3.96 (m, 1H), 4.61 (dd, J=9.21, 5.83 Hz, 1H), 4.83 (m, J=3.38 Hz, 1H), 6.71 (m, 3H), 7.14 (m, 2H) ppm. MS (ESI) m/z 299 (M+H)$^+$.

EXAMPLE 14

(2S)-1-((5R)-5-(hydroxymethyl)-L-prolyl)pyrrolidine-2-carbonitrile

EXAMPLE 14A 2S-(2S-Cyano-pyrrolidine-1-carbonyl)-5R-hydroxymethyl-pyrrolidine-1-carboxylic acid tert-butyl ester The compound of Example 9G (3.0 g, 9.3 mmol) in 6 mL each of $CH_2Cl_2$ and MeOH were cooled to −78° C., and $O_3$ was bubbled into the mixture for 30 minutes. Then $O_2$ was bubbled for 5 minutes followed by the addition of $Me_2S$ (5 mL). The cooling bath was then removed, and the mixture was allowed to warm with stirring over 1.5 hours. The mixture was then concentrated in vacuo. The resulting oil was dissolved in 10 mL each of $CH_2Cl_2$ and EtOH followed by addition of $NaBH_4$ (0.534g, 14.1 mmol) and $NaBH(OAc)_3$ (0.882 g, 4.2 mmol). After stirring for 1 hour, water was added, and the mixture was extracted with ethyl acetate (3×). The combined extracts were dried ($Na_2SO_4$), concentrated to provide the title alcohol (2.8 g, 93%). MS (DCI) m/z 324 (M+H$^+$).

EXAMPLE 14B (2S)-1-((5R)-5-(hydroxymethyl)-L-prolyl)pyrrolidine-2-carbonitrile The compound of Example 14A was treated as described in Example 1G to provide the title compound. $^1$H NMR (300 MHz, MeOH-d$_4$) δ 1.90–2.12 (m, 3H), 2.14–2.38 (m, 5H), 3.60–3.82 (m, 4H), 3.99 (m, 1H), 4.50 (m, 1H), 4.80 (m, 1H) ppm. MS (ESI) m/z 224 (M+H)$^+$, 242 (M+NH$_4$)$^+$.

EXAMPLE 15

(2S)-1-{(5R)-5-((4-bromophenoxy)methyl)-L-prolyl}pyrrolidine-2-carbonitrile

The compound of Example 14A (50 mg, 0.154 mmol), triphenylphosphine (53 mg, 0.200 mmol) and 4-bromophenol (0.17 mmol) were mixed in 1 mL of dry THF. Then diethyl azodicarboxylate (40% in toluene, 0.093 mL, 0.21 mmol) was added via a syringe. The reaction was heated at 50° C. overnight and purified by reverse phase HPLC.

This intermediate was treated as described in Example 1G to provide the title compound. $^1$H NMR (300 MHz, MeOH-d$_4$) δ 1.99 (m, 1H), 2.26 (m, 6H), 2.59 (dq, J=13.22, 8.25 Hz, 1H), 3.66 (m, 2H), 4.12 (dt, J=15.68, 6.40 Hz, 1H), 4.34 (d, J=5.76 Hz, 2H), 4.68 (dd, J=8.99, 5.93 Hz, 1H), 4.80 (m, J=7.46 Hz, 1H), 6.96 (d, J=9.16 Hz, 2H), 7.45 (d, J=9.16 Hz, 2H) ppm. MS (ESI) m/z 378/380 (M+H)$^+$.

EXAMPLE 16

(2S)-1-{(5S)-5-((4-bromophenoxy)methyl)-L-prolyl}pyrrolidine-2-carbonitrile

The trans alcohol was synthesized by substituting the corresponding cis olefin in Example 14 with the corresponding trans olefin. MS (DCI) m/z 324 (M+H$^+$). The title compound was synthesized by substituting the 5R alcohol in Example 15 with the corresponding 5S isomer. $^1$H NMR (500 MHz, MeOH-d$_4$) δ 2.14 (m, 4H), 2.32 (m, 3H), 2.69 (s, 1H), 3.68 (m, 2H), 4.17 (dd, J=10.29, 6.86 Hz, 1H), 4.27 (m, 1 H,) 4.32 (m, 1H), 4.65 (t, J=7.80 Hz, 1H), 4.85 (dd, J=7.95, 4.52 Hz, 1H), 6.96 (d, J=9.05 Hz, 2H), 7.45 (d, J=9.05 Hz, 2H) ppm. MS (ESI) m/z+378/380 (M+H)$^+$.

EXAMPLE 17

(2S)-1-((5S)-5-(hydroxymethyl)-L-prolyl)pyrrolidine-2-carbonitrile

The title compound was synthesized by substituting the 5R alkene in Example 14 with the corresponding 5S isomer described in Example 22. $^1$H NMR (300 MHz, MeOH-d$_4$) δ 1.92–12.04 (m, 2H), 2.11–2.38 (m, 5H), 2.61 (m, 1H), 3.60–3.70 (m, 3H), 3.85 (m, 1H), 3.91 (m, 1H), 4.53 (m, 1H), 4.80 (m, 1H) ppm. MS (ESI) m/z 224 (M+H)$^+$.

EXAMPLE 18

(2S)-1-{(5R)-5-((4-fluorophenoxy)methyl)-L-prolyl]pyrrolidine-2-carbonitrile

The title compound was synthesized by substituting 4-bromophenol in Example 15 with 4-fluorophenol. $^1$H NMR (500 MHz, MeOH-d$_4$) δ 2.01 (m, 2H), 2.25 (m, 7H), 2.60 (m, 1H), 4.12 (m, 1H), 4.32 (m, 2H), 4.68 (dd, J=9.04, 5.93 Hz, 1H), 4.84 (dd, J=7.95, 4.52 Hz, 1H), 7.04 (m, 5H) ppm. MS (DCI) m/z 318 (M+H$^+$).

EXAMPLE 19

3-{(5R)-5-((4-bromophenoxy)methyl)-L-prolyl}-1,3-thiazolidine

The title compound was synthesized by substituting 2S-cyanopyrrolidine in Example 15 with thiazolidine. $^1$H NMR (MeOH-d$_4$, 500 MHz) δ 1.98 (m, 1H), 2.22 (m, 1H), 2.32 (m, 1H), 2.56 (m, 1H), 3.10 (m, 1H), 3.18 (m, 1H), 3.77 (m, 1H), 3.89 (m, 1H), 4.12 (m, 1H), 4.32 (m, 2H), 4.54 (m, 1H), 4.68 (dd, J=9.98, 4.68 Hz, 1H), 4.75 (m, 1H), 6.96 (d, J=9.04 Hz, 2H), 7.44 (d, J=9.04 Hz, 2H) ppm. MS (ESI) m/z 371/373 (M+H)$^+$.

EXAMPLE 20

(2S)-{(5R)-5-((2,6-dichlorophenoxy)methyl)-L-prolyl}pyrrolidine-2-carbonitrile

The title compound was synthesized by substituting 4-bromophenol in Example 15 with 2,6-dichlorophenol. $^1$H NMR (500 MHz, MeOH-d$_4$) δ 2.23 (m, 7H), 2.62 (m, 1H), 3.66 (m, 2 H), 4.21 (m, 1H), 4.37 (m, 1H), 4.43 (m, 1H), 4.72 (dd, J=9.36, 5.93 Hz, 1H), 4.86 (dd, J=7.80, 4.37 Hz, 1H), 7.19 (t, J=8.11 Hz, 1H), 7.45 (d, J=8.42 Hz, 2H) ppm. MS (DCI) m/z 368, 370 (M+H)$^+$.

EXAMPLE 21

(2S)-1-{(5R)-5-((2-chlorophenoxy)methyl)-L-prolyl}pyrrolidine-2-carbonitrile

The title compound was synthesized by substituting 4-bromophenol in Example 15 with 2-chlorophenol. $^1$H NMR (500 MHz, MeOH-d$_4$) δ 1.97 (m, 1H), 2.27 (m, 6H), 2.59 (m, 1H), 3.67 (m, 2H), 4.22 (m, 1H), 4.42 (m, 2H), 4.69 (dd, J=8.73, 6.24 Hz, 1H), 4.84 (dd, J=7.80, 4.37 Hz, 1H), 7.01 (td, J=7.64, 1.25 Hz, 1H), 7.16 (dd, J=8.11, 1.25 Hz, 1H), 7.30 (m, 1H), 7.41 (dd, J=7.80, 1.56 Hz, 1H) ppm. MS (DCI) m/z 334, 336 (M+H)$^+$

EXAMPLE 22

(2S)-1-((5S)-5-vinyl-L-prolyl)pyrrolidine-2-carbonitrile

EXAMPLE 22A

5S-Ethynyl-pyrrolidine-1,2S-dicarboxylic acid 1-tert-butyl ester 2-methyl ester

Iodotrimethylsilane (6.17 mL, 43.2 mmol) was added to the solution of dimethyl (2S,55-5-((trimethylsilyl)ethynyl)pyrrolidine-1,2-dicarboxylate (10.2 g, 36 mmol, Example 9C) in chloroform (20 mL). The mixture was stirred for 2 hours at 65° C. The mixture was concentrated under reduced pressure.

The above oil was dissolved in THF (30 mL), and tetrabutylammonium fluoride (1 M solution in THF, 43 mL, 43.2 mmol) was added to the mixture at 0° C. After 30 minutes, the solvent was removed under reduced pressure. The crude product was chromatographed on silica gel (hexane/ethyl acetate, 1:4) to provide the amine product (4.5g, 82%). MS (DCI) m/z 154 (M+H)$^+$.

The above amine (4.5 g, 29.4 mmol) and di-tert-butyl dicarbonate (7.39 g, 33.3 mmol) were dissolved in THF (20 mL). A catalytic amount of DMAP was added. The mixture was refluxed overnight and then concentrated under reduced pressure. The resulting oil was chromatographed on silica gel (hexane/ethyl acetate, 3:1) to provide the Boc-protected product (6.7 g, 90%). MS (DCI) m/z 254 (M+H)$^+$.

EXAMPLE 22B

5S-Vinyl-pyrrolidine-1,2S-dicarboxylic acid 1-tert-butyl ester 2-methyl ester

The above Boc-protected amine (6.2 g, 24.5 mmol) was dissolved in ethyl acetate (124 mL). 5% Pd/BaSO$_4$ (248 mg) and quinoline (6.2 mL) were added. The mixture was stirred under 20 psi H$_2$ at room temperature for 4–5 minutes. The mixture was filtered, washed with 1 N HCl and concentrated to provide the vinyl product (6.2 g 100%). MS (DCD m/z 256 (M+H)$^+$.

EXAMPLE 22C

5S-Vinyl-pyrrolidine-1,2S-dicarboxylic acid 1-tert-butyl ester

Example 22B (5.8 g, 24.1 mmol) was dissolved in 1.7 M LiOH (48 mmol) and ethanol (20 mL). The mixture was stirred at room temperature for 2 hours until the starting material was consumed. The mixture was acidified with 1 N HCl (pH=2) and then extracted with ethyl acetate (3×20 mL). The combined organic layers were dried (Na$_2$SO$_4$), filtered and concentrated under reduced pressure to provide the titled compound (5.7 g, 100%). MS (DCI) m/z 242 (M+H)$^+$.

EXAMPLE 22D 2S-(2S-Cyano-pyrrolidine-1-carbonyl)-5S-vinyl-pyrrolidine-1-carboxylic acid tert-butyl ester Example 22C (1.01 g, 4.14 mmol), 2S-cyanopyrrolidine HCl salt (4.97 mmol) and 2-(1H-benzotriazole-1-yl)-1,1,3,3-tetramethyluronium tetrafluoroborate (TBTU, 1.60 g, 4.97 mmol) were mixed in 4 mL each of CH$_2$Cl$_2$ and DMF, and then Et$_3$N (approx. 1.2 mL) was added until the pH of the mixture reached 6~7 (by wet pH paper). After stirring overnight, the mixture was concentrated and purified by flash chromatography to provide the title compound (0.92 g, 70%). MS (ESI) m/z 320 (M+H)$^+$.

EXAMPLE 22E (2S)-1-((5S)-5-vinyl-L-prolyl)pyrrolidine-2-carbonitrile

The Boc group of Example 22D was removed as described in Example 1G to provide the title compound. $^1$H NMR (400 MHz, MeOH-d$_4$) δ 2.01 (m, 3H), 2.25 (m, 5H), 2.70 (m, 1H), 3.65 (m, 2H), 4.64 (t, J=8.29 Hz, 1H), 4.83 (dd, J=7.83, 4.45 Hz, 1H), 5.47 (d, J=10.43 Hz, 1 H), 5.56 (d, J=17.18 Hz, 1H), 6.00 (ddd, J=17.18, 10.13, 7.67 Hz, 1H) ppm. $^{13}$C NMR (MeOH-d$_4$, 100 MHz) δ 26.1, 29.4, 30.8, 31.8, 47.6, 48.2, 59.9, 64.4, 119.2, 122.5, 132.8, 168.8 ppm. MS (ESI) m/z 220 (M+H)$^+$.

EXAMPLE 23

(2S)-1-{(5R/S)-5-((E)-2-(3-methylphenyl)vinyl)-L-prolyl}pyrrolidine-2-carbonitrile A 5 mL microwave tube was charged with a magnetic stirring bar, DMF (2 mL), Example 22D (150 mg, 0.59 mmol), palladium acetate (5.6 mg, 0.03 mmol), trio-tolyphosphine (15 mg, 0.06 mmol), diisopropylethylamine(0.18 mL, 118 mmol) and 3-methyliodobenzene (0.6 mmol). The tube was flushed with nitrogen and placed in the microwave reaction vessel. It was heated to 100° C. for 30 minutes, cooled, filtered and then purified by reverse-phase HPLC.

The Boc group was removed as described in Example 1G to provide the title compound. $^1$H NMR (400 MHz, MeOH-d$_4$) δ 2.22 (m, 10H), 2.66 (m, 1H), 3.66 (m, 2H), 4.38 (m, 1H), 4.66 (dd, J=9.36, 5.37 Hz, 1H), 4.85 (m, 1H), 6.39 and 6.30 (dd, J=15.96, 8.59 Hz, 1H), 6.83 and 6.86 (d, J=15.96 Hz, 1H), 7.14 (d, J=7.36 Hz, 1H), 7.28 (m, 3H). MS (DCI) m/z 310 (M+H)$^+$.

EXAMPLE 24

(2S)-1-{(5R/S)-5-((E)-2-phenylvinyl)-L-prolyl}pyrrolidine-2-carbonitrile

The title compound was synthesized by substituting 3-methyliodobenzene in Example 23 with iodobenzene. $^1$H NMR (500 MHz, MeOH-d$_4$) 2.12 (m, 8H), 2.66 (m, 1H), 3.57 (m, 2H), 4.37 (m, 1H), 4.57 (m, 2H), 6.24 and 6.35 (dd, J=15.75, 8.27 Hz, 1H), 6.77 and 6.80 (d, J=15.75 Hz, 1H), 7.21 (m, 1H), 7.25 (m, 1H), 7.40 (m, 2H) ppm. MS (DCI) m/z 296 (M+H)$^+$.

EXAMPLE 25

(2S)-1-{(5S/R)-5-((E)-2-(4-methylphenyl)vinyl)-L-prolyl}pyrrolidine-2-carbonitrile The title compound was synthesized by substituting 3-methyliodobenzene in Example 23 with 4-methyliodobenzene. $^1$H NMR (500 MHz, MeOH-d$_4$) δ 2.22 (m, 11H), 2.59 and 2.76(m, 1 H), 3.66 (m, 2H) 4.42 (m, 1H), 4.65 (m, 1H), 4.85 (dd, J=8.11, 4.37 Hz, 1H), 6.30 and 6.39 (dd, J=15.75, 8.58 Hz, 1H), 6.84 and 7.87 (d, J=15.75 Hz, 1H), 7.14 and 7.26 (d, J=7.17 Hz, 2H), 7.26 (m, 2H) ppm. MS (DCI) m/z 310 (M+H)$^+$.

EXAMPLE 26

(2S)-1-{(5S/R)-5-((E)-2-(2-bromophenyl)vinyl)-L-prolyl}pyrrolidine-2-carbonitrile The title compound was synthesized by substituting 3-methyliodobenzene in Example 23 with 2-bromoiodobenzene. $^1$H NMR (400 MHz, MeOH-d$_4$) δ 0.91 (m, 8H), 1.43 (m, 1H), 2.33 (t, J=6.60 Hz, 2H), 3.19 (m, 1H), 3.33 (t, J=8.29 Hz, 1H), 3.51 (dd, J=7.52, 4.45 Hz, 1H), 4.98 (dd, J=15.65, 8.29 Hz, 1H), 5.90 (m, 2H), 6.03 (t, J=7.36 Hz, 1H), 6.28 (d, J=7.98 Hz, 1H), 6.33 (d, J=7.98 Hz, 1H) ppm. MS (DCI) m/z 374, 376 (M+H)$^+$.

EXAMPLE 27

(2S)-1-{(5S/R)-5-((E)-2-(2-methylphenyl)vinyl)-L-prolyl}pyrrolidine-2-carbonitrile The title compound was synthesized by substituting 3-methyliodobenzene in Example 23 with 2-methyliodobenzene. $^1$H NMR (500 MHz, MeOH-d$_4$) δ 2.24 (m, 10H), 2.75 (m, 1H), 3.66 (m, 2H), 4.48 (m, 1H), 4.66 (m, 1H), 4.85 (m, 1H), 6.29 and 6.19 (dd, J=15.59, 8.42 Hz, 1 H), 7.22 (m, 4H) 7.52 (m, 1H) ppm. MS (DCI) m/z 310 (M+H)$^+$.

EXAMPLE 28

(2S)-1-{(5R/S)-5-((E)-2-(4-bromophenyl)vinyl)-L-prolyl}pyrrolidine-2-carbonitrile The compound was synthesized by substituting 3-methyliodobenzene in Example 23 with 4-bromoiodobenzene. $^1$H NMR (400 MHz, MeOH-d$_4$) δ 2.25 (m, 8H), 2.77 (m, 1H), 3.67 (m, 2 H), 4.47 (m, 1H), 4.66 (m, 1H), 4.85 (dd, #7.67, 4.30 Hz, 1H), 6.35 (dd, J=15.96, 8.29 Hz, 1 H), 6.88 (d, J=15.96 Hz, 1H), 7.41 (d, J=8.59 Hz, 2H), 7.53 (d, J=8.59 Hz, 2H) ppm. MS (DCI) m/z 374, 376 (M+H)$^+$.

EXAMPLE 29

(2S)-1-((5R/S)-5-{(E)-2-(4-(trifluoromethyl)phenyl)vinyl}-L-prolyl)pyrrolidine-2-carbonitrile The title compound was synthesized by substituting 3-methyliodobenzene in Example 23 with 4-trifluoromethyliodobenzene. $^1$H NMR (400 MHz, MeOH-d$_4$) δ 2.19 (m, 8H), 2.58 and 2.74 (m, 1H), 3.65 (m, 2H), 4.33 and 4.44 (m, 1H), 4.64 (m, 1H), 4.84 (m, 1H), 6.10 and 6.19 (dd, J=15.65, 8.90 Hz, 1H), 6.77 (m, 3H), 7.33 (dd, J=8.59, 3.68 Hz, 2H) ppm. MS (DCI) m/z 364 (M+H)$^+$.

EXAMPLE 30

(2S)-1-{(5S/R)-5-((E)-2-(3,4-dimethoxyphenyl)vinyl)-L-prolyl}pyrrolidine-2-carbonitrile The title compound was synthesized by substituting 3-methyliodobenzene in Example 23 with 2,4-dimethoxyiodobenzene. $^1$H NMR (400 MHz, MeOH-d4) δ 2.25 (m, 7H), 2.58 and 2.74 (m, 1H), 3.65 (m, 2H), 3.83 (s, 3H), 3.86 (s, 3H), 4.40 (m, 1H), 4.65 (m, 1H), 4.84 (dd, J=7.83, 4.45 Hz, 1H), 6.18 and 6.26 (dd, J=15.65, 8.90 Hz, 1H), 6.79 and 6.83 (d, J=15.65 Hz, 1H), 6.93 (d, J=8.29 Hz, 1H), 7.03 (m, 1H), 7.11 (m, 1H) ppm. MS (DCI) m/z 356 (M+H)$^+$.

EXAMPLE 31

(2S)-1-{(5R/S)-5-((E)-2-(4-chlorophenyl)vinyl)-L-prolyl}pyrrolidine-2-carbonitrile The title compound was synthesized by substituting 3-methyliodobenzene in Example 23 with 4-chloroiodobenzene. $^1$H NMR (500 MHz, MeOH-d$_4$) δ 2.22 (m, 8H), 2.76 (m, 1H), 3.66 (t, J=5.6 Hz, 2H), 4.47 (m, 1H), 4.65 (t, J=7.95 Hz, 1H), 4.85 (dd, J=7.95, 4.52 Hz, 1H), 6.33 (dd, J=15.91, 8.42 Hz, 1H), 6.89 (d, J=15.91 Hz, 1H), 7.37 (d, J=8.42 Hz, 2H), 7.48 (d, J=8.42 Hz, 2H) ppm. MS (DCI) m/z 330, 332 (M+H)$^+$.

EXAMPLE 32

(2S)-1-{(5R/S)-5-((E)-2-(1,3-benzodioxol-5-yl)vinyl)-L-prolyl}pyrrolidine-2-carbonitrile The title compound was synthesized by substituting 3-methyliodobenzene in Example 23 with 5-iodo-benzo(1,3)dioxole. $^1$H NMR (400 MHz, MeOH-d$_4$) δ 2.03 (m, 2H), 2.26 (m, 8H), 2.60 (m, 1H), 3.65 (m, 2H), 4.34 (m, 1H), 4.64 (dd, J=9.51, 5.22 Hz, 1H), 4.84 (dd, J=7.83, 4.45 Hz, 1H), 5.96 (s, 2H), 6.23 (dd, J=15.65, 8.59 Hz, 1H), 6.94 (m, 1H), 7.07 (m, 1H) ppm. MS (DCI) m/z 340 (M+H)$^+$.

EXAMPLE 33

(2S)-1-{(5R/S)-5-((E)-2-(4-hydroxyphenyl)vinyl)-L-prolyl}pyrrolidine-2-carbonitrile The title compound was synthesized by substituting 3-methyliodobenzene in Example 23 with 4-hydroxyiodobenzene. $^1$H NMR (400 MHz, MeOH-d$_4$) δ 2.27 (m, 8H), 2.76 (m, 1H), 3.67 (t, J=6.14 Hz, 2H), 4.51 (m, 1H), 4.68 (t, J=8.29 Hz, 1H), 4.85 (dd, J=7.67, 4.30 Hz, 1H), 6.48 (dd, J=15.96, 8.29 Hz, 1H), 6.98 (d, J=15.96 Hz, 1H), 7.70 (m, 4H) ppm. MS (DCI) m/z 312 (M+H)$^+$.

EXAMPLE 34

(2S)-1-{(5S/R)-5-((E)-2-(4-methoxyphenyl)vinyl)-L-prolyl}pyrrolidine-2-carbonitrile The title compound was synthesized by substituting 3-methyliodobenzene in Example 23 with 4-methoxyiodobenzene. $^1$H NMR (400 MHz, MeOH-d$_4$) δ 2.18 (m, 7H), 2.65 (m, 1H), 3.65 (m, 2H), 3.80 (s, 3H), 4.34 and 4.44 (m, 1H), 4.63 (dd, J=9.51, 5.52 Hz, 1H), 4.84 (dd, J=7.83, 4.45 Hz, 1H), 6.15 and 6.24 (dd, J=15.80, 8.75 Hz, 1H), 6.80 (d, J=15.34 Hz, 1H), 6.91 (d, J=8.90 Hz, 2H), 7.43 (d, J=8.90 Hz, 2H) ppm. MS (DCI) m/z 326 (M+H)$^+$.

EXAMPLE 35

(2S)-1-{(5S/R)-5-((E)-2-(3,4-dimethylphenyl)vinyl)-L-prolyl}pyrrolidine-2-carbonitrile The title compound was synthesized by substituting 3-methyliodobenzene in Example 23 with 3,4-dimethyliodobenzene. $^1$H NMR (400 MHz, MeOH-d$_4$) δ 2.06 (m, 4H), 2.23 (m, 8H), 2.38 (m, 2H), 2.56 (m, 1H), 3.47 (m, 1H), 3.67 (m, 1H), 4.61 (m, 1H), 4.86 (m, 1H), 6.08 and 6.16 (dd, J=16.11, 5.98 Hz, 1H), 6.35 and 6.60 (d, J=15.65 Hz, 1H), 7.16 (m, 3H) ppm. MS (DCI) m/z 324 (M+H)$^+$.

EXAMPLE 36

(2S)-1-{(5R/S)-5-(2-(3-methylphenyl)ethyl)-L-prolyl}pyrrolidine-2-carbonitrile

A solution of 2-(2-(S)-cyano-pyrrolidine-1-carbonyl)-5-(R/S)-(2-m-tolyl-vinyl)-pyrrolidine-1-carboxylic acid tert-butyl ester (Example 23) (50 mg) and 10% Pd/C (10 mg) in ethanol (5mL) was stirred under H$_2$ balloon overnight. The catalyst was removed by filtration, and the filtrate was concentrated to provide the desired product.

The Boc group of the above compound was removed as described in Example 1G to provide the desired product. $^1$H NMR (400 MHz, MeOH-d$_4$) δ 1.82 (m, 1H), 1.98 (m, 2H), 2.25 (m, 8H), 2.70 (m, 3H), 3.64 (t, J=6.60 Hz, 2H), 3.72 (m, 1H), 4.57 (t, J=8.29 Hz, 1H), 4.57 (t, J=8.29 Hz, 1H), 7.05 (m, 3H), 7.17 (d, J=7.36 Hz, 1H) ppm. MS (DCI) m/z 312 (M+H)$^+$.

EXAMPLE 37

(2S)-1-{(5R/S)-5-(2-(4-chlorophenyl)ethyl)-L-prolyl}pyrrolidine-2-carbonitrile

The title compound was synthesized by substituting 2-(2-(S)-cyano-pyrrolidine-1-carbonyl)-5-(R/S)-(2-m-tolyl-vinyl)-pyrrolidine-1-carboxylic acid tert-butyl ester in Example 36 with 2-(2-(S)-cyano-pyrrolidine-1-carbonyl)-5-(R/S)-(2-p-chlorophenyl-vinyl)-pyrrolidine-1-carboxylic acid tert-butyl ester. $^1$H NMR (400 MHz, MeOH-d$_4$) δ 1.83 (m, 1H), 1.98 (m, 2H), 2.24 (m, 6H), 2.71 (m, 4H), 3.64 (t, J=6.60 Hz, 2H), 3.73 (m, 1H), 4.59 (t, J=8.29 Hz, 1H), 7.25 (d, J=8.29 Hz, 2H), 7.31 (d, J=8.29 Hz, 2H) ppm. MS (ESI) m/z 332, 334 (M+H)$^+$.

EXAMPLE 38

(2S)-1-((5R/S)-5-(2-phenylethyl)-L-prolyl)pyrrolidine-2-carbonitrile

The title compound was synthesized by substituting 2-(2-(S)-cyano-pyrrolidine-1-carbonyl)-5-(R/S)-(2-m-tolyl-vinyl)-pyrrolidine-1-carboxylic acid tert-butyl ester in Example 36 with 2-(2-(S)-cyano-pyrrolidine-1-carbonyl)-5-(R/S)-(2-phenyl-vinyl)-pyrrolidine-1-carboxylic acid tert-butyl ester. $^1$H NMR (500 MHz, MeOH-d$_4$) δ 1.83 (m, 1H), 1.99 (m, 2H), 2.26 (m, 6 H), 2.65 (m, 1H), 2.77 (m, 2H), 3.64 (dd, J=7.02, 6.39 Hz, 2H), 3.76 (m, 1H), 4.58 (t, J=8.26 Hz, 1H), 4.83 (dd, J=7.95, 4.52 Hz, 1H), 7.25 (m, 5H) ppm. MS (DCI) m/z 298 (M+H)$^+$.

EXAMPLE 39

(2R,5S)-5-{((2S)-2-cyanopyrrolidin-1-yl)carbonyl}-N-(3-carboxy)phenylpyrrolidine-2-carboxamide

EXAMPLE 39A 2S-(4—Carboxy-phenylcarbamoyl)-5R-(2S-cyano-pyrrolidine-1-carbonyl)-pyrrolidine-1-carboxylic acid tert-butyl ester To a solution of 2S-(2S-cyano-pyrrolidine-1-carbonyl)-5R-formyl-pyrrolidine-1-carboxylic acid tert-butyl ester (278 mg, 0.865 mmol, Example 9H) in 2ml:3.2 mL of MeCN:t-BuOH was added 3.5 mL of 5% NaH$_2$PO$_4$ solution followed by 5.2 mL of 1M KMnO$_4$ solution (5.2 mmol) at room temperature. After 1 hour, ethyl acetate and saturated NaHSO$_3$ were added. Then 1N HCl was added to dissolve the solids. The aqueous layer was saturated with NaCl then extracted with ethyl acetate (2×) and chloroform (1×). The organic extracts were dried with Na$_2$SO$_4$ and concentrated to provide the crude acid (280 mg). MS (ESI) m/z 338 (M+H)$^+$.

EXAMPLE 39B (2R,5S)-5-{((2S)-2-cyanopyrrolidin-1-yl)carbonyl}-N-(3-carboxy)phenylpyrrolidine-2-carboxamide The crude acid from Step A was coupled to t-butyl 4-aminobenzoate in the presence of TBTU in a similar fashion as described in Example 3. The deprotection was done in the same method as described in Example 1G to provide the title compound. $^1$H NMR (400 MHz, MeOH-d$_4$) δ 2.1–2.4 (m, 6H), 2.65 (m, 2H), 3.68 (m, 2H), 4.57 (t, J=7.67 Hz, 1H), 4.71 (t, J=7.67 Hz, 1H), 4.89 (dd, J=7.67, 4.30 Hz, 1H), 7.74 (d, J=8.90 Hz, 2H), 8.02 (d, J=8.90 Hz, 2H) ppm. MS (ESI) m/z 347 (M+H)$^+$.

EXAMPLE 40

(2S)-1-((5R)-5-{(methyl(phenyl)amino)methyl}-L-prolyl)pyrrolidine-2-carbonitrile The title compound was synthesized by substituting 4-methoxyaniline in Example 9 with N-methylaniline. $^1$H NMR (400 MHz, MeOH-d$_4$) δ 1.89 (m, 1H), 2.24 (m, 6H), 2.54 (m, 1H), 3.03 (s, 3H), 3.73 (m, 4H), 4.03 (m, 1H), 4.61 (dd, J=9.05, 5.98 Hz, 1H), 4.85 (m, 1H), 6.79 (m, 1H), 6.93 (m, 2H), 7.26 (m, 2H) ppm. MS (DCI) m/z 313 (M+H)$^+$.

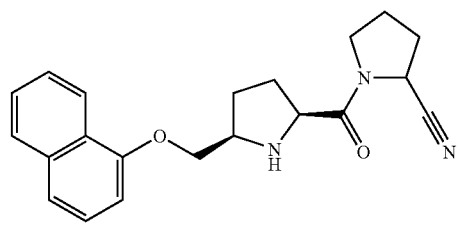

EXAMPLE 41

(2S)-1-{(5R)-5-(naphthalen-1-yloxymethyl)-L-prolyl}-pyrrolidine-2-carbonitrile

The title compound was synthesized by substituting 4-bromophenol in Example 15 with 1-naphthol. $^1$H NMR (500 MHz, MeOH-d$^4$) δ 2.26 (m, 7H), 2.64 (m, 1H), 3.69 (m, 2H), 4.30 (m, 1H), 4.56 (m, 2H), 4.76 (dd, J=9.04, 5.30 Hz, 1H), 4.87 (dd, J=7.95, 4.52 Hz, 1H), 7.00 (d, J=7.49 Hz, 1H), 7.41 (t, J=7.95 Hz, 1H), 7.50 (m, 3H), 7.82 (m, 1H), 8.43 (m, 1H). MS (ESI) m/z 350 (M+H)$^+$.

EXAMPLE 42

(2S)-1-{(5R)-5-((4-cyano-2-methoxyphenoxy)-methyl)-L-prolyl}-pyrrolidine-2-carbonitrile The compound of example 14A (0.167 mmol), 2-methoxy-4-cyanophenol (0.3 mmol) and triethylamine (0.334 mmol) were mixed in 2 mL of benzene. Cyanomethylenetrin-butylphosphorane (CMBP, 0.334 mmol) was added and the mixture was heated to 55° C. After the reaction was over, the mixture was purified by reverse-phase HPLC to give the title compound (40% yield). MS (ESI) m/z 455 (M+H)$^+$.

The Boc group was removed according to Example 1G to give the title compound. $^1$H NMR (500 MHz, MeOH-d$_4$) δ 1.98–2.09 (m, 1H), 2.10–2.46 (m, 5H), 2.55–2.65 (m, 1H), 3.62–3.71 (m, 2H), 3.91 (s, 3H), 4.15–4.24 (m, 1H), 4.37–4.47 (m, 2H), 4.69 (dd, J=8.89 Hz, 1H), 4.77–4.87 (m, 1H), 7.16 (d, 1H), 7.31–7.39 (m, 2H). MS (ESI) m/z 355 (M+H)$^+$.

EXAMPLE 43

(2S)-1-{(5R)-5-((2-cyano-4-trifluoromethylphenoxy)-methyl)-L-prolyl}-pyrrolidine-2-carbonitrile The title compound was synthesized by substituting 2-methoxy-4-cyanophenol in Example 42 with 2-cyano-4-(trifluoromethyl)phenol. $^1$H NMR (400 MHz, MeOH-d$_4$) δ 2.25 (m, 7H), 2.57 (m, 1H), 3.68 (m, 2H), 4.29 (m, 1H), 4.62 (m, 2H), 4.73 (dd, J=8.75, 5.06 Hz, 1H), 4.83 (m, 1H), 7.44 (d, J=8.90 Hz, 1H), 7.97 (dd, J=8.75, 1.99 Hz, 1H), 8.05 (d, J=2.45 Hz, 1 H). MS (ESI) m/z 393 (M+H)$^+$.

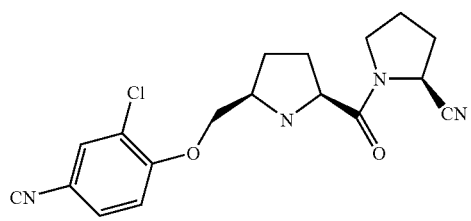

EXAMPLE 44

(2S)-1-{(5R)-5-((2-chloro-4-cyanophenoxy)-methyl)-L-prolyl}-pyrrolidine-2-carbonitrile The title compound was synthesized by substituting 2-methoxy-4cyanophenol in Example 42 with 2-chloro-4-cyanophenol $^1$H NMR (500 MHz, MeOH-d$_4$) δ 2.02–2.46 (m, 7H), 2.53–2.65 (m, J=13.25, 7.95 Hz, 1H), 3.62–3.74 (m, 2H), 4.23–4.33 (m, 1H), 4.49–4.59 (m, 2H), 4.72 (dd, J=8.58, 6.08 Hz, 1H), 4.80–4.87 (m, 1H), 7.30 (d, J=8.73 Hz, 1H), 7.71 (dd, J=8.58, 2.03 Hz, 1H), 7.84 (d, J=1.87 Hz, 1H). MS (ESI) m/z 359 (M+H)$^+$.

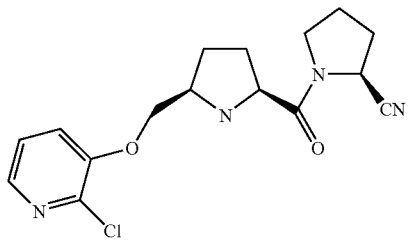

EXAMPLE 45

(2S)-1-{(5R)-5-((2-chloropyridyl-3-oxy)-methyl)-L-prolyl}-pyrrolidine-2-carbonitrile The title compound was synthesized by substituting 2-methoxy-4cyanophenol in Example 42 with 2-chloropyridin-3-ol. $^1$H NMR (400 MHz, MeOH-d$_4$) δ 2.01–2.46 (m, 7H), 2.54–2.64 (m, 1H), 3.63–3.72 (m, 2H), 4.21–4.31 (m, 1H), 4.46–4.52 (m, 2H), 4.72 (dd, J=8.59, 5.83 Hz, 1H), 4.82–4.87 (m, 1H), 7.39 (dd, J=8.13, 4.76 Hz, 1H), 7.60 (dd, J=8.13, 1.38 Hz, 1H), 8.02 (dd, J=4.91, 1.53 Hz, 1H). MS (ESI) m/z 335 (M+H)$^+$.

EXAMPLE 46

(2S)-1-{(5R)-5-((4-carboxy-2-methoxyphenoxy)-methyl)-L-prolyl}-pyrrolidine-2-carbonitrile

EXAMPLE 46A

4-Hydroxy-3-methoxy-benzoic acid tert-butyl ester

4-Hydroxy-3-methoxy-benzoic acid (1.0 g, 5.95 mmol), 1,3-dicyclohexycarbodiimide (1.5 g, 7.14 mmol) and 4dimethylaminopyridine (72.7 mg, 0.6 mmol) were mixed in t-butanol (10 mL) and stirred at room temperature for 4 hours. The reaction was filtered and purified by column chromatography to provide the title compound (1.0 g, 75%).

EXAMPLE 46B (2S)-1-{(5R)-5-((4-carboxy-2-methoxyphenoxy)-methyl)-L-prolyl}-pyrrolidine-2-carbonitrile The title compound was synthesized by substituting 2-methoxy-4cyanophenol in Example 42 with the compound of Example 46A. $^1$H NMR (500 MHz, MeOH-d$_4$) δ 2.03 (m, 1H), 2.27 (m, 6 H), 2.59 (m, 1H), 3.68 (m, 2H), 3.92 (s, 3H), 4.18 (m, 1H), 4.41 (m, 2H), 4.69 (m, 1H), 6.24 Hz, 1H), 4.84 (dd, J=7.95, 4.52 Hz, 1H), 7.11 (d, J=8.42 Hz, 1H), 7.64 (d, J=1.87 Hz, 1 H), 7.68 (dd, J=8.42, 1.87 Hz, 1H). MS (ESI) m/z 374 (M+H)$^+$.

EXAMPLE 47

(2S)-1-{(5R)-5-((4-carboxy-2-tert-butylphenoxy)-methyl)-L-prolyl}-pyrrolidine-2-carbonitrite

EXAMPLE 47A

4-Bromo-2-tert-butyl-phenol 2-tert-Butylphenol (2.03 g, 13.51 mmol) was dissolved in the mixture of 60 mL of $CH_2Cl_2$ and 40 mL of MeOH, then tetrabutylamonium tribromide (7.82 g, 16.22 mmol) was added. After one hour, the mixture was concentrated in vacuo and the residue was taken up in ether. The ether solution was washed with 1N HCl (2×) and brine (1×), then dried with $NaSO_4$. The solution was then concentrated in vacuo and the residue was purified by silica gel chromatography (10% EtOAc/Hexane) to give the titled bromophenol (2.72 g, 88%). MS (ESI) m/z −227 (M+H)−.

EXAMPLE 47B

1-Benzyloxy-4-bromo-2-tert-butyl-benzene

The compound of Example 47A (2.24 g, 9.77 mmol), benzyl bromide (1.4 mL, 11.72 mmol) and cesium carbonate (4.77 g, 14.65 mmol) were mixed in 10 mL of acetonitrile. The mixture was heated to 63° C. After 5 hours, the mixture was filtered and the filtrate was concentrated. The resulting residue was purified by silica gel chromatography (100% hexane) to provide the title compound (2.49 g, 80%).

EXAMPLE 47C

4-Benzyloxy-3-tert-butyl-benzoic acid methyl ester

The compound of Example 47B (778 mg), PdCl(dppf).$CH_2Cl_2$ (200 mg), and triethyl amine (1.02 mL) were mixed in 15 mL of methanol in a pressure vessel. The reaction vessel was charged with CO (500 psi) and then heated to 120° C. for 16 hours. The reaction was cooled to ambient temperature and the mixture was filtered. The filtrate was concentrated in vacuo and the resulting residue was purified by silica gel chromatography (0% then 10% EtOAc/Hexane) to provide the title compound (670 mg, 92%). MS (DCI) m/z 299 (M+H)+.

EXAMPLE 47D

4-Benzyloxy-3-tert-butyl-benzoic acid tert-butyl ester

The compound of Example 47C (630 mg, 2.11 mmol) in 4 mL of THF was treated with 4 mL of 1N NaOH aq. solution at ambient temperature. After stirring overnight, another 2 mL of 1.7 N LiOH aq. solution was added. After all the starting material had disappeared, the mixture was concentrated in vacuo and EtOAc was added to the resulting residue followed by 2N HCl solution. The mixture was extracted with EtOAc (3×) and the combined organic extracts were dried ($Na_2SO_4$) and concentrated in vacuum to give the crude 4-benzyloxy-3-tert-butyl-benzoic acid, which was carried on without purification.

The above crude acid was mixed with 5 mL of benzene and the mixture was heated to reflux. N,N-dimethylformamide tert-butyl acetal (3.69 mL) was added in batches. After 1.3 hours, the mixture was concentrated in vacuo and the resulting residue was purified by silica gel chromatography (0% then 5% EtOAc/Hexane) to give the desired tert-butyl ester (403 mg, 58%). MS (DCI) m/z 341 (M+H)+.

EXAMPLE 47E 3-tert-Butyl-4-hydroxy-benzoic acid tert-butyl ester

The compound of Example 47D (400 mg, 1.17 mmol) and 100 mg of 10% Pd/C were mixed in 3 mL each of EtOAc and EtOH in a flask and purged with nitrogen. A hydrogen balloon was connected to the flask. After all the starting material disappeared, the mixture was filtered. The filtrate was concentrated in vacuo to give the free phenol (322 mg). MS (DCI) m/z 251 (M+H)+.

EXAMPLE 47F 2-(4-tert-Butoxycarbonyl-2-tert-butyl-phenoxymethyl)-5-(2-cyano-pyrrolidine-1-carbonyl)-pyrrolidine-1-carboxylic acid tert-butyl ester The compound of example 14A (305 mg, 0.943 mmol), 3tert-butyl-4-hydroxy-benzoic acid tert-butyl ester (283 mg, 1.13 mmol), and triphenyl phosphine (396 mg, 1.51 mmol) were mixed in 5 mL of toluene. Then di-tert-butyl azodicarbonate (DBAD, 265 mg, 1.51 mmol) was added. The mixture was heated to 95 ° C. After the reaction was complete, the mixture was concentrated in vacuo and the resulting residue was purified by silica gel chromatography (20%–40% EtOAc/Hexane) to give the titled ether (436 mg, 83%).

EXAMPLE 47G (2S)-1-{(5R)-5-((4-carboxy-2-tert-butylphenoxy)-methyl)-L-prolyl}-pyrrolidine-2-carbonitril The compound of Example 47F was deprotected according to the procedures of Example 1G to give the title compound. $^1$H NMR (500 MHz, MeOH-$d_4$) δ 1.45 (s, 9H), 2.02–2.11 (m, 1 H), 2.13–2.38 (m, 5H), 2.39–2.50 (m, 1H), 2.55–2.65 (m, 1H), 3.63–3.75 (m, 2H), 4.24–4.32 (m, 1H), 4.40 (dd, J=10.60, 4.68 Hz, 1H), 4.59 (dd, J=10.60, 7.80 Hz, 1H), 4.76 (dd, J=8.89, 5.15 Hz, 1H), 4.78–4.89 (m, 1H), 7.13 (d, J=8.42 Hz, 1H), 7.92 (dd, J=8.42, 2.18 Hz, 1H), 8.04 (d, J=2.18 Hz, 1H). MS (ESI) m/z 400 (M+H)+.

EXAMPLE 48

(2S)-1-{(5R)-5-((4-carboxy-2-chlorophenoxy)-methyl)-L-prolyl}-pyrrolidine-2-carbonitrile The title compound was synthesized by substituting 2-tert-butylphenol in Example 47 with 2-chlorophenol. $^1$H NMR (400 MHz, MeOH-$d_4$) δ 2.23 (m, 7H), 2.59 (m, 1H), 3.68 (m, 2 H), 4.24 (m, 1H), 4.53 (d, J=5.22 Hz, 2H), 4.71 (dd, J=8.75, 5.98 Hz, 1H), 4.83 (overlap with solvent peak, 1H), 7.23 (d, J=8.59 Hz, 1H), 7.98 (dd, J=8.59, 2.15 Hz, 1H), 8.04 (d, J=2.15 Hz, 1H). MS (ESI) m/z 378 (M+H)+.

EXAMPLE 49

(2S)-1-{(5R)-5-((4-carboxy-2-iso-propylphenoxy)-methyl)-L-prolyl}-pyrrolidine-2-carbonitril The title compound was synthesized by substituting 2-tert-butylphenol in Example 47 with 2-iso-propylphenol. $^1$H NMR (400 MHz, MeOH-$d_4$) δ 1.23 (d, J=6.75 Hz, 3H), 1.26 (d, J=6.75 Hz, 3H), 2.24 (m, 7H), 2.60 (m, 1H), 3.51 (m, 1H), 3.66 (m, 2H), 4.22 (m, 1H), 4.45 (d, J=5.22 Hz, 2H), 4.73 (dd, J=8.90, 5.52 Hz, 1H), 4.85 (m, 1H), 7.05 (d, J=8.59 Hz, 1H), 7.89 (dd, J=8.59, 2.15 Hz, 1H), 7.94 (d, J=2.15 Hz, 1H). MS (ESI) m/z 386 (M+H)$^+$.

EXAMPLE 50

(2S)-1-{(5R)-5-([4-(tetrazol-5-yl)-2-chlorophenoxyl]-methyl)-L-prolyl}-pyrrolidine-2-carbonitrile

EXAMPLE 50A

5R-Hydroxymethyl-pyrrolidine-1,2S-dicarboxylic acid 1-tert-butyl ester 2-methyl ester The compound of Example 9F was reacted according to the procedures of Example 14A to give the title compound.

EXAMPLE 50B 5R-(2-chloro-4-cyano-phenoxymethyl)-pyrrolidine-1,2S-dicarboxylic acid 1-tert-butyl ester 2-methyl ester The compound of Example 50A was reacted according the procedure of Example 42 to give the title compound.

EXAMPLE 50C

5R-[2-Chloro-4-(1H-tetrazol-5-yl)-phenoxymethyl]-pyrrolidine-1,2S-dicarboxylic acid 1-tert-butyl ester 2-methyl ester NaN$_3$ (145 mg, 0.17 mmol) and NH$_4$Cl (91.8 mg, 0.17 mmol) were added to the compound of Example 50B (520 mg, 0.13 mmol) in DMF (2 mL) under N$_2$. The reaction was heated to 110° C. for 48 hours. Saturated NaHCO$_3$ was added and the mixture was extracted with EtOAc (3×). The combined extracts were dried (Na$_2$SO$_4$), concentrated and purified by column chromatography to give the product (520 mg, 90%). MS (ESI) m/z 438, 440 (M+H$^+$).

EXAMPLE 50D (2S)-1-{(5R)-5-([4-(tetrazol-5-yl)-2-chlorophenoxy]-methyl)-L-prolyl}-pyrrolidine-2-carbonitrile The compound of Example 50C was processed according to the procedures described in Examples 22C-E to give the title compound. $^1$H NMR (500 MHz, MeOH-$d_4$) δ 2.24 (m, 7H), 2.57 (m, 1H), 3.67 (m, 2H), 4.24 (m, 1H), 4.52 (d, J=5.30 Hz, 2H), 4.68 (dd, J=8.73, 5.93 Hz, 1H), 4.84 (m, 1H), 7.33 (d, J=8.73 Hz, 1H), 7.99 (dd, J=8.74, 2.18 Hz, 1H), 8.11 (d, J=2.18 Hz, 1H). MS (ESI) m/z 402 (M+H)$^+$.

EXAMPLE 51

(2S)-1-{(5R)-5-((5-carboxy-2-chlorophenoxy)-methyl)-L-prolyl}-pyrrolidine-2-carbonitrile The title compound was synthesized by substituting 4-bromo-2-tert-butyl-phenol in Example 47 with 2-chloro-5-bromophenol. $^1$H NMR (400 MHz, MeOH-$d_4$) δ ppm 2.25 (m, 7H), 2.62 (m, 1H), 3.68 (m, 2H), 4.24 (m, 1H), 4.50 (m, 2H), 4.70 (dd, J=8.59, 6.14 Hz, 1H), 4.86 (m, 1H), 7.53 (d, J=8.29 Hz, 1H), 7.68 (dd, J=8.29, 1.84 Hz, 1H), 7.75 (d, J=1.84 Hz, 1H). MS (ESI) m/z 378, 380 (M+H)$^+$.

EXAMPLE 52

(2S)-1-{(5R)-5-((5-carboxy-2-chloropyridyl-3-oxy)-methyl)-L-prolyl}-pyrrolidine-2-carbonitrile

EXAMPLE 52A

5-Hydroxy-nicotinic acid tert-butyl ester

5-Hydroxy-nicotinic acid methyl ester (1 g, 5.99 mmol) and potassium t-butoxide (4 g, 36 mmol) was stirred in THF (10 mL) and t-butanol (10 mL) at room temperature overnight. 1N HCl was added to adjust pH~7 and the mixture was extracted with EtOAc (3×). The combined extracts were dried (Na$_2$SO$_4$), concentrated and purified by column chromatography to give the product (400 mg, 34%). MS (DCI) m/z 196 (M+H)$^+$.

EXAMPLE 52B

6-Chloro-5-hydroxy-nicotinic acid tert-butyl ester

The compound of Example 52A (400 mg, 2.05 mmol) was dissolved in DMF (2 mL) and N-chlorosuccinimide (328 mg, 2.46 mmol) was added. The mixture was heated to 80° C. overnight, concentrated and purified by column chromatography to give the chloro pyridine (234 mg, 50%). MS (DCI) m/z 230, 232 (M+H$^+$).

EXAMPLE 52C (2S)-1-{(5R)-5-((5-carboxy-2-chloropyridyl-3-oxy)-methyl)-N-Boc-L-prolyl}-pyrrolidine-2-carbonitrile The title compound was synthesized by substituting 3-tert-butyl-4-hydroxy-benzoic acid tert-butyl ester in Example 47 with the compound of Example 52B. MS (ESI) m/z 479, 481 (M+H)$^+$.

EXAMPLE 52D (2S)-1-{(5R)-5-((5-carboxy-2-chloropyridyl-3-oxy)-methyl)-L-prolyl}-pyrrolidine-2-carbonitrile The Boc group was removed using precedure as described in Example 1G to give the title compound. $^1$H NMR (500 MHz, MeOH-$d_4$) δ 2.25 (m, 7H), 2.60 (m, 1H), 3.68 (m, 2 H), 4.27 (m, 1H), 4.56 (m, 2H), 4.72 (dd, J=8.73, 5.93 Hz, 1H), 4.84 (dd, J=7.96, 4.52 Hz, 1H), 8.03 (d, J=1.56 Hz, 1H), 8.60 (d, J=1.56 Hz, 1H). MS (ESI) m/z 379, 381 (M+H)$^+$.

EXAMPLE 53

(2S)-1-{(5R)-5-(5-carboxynaphthalen-1-yloxymethyl)-L-prolyl}-pyrrolidine-2-carbonitrile

EXAMPLE 53A

5-Hydroxy-naphthalene-1-carboxylic acid tert-butyl ester

The title compound was synthesized by substituting 4-benzyloxy-3-tert-butyl-benzoic acid in Example 47D with 5-hydroxy-naphthalene-1-carboxylic acid (Girardet, Lo Russo. Helv.Chim.Acta;, 49, 471–478, 1966). MS (DCI) m/z 245 (M+H)$^+$.

EXAMPLE 53B (2S)-1-{(5R)-5-(5-carboxynaphthalen-1-yloxymethyl)-L-prolyl}-pyrrolidine-2-carbonitrile The title compound was synthesized by substituting 3-tert-butyl-4-hydroxy-benzoic acid tert-butyl ester in Example 47 with the compound of Example 53A. $^1$H NMR (500 MHz, MeOH-d$_4$) δ 2.29 (m, 7H), 2.64 (m, 1H), 3.70 (m, 2H), 4.31 (m, 1H), 4.59 (m, 2H), 4.74 (m, 1H), 4.87 (dd, J=7.96, 4.52 Hz, 1H), 7.08 (d, J=7.49 Hz, 1H), 7.55 (m, 2H), 8.21 (dd, J=7.18, 1.25 Hz, 1H), 8.53 (d, J=8.73 Hz, 1H), 8.68 (d, J=8.42 Hz, 1H). MS (ESI) m/z 394 (M+H)$^+$.

EXAMPLE 54

(2S)-1-{(5R)-5-((4-carboxynaphthalen-1-yloxy)methyl)-L-prolyl}-pyrrolidine-2-carbonitrile The title compound was synthesized by substituting 2-tert-butylphenol in Example 47 with 1-naphthol. $^1$H NMR (500 MHz, MeOH-d$_4$) δ 2.21 (m, 7H), 2.55 (m, 1H), 3.70 (m, 2H), 4.15 (m, 1H), 4.65 (m, 2H), 4.76 (m, 1H), 4.86 (dd, J=7.96, 4.52 Hz, 1H), 7.04 (d, J=8.24 Hz, 1H), 7.56 (m, 1H), 7.62 (m, 1H), 8.26 (d, J=8.24 Hz, 1H), 8.48 (d, J=7.93 Hz, 1H), 9.01 (d, J=8.54 Hz, 1H). MS (ESI) m/z 394 (M+H)$^+$.

EXAMPLE 55

(2S)-1-{(5R)-5-((5-carboxy-3-chloropyridyl-2-oxy)-methyl)-L-prolyl}-pyrrolidine-2-carbonitrile The title compound was synthesized by substituting 3-tert-butyl-4-hydroxy-benzoic acid tert-butyl ester in Example 47 with 5-chloro-6-hydroxy-nicotinic acid tert-butyl ester (CIBA-GEIGY AG; FR 2218101; 1974; DE 2406930; 1976; Chem.Abstr.; 86; 121372). $^1$H NMR (400 MHz, MeOH-d$_4$) δ 2.22 (m, 7H), 2.58 (m, 1H), 3.65 (m, 2H), 4.22 (m, 1H), 4.68 (dd, J=8.75, 5.98 Hz, 1H), 4.85 (m, 3H), 8.32 (d, J=2.15 Hz, 1H), 8.73 (d, J=2.15 Hz, 1H). MS (ESI) m/z 379 (M+H)$^+$.

EXAMPLE 56

(2S)-1-{(5R)-5-((5-carboxy-2-bromophenoxy)-methyl)-L-prolyl}-pyrrolidine-2-carbonitrile

EXAMPLE 56A

4-Bromo-3-hydroxy-benzoic acid

Bromine (0.37 mL, 7.2 mmol) was added to 3-hydroxy-benzoic acid (500 mg, 3.6 mmol) in ethanol (2 mL) and acetic acid (1 mL). The mixture was stirred at room temperature for 30 min and then concentrated and purified by column chromatography to give the product (314 mg, 40%). MS (DCI) m/z 234 (M+NH$_4$)$^+$.

EXAMPLE 56B

4-Bromo-3-hydroxy-benzoic acid tert-butyl ester

The title compound was synthesized by substituting 4-benzyloxy-3-tert-butyl-benzoic acid in 47D with the compound of Example 56A.

EXAMPLE 56C (2S)-1-{(5R)-5-((5-carboxy-2-bromophenoxy)-methyl)-L-prolyl}-pyrrolidine-2-carbonitrile The title compound was synthesized by substituting 3-tert-butyl-4-hydroxy-benzoic acid tert-butyl ester in Example 47 with the compound of Example 56B. $^1$H NMR (400 MHz, MeOH-d$_4$) δ 2.27 (m, 7H), 2.59 (m, 1H), 3.67 (m, 2H), 4.26 (m, 1H), 4.50 (m, 2H), 4.71 (dd, J=8.75, 6.29 Hz, 1H), 4.86 (m, 1H), 7.60 (dd, J=8.29, 1.53 Hz, 1H), 7.71 (m, 2H). MS (ESI) m/z 514, 516 (M+H)$^+$.

EXAMPLE 57

(2S)-1-({(2S,5R)-5-[(2-methylphenoxy)methyl]pyrrolidin-2-yl}carbonyl)pyrrolidine-2-carbonitrile The title compound was synthesized by substituting 4-bromophenol in Example 15 with 2-methylphenol followed by removal of the Boc group as described in Example 1G. $^1$H NMR (400 MHz, MeOH-d$_4$) δ ppm 2.01–2.44 (m, 10H), 2.52–2.68 (m, 1H), 3.60–3.77 (m, 2H), 4.08–4.25 (m, 1H), 4.28–4.42 (m, 2H), 4.71 (dd, J=8.90, 5.83 Hz, 1H), 4.82–4.87 (m, 1H), 6.86–6.92 (m, 1H), 6.95 (d, J=7.67 Hz, 1H), 7.11–7.21 (m, 2H). MS (ESI) m/z 330 (M+H)$^+$.

EXAMPLE 58

(2S)-1-({(2S,5R)-5-[(2-methoxyphenoxy)methyl]pyrrolidin-2-yl}carbonyl)pyrrolidine-2-carbonitrile The title compound was synthesized by substituting 4-bromophenol in Example 15 with 2-methoxyphenol followed by removal of the Boc group as described in Example 1G. $^1$H NMR (300 MHz, MeOH-d$_4$) δ ppm 1.92–2.08 (m, 1H), 2.11–2.45 (m, 6H), 2.52–2.66 (m, 1H), 3.62–3.73 (m, 2H), 3.91 (s, 3H), 4.06–4.21 (m, 1H), 4.22–4.38 (m, 2H), 4.62–4.72 (m, 1 H), 4.84–4.88 (m, 1H), 6.87–6.96 (m, 1H), 7.00–7.10 (m, 3H). MS (ESI) m/z 528 (M+H)$^+$.

EXAMPLE 59

(2S)-1-({(2S,5R)-5-[(2,4-dichlorophenoxy)methyl]pyrrolidin-2-yl}carbonyl)pyrrolidine-2-carbonitrile The title compound was synthesized by substituting 4-bromophenol in Example 15 with 2,4-dichlorophenol followed by removal of the Boc group as described in Example 1G. $^1$H NMR (500 MHz, MeOH-d$_4$) δ ppm 2.01–2.11 (m, 1H), 2.10–2.45 (m, 6H), 2.53–2.64 (m, 1H), 3.59–3.74 (m, 2H), 4.16–4.26 (m, 1H), 4.40–4.44 (m, 2H), 4.70 (dd, J=8.70, 5.95 Hz, 1H), 4.81–4.85 (m, 1H), 7.15 (d, J=8.85

Hz, 1H), 7.32 (dd, J=8.85, 2.44 Hz, 1H), 7.46 (d, J=2.75 Hz, 1H). MS (ESI) m/z 368, 370 (M+H)+.

EXAMPLE 60

(2S)-1-[((2S,5R)-5-{[2-bromo-4-(trifluoromethyl)phenoxy]methyl}pyrrolidin-2-yl)carbonyl]pyrrolidine-2-carbonitrile The compound of Example 14A (50 mg, 0.15 mmol) and 3-bromo-4-fluorobenzotrifluoride (30 μL, 0.2 mmol) were stirred in DMF (1 mL) under $N_2$. NaH (13 mg, 0.3 mmol) was added to the mixture. It was stirred at room temperature for 1 hour. After the reaction was over, the mixture was purified by reverse-phase HPLC to give the Boc-protected compound (40% yield). MS (ESI) m/z 546, 548 (M+H)+.

The Boc group was removed according to Example 1G to give the title compound. $^1$H NMR (500 MHz, MeOH-$d_4$) δ ppm 2.05–2.44 (m, 7H), 2.49–2.65 (m, 1H), 3.50–3.59 (m, 1 H), 3.62–3.74 (m, 1H), 4.20–4.32 (m, 1H), 4.47–4.58 (m, 2H), 4.68–4.76 (m, 1H), 4.81–4.90 (m, 1H), 7.27 (dd, J=8.42, 4.05 Hz, 1H), 7.69 (d, J=8.73 Hz, 1H), 7.85–7.94 (m, 1H). MS (ESI) m/z 446, 448 (M+H)+.

EXAMPLE 61

(2S)-1-({(2S,5R)-5-[(4-bromo-2-methoxyphenoxy)methyl]pyrrolidin-2-yl}carbonyl)pyrrolidine-2-carbonitrile The title compound was synthesized by substituting 3-tert-butyl-4-hydroxy-benzoic acid tert-butyl ester in Example 47F with 2-methoxy-4-bromophenol followed by removal of the Boc group described in Example 1G. MS (ESI) m/z 408, 410 (M+H)+.

EXAMPLE 62

(2S)-1-({(2S,5R)-5-[(2-chloro-4-methoxyphenoxy)methyl]pyrrolidin-2-yl}carbonyl)pyrrolidine-2-carbonitrile The title compound was synthesized by substituting 3-tert-butyl-4-hydroxyl-benzoic acid tert-butyl ester in Example 47F with 2-chloro-4-methoxyphenol followed by removal of the Boc group described in Example 1G. $^1$H NMR (400 MHz, MeOH-$d_4$) δ ppm 1.97–2.11 (m, 1H), 2.11–2.46 (m, 7H), 2.53–2.67 (m, 1H), 3.62–3.71 (m, 2H), 3.76 (s, 3H), 4.12–4.24 (m, 1 H), 4.29–4.39 (m, 2H), 4.69 (dd, J=8.75, 5.98 Hz, 1H), 4.82–4.90 (m, J=7.83, 4.45 Hz, 1H), 6.86 (dd, J=8.90, 3.07 Hz, 1H), 7.01 (d, J=3.07 Hz, 1H), 7.12 (d, J=9.21 Hz, 1 H). MS (ESI) m/z 364 (M+H)+.

EXAMPLE 63

(2S)-1-({(2S,5R)-5-[(4-bromo-2-chlorophenoxy)methyl]pyrrolidin-2-yl}carbonyl)pyrrolidine-2-carbonitrile

EXAMPLE 63A 2R-(4-Bromo-2-chloro-phenoxymethyl)-5S-(2S-cyano-pyrrolidine-1-carbonyl)-pyrrolidine-1-carboxylic acid tert-butyl ester The title compound was synthesized by substituting 3-tert-butyl-4-hydroxyl-benzoic acid tert-butyl ester in Example 47F with 2-chloro-4-bromophenol. MS (ESI) m/z 512, 514 (M+H)+.

EXAMPLE 63B (2S)-1-({(2S,5R)-5-[(4-bromo-2-chlorophenoxy)methyl]pyrrolidin-2-yl}carbonyl)pyrrolidine-2-carbonitrile The title compound was synthesized after removal of the Boc group described in Example 1G. MS (ESI) m/z 412, 414 (M+H)+.

EXAMPLE 64

(2S)-1-[((2S,5R)-5-{[(4-chloro-1-naphthyl)oxy]methyl}pyrrolidin-2-yl)carbonyl]pyrrolidine-2-carbonitrile The title compound was synthesized by substituting 3-tert-butyl-4-hydroxyl-benzoic acid tert-butyl ester in Example 47F with 4chloro-naphthalen-1-ol followed by removal of the Boc group described in Example 1G. $^1$H NMR (400 MHz, MeOH-$d_4$) δ ppm 2.08–2.49 (m, 7H), 2.57–2.71 (m, 1H), 3.65–3.77 (m, 2H), 4.26–4.37 (m, 1H), 4.53–4.59 (m, 2H), 4.74–4.79 (m, 1H), 4.86 (dd, J=7.83, 4.76 Hz, 1H), 6.97 (d, J=8.29 Hz, 1H), 7.53 (d, J=8.29 Hz, 1H), 7.57–7.73 (m, 2H), 8.19 (d, J=7.98 Hz, 1H), 8.47 (d, J=7.36 Hz, 1H). MS (ESI) m/z 384 (M+H)+.

EXAMPLE 65

(2S)-1-({(2S,5R)-5-[(quinolin-4-yloxy)methyl]pyrrolidin-2-yl}-carbonyl)pyrrolidine-2-carbonitrile The title compound was synthesized by substituting 3-tert-butyl-4-hydroxyl-benzoic acid tert-butyl ester in Example 47F with 1-hydroxylquinoline followed by removal of the Boc group described in Example 1G. $^1$H NMR (400 MHz, MeOH-$d_4$) δ ppm2.10–2.51 (m, 7H), 2.60–2.72 (m, 1H), 3.72 (t, J=7.06 Hz, 2H), 4.38–4.49 (m, 1H), 4.83–4.89 (m, 1H), 4.91–5.00 (m, 2 H), 7.57 (d, J=6.44 Hz, 1H), 7.91–7.99 (m, 2H), 8.11–8.19 (m, 2H), 8.74 (d, J=8.59 Hz, 1H), 9.07 (d, J=6.44 Hz, 1H). MS (ESI) m/z 351 (M+H)+.

EXAMPLE 66

(2S)-1-({(2S,5R)-5-[(quinolin-5-yloxy)methyl]pyrrolidin-2-yl}carbonyl)pyrrolidine-2-carbonitrile The title compound was synthesized by substituting 3-tert-butyl-4-hydroxyl-benzoic acid tert-butyl ester in Example 47F with 5-hydroxylquinoline followed by removal of the Boc group described in Example 1G. $^1$H NMR (400 MHz, MeOH-$d_4$) δ ppm 2.09–2.48 (m, 8H), 2.59–2.72 (m, 1H), 3.72 (t, J=6.60 Hz, 2H), 4.29–4.40 (m, 1H), 4.62–4.75 (m, 2H), 4.83–4.89 (m, J=4.91 Hz, 1H), 7.36 (d, J=7.98 Hz, 1H), 7.79 (d, J=8.59 Hz, 1H), 7.91 (dd, J=8.59, 4.91 Hz, 1 H), 8.00 (dd, 1H), 9.08 (dd, J=5.06, 1.38 Hz, 1H), 9.44 (d, J=8.59 Hz, 1H). MS (ESI) m/z 351 (M+H)+.

EXAMPLE 67

(2S)-1-[((2S,5R)-5-{[4-bromo-2-(1H-pyrazol-3-yl)phenoxy]methyl}pyrrolidin-2-yl)carbonyl]pyrrolidine-2-carbonitrile The title compound was synthesized by substituting 3-tert-butyl-4-hydroxyl-benzoic acid tert-butyl ester in Example 47F with 4bromo-2-(1H-pyrazol-3-yl)-phenol followed by removal of the Boc group described in Example 1G. $^1$H NMR (400 MHz, MeOH-d$_4$) δ ppm 1.93 (dd, J=13.20, 9.21 Hz, 1H), 2.09–2.41 (m, 7H), 2.52–2.62 (m, 1H), 3.57–3.69 (m, 2H), 4.20–4.30 (m, 1H), 4.61–4.71 (m, 3H), 4.85 (dd, J=7.83, 4.45 Hz, 1H), 6.85 (d, J=8.59 Hz, 1H), 6.90 (d, J=2.45 Hz, 1H), 7.28 (dd, J=8.75, 2.61 Hz, 1H), 7.83 (d, J=2.45 Hz, 1 H), 7.91 (d, J=2.45 Hz, 1H). MS (ESI) m/z 444, 446 (M+H)$^+$.

EXAMPLE 68

(2S)-1-({(2S,5R)-5-[(2-tert-butylphenoxy)methyl]pyrrolidin-2-yl}carbonyl)pyrrolidine-2-carbonitrile The title compound was synthesized by substituting 3-tert-butyl-4-hydroxyl-benzoic acid tert-butyl ester in Example 47F with 2-tert-butyl-phenol followed by removal of the Boc group described in Example 1G. $^1$H NMR (400 MHz, MeOH-d$_4$) δ ppm 1.34–1.49 (m, 9H), 2.00–2.11 (m, 1H), 2.12–2.38 (m, 5H), 2.38–2.49 (m, 1H), 2.53–2.67 (m, 1H), 3.61–3.75 (m, 2 H), 4.18–4.34 (m, 2H), 4.49 (dd, J=10.29, 7.48 Hz, 1H), 4.73 (dd, J=8.73, 5.30 Hz, 1H), 4.85 (dd, J=7.95, 4.52 Hz, 1H), 6.95 (t, J=7.49 Hz, 1H), 7.05 (d, J=8.11 Hz, 1H), 7.16–7.24 (m, 1 H), 7.32 (dd, J=7.80, 1.25 Hz, 1H). MS (ESI) m/z 356 (M+H)$^+$.

EXAMPLE 69

(2S)-1-({(2S,5R)-5-[(2-tert-butyl-4-cyanophenoxy)methyl]pyrrolidin-2-yl}carbonyl)pyrrolidine-2-carbonitrile

EXAMPLE 69A

1-Benzyloxy-4-cyano-2-tert-butyl-benzene

1-Benzyloxy-4-bromo-2-tert-butyl-benzene made in example 47B (319 mg, 1 mmol), zinc cyanide (129 mg, 1.1 mmol) and Pd(PPh$_3$)$_4$ (34.5 mg, 0.03 mmol) were mixed in 4 mL of DMF then the mixture was heated to 175° C. in a microwave reactor (Emrys Optimizer by Personal Chemistry) for 5 minutes. The mixture was cooled to room temperature, and then water and EtOAc were added. The EtOAc extracts were dried over Na$_2$SO4, concentrated and the resulting residue was purified by flash chromatography (5–10% EtOAc/Hexanes) to give the desired nitrile (64 mg). MS (DCI) m/z 238 (M+H)$^+$.

EXAMPLE 69B 4-cyano-2-tert-butylphenol

The benzyl group of Example 69A was removed according the procedure described in example 47E to give the desired phenol. MS (DCI) m/z 193 (M+NH$_4$)$^+$.

EXAMPLE 69C (2S)-1-({(2S,5R)-5-[(2-tert-butyl-4-cyanophenoxy)methyl]pyrrolidin-2-yl}carbonyl)pyrrolidine-2-carbonitrile The title compound was synthesized by substituting 3-tert-butyl-4-hydroxy-benzoic acid tert-butyl ester in Example 47F with 4cyano-2-tert-butylphenol followed by removal of the Boc group described in Example 1G. $^1$H NMR (500 MHz, MeOH-d$_4$) δ ppm 1.44 (s, 9H), 1.99–2.39 (m, 6H), 2.39–2.50 (m, 1H), 2.53–2.64 (m, 1H), 3.61–3.75 (m, 2H), 4.24–4.32 (m, 1H), 4.40 (dd, J=10.60, 4.68 Hz, 1H), 4.60 (dd, J=10.60, 7.80 Hz, 1H), 4.75 (dd, J=8.73, 4.99 Hz, 1 H), 4.84 (dd, J=7.95, 4.52 Hz, 1H), 7.20 (d, J=8.42 Hz, 1H), 7.58–7.67 (m, 2 H). MS (ESI) m/z 381(M+H)$^+$.

EXAMPLE 70

(2S)-1-({(2S,5R)-5-[(4-bromo-2-tert-butylphenoxy)methyl]pyrrolidin-2-yl}carbonyl)pyrrolidine-2-carbonitrile

EXAMPLE 70A 4-bromo-2-tert-butyl-phenol

1-Benzyloxy-4-bromo-2-tert-butyl-benzene made in Example 47B was hydgrogenated using the procedure as described in example 47E to provide the titled phenol.

EXAMPLE 70B (2S)-1-({(2S,5R)-5-[(4-bromo-2-tert-butylphenoxy)methyl]pyrrolidin-2-yl}carbonyl)pyrrolidine-2-carbonitrile The title compound was synthesized by substituting 3-tert-butyl-4-hydroxy-benzoic acid tert-butyl ester in Example 47F with 4-bromo-2-tert-butyl-phenol followed by removal of the Boc group described in Example 1G. $^1$H NMR (300 MHz, MeOH-d$_4$) δ ppm 1.41 (s, 9H), 1.95–2.48 (m, 8H), 2.50–2.67 (m, 1H), 3.62–3.76 (m, 2H), 4.16–4.33 (m, 2H), 4.43–4.54 (m, 1 H), 4.72 (dd, J=8.65, 5.26 Hz, 1H), 4.79–4.85 (m, 1H), 6.99 (d, J=8.82 Hz, 1 H), 7.34 (dd, J=8.65, 2.54 Hz, 1H), 7.40 (d, J=2.37 Hz, 1H). MS (ESI) m/z 434, 436 (M+H)$^+$.

EXAMPLE 71

(2S)-1-({(2S,5R)-5-[(2-isopropylphenoxy)methyl]pyrrolidin-2-yl}carbonyl)pyrrolidine-2-carbonitrile The title compound was synthesized by substituting 3-tert-butyl-4-hydroxyl-benzoic acid tert-butyl ester in Example 47F with 2-iso-propyl-phenol followed by removal of the Boc group described in Example 1G. $^1$H NMR (500 MHz, MeOH-d$_4$) δ ppm 1.21 (d, J=6.86 Hz, 3H), 1.24 (d, J=6.86 Hz, 3H), 2.02–2.45 (m, 7H), 2.56–2.66 (m, 1H), 3.43–3.53 (m, 1H), 3.63–3.73 (m, 2H), 4.16–4.24 (m, 1H), 4.36 (d, J=4.99 Hz, 2H), 4.70 (dd, J=9.04, 5.93 Hz, 1H), 4.83–4.89 (m, 1H), 6.92–7.02 (m, 2H), 7.12–7.20 (m, 1H), 7.23–7.29 (m, 1H). MS (ESI) m/z 342 (M+H)$^+$.

EXAMPLE 72 ethyl 3-tert-butyl-4-[((2R,5S)-5-{[(2S)-2-cyanopyrrolidin-1-yl]carbonyl}pyrrolidin-2-yl)methoxy]benzoate

EXAMPLE 72A 3-tert-Butyl-4-hydroxy-benzoic acid ethyl ester

The compound of Example 47A (2.3 g), PdCl$_2$(dppf) .CH$_2$Cl$_2$ (820 mg), and triethyl amine (4.2 mL) were mixed in 40 mL of ethanol in a pressure vessel. The reaction vessel was charged with CO (500 psi) and then heated to 120° C. for 16 hours. The reaction was cooled to ambient temperature and the mixture was filtered. The filtrate was concentrated in vacuo and the resulting residue was purified by silica gel chromatography (0% then 10% EtOAc/Hexane) to provide the title compound (1.9 g, 83%). MS (DCI) m/z 223 (M+H)$^+$.

EXAMPLE 72B ethyl 3-tert-butyl-4-[((2R,5S)-5-{[(2S)-2-cyanopyrrolidin-1-yl]carbonyl}pyrrolidin-2-yl)methoxy]benzoate The title compound was synthesized by substituting 2-tert-butylphenol in Example 47 with 3-tert-butyl-4-hydroxy-benzoic acid ethyl ester followed by removal of the Boc group as described in Example 1G. $^1$H NMR (500 MHz, MeOH-d$_4$) δ ppm 1.41–1.49 (m, 9H), 2.01–2.11 (m, 1H), 2.12–2.37 (m, 5H), 2.38–2.50 (m, 1H), 2.50–2.66 (m, 1 h), 3.60–3.76 (m, 1 H), 4.23–4.31 (m, 1H), 4.34 (q, J=7.17 Hz, 2H), 4.39 (dd, J=10.60, 4.68 Hz, 1 H), 4.59 (dd, J=10.60, 7.80 Hz, 1H), 4.59 (dd, J=10.60, 7.80 Hz, 1H), 4.75 (dd, J=8.73, 5.30 Hz, 1 H), 4.84 (dd, J=7.95, 4.52 Hz, 1H), 7.13 (d, J=8.42 Hz, 1H), 7.13 (d, J=8.42 Hz, 1H), 7.92 (dd, J=8.42, 2.18 Hz, 1H), 7.92 (dd, J=8.42, 2.18 Hz, 1H), 8.02 (d, J=2.18 Hz, 1H), 8.02 (d, J=2.18 Hz, 1 H). MS (ESI) m/z 428 (M+H)$^+$.

EXAMPLE 73

{3-tert-butyl-4-[((2R,5S)-5-{[(2S)-2-cyanopyrrolidin-1-yl]carbonyl}pyrrolidin-2-yl)methoxy]phenoxy}acetic acid

EXAMPLE 73A (3-tert-Butyl-4-hydroxy-phenoxy)-acetic acid tert-butyl ester tert-Butyl-hydroquinone (500 mg, 3.0 mmol) and K$_2$CO$_3$ (1.11 g, 8.0 mmol) were mixed in acetonitrile (4 mL). t-Butyl bromoacetate (0.53 mL, 3.6 mmol) was added and the mixture was heated to reflux. After the reaction was over, it was concentrated and purified by silica gel chromatography (10% –25% EtOAc/Hexane) to give the title phenol (230 mg, 40%). MS (DCI) m/z 297 (M+H)$^+$.

EXAMPLE 73B

{3-tert-butyl-4-[((2R,5S)-5-{[(2S)-2-cyanopyrrolidin-1-yl]carbonyl}pyrrolidin-2-yl)methoxy]phenoxy}acetic acid The title compound was synthesized by substituting 4-bromophenol in Example 15 with (3-tert-butyl-4-hydroxyphenoxy)-acetic acid tert-butyl ester followed by removal of the Boc and tert-butyl groups as described in Example 1G. $^1$H NMR (500 MHz, MeOH-d$_4$) δ ppm 1.37–1.47 (s, 9H), 1.97–2.08 (m, 1H), 2.09–2.48 (m, 6H), 2.53–2.64 (m, 1H), 3.58–3.74 (m, 2H), 4.16–4.28 (m, 2H), 4.43 (dd, J=10.29, 7.80 Hz, 1H), 4.59 (s, 2H), 4.70 (dd, J=8.89, 5.46 Hz, 1 H), 4.82–4.88 (m, 1H), 6.75 (dd, J=8.89, 2.96 Hz, 1H), 6.96 (d, J=3.12 Hz, 1 H), 6.99 (d, J=8.73 Hz, 1H). MS (ESI) m/z 446(M+H)$^+$.

EXAMPLE 74

(2S)-1-[((2S,5R)-5-{[2-methoxy-4-(1H-tetraazol-5-yl)phenoxy]methyl}pyrrolidin-2-yl)carbonyl]pyrrolidine-2-carbonitrile The title compound was synthesized using the same reaction sequence of Example 50 by substituting 4-hydroxy-3-chlorobenzonitrile in Example 50A with 4-hydroxy-3-methoxybenzonitrile. $^1$H NMR (500 MHz, MeOH-d$_4$) δ ppm 1.98–2.10 (m, 1H), 2.11–2.47 (m, 6H), 2.61 (m, 1H), 3.59–3.75 (m, 2H), 3.94–4.06 (m, 3H), 4.13–4.27 (m, 1H), 4.36–4.52 (m, 2H), 4.69 (dd, J=9.04, 6.24 Hz, 1H), 4.85 (dd, J=7.95, 4.52 Hz, 1H), 7.24 (d, J=8.11 Hz, 1 H), 7.63 (dd, J=8.42, 1.87 Hz, 1H), 7.70 (d, J=1.87 Hz, 1H). MS (ESI) m/z 398 (M+H)$^+$.

EXAMPLE 75

3-tert-butyl-4-[((2R,5S)-5-{[(2S)-2-cyanopyrrolidin-1-yl]carbonyl}pyrrolidin-2-yl)methoxy]benzamide

EXAMPLE 75A 3-tert-Butyl-4-hydroxy-benzamide

The compound of Example 47E (800 mg, 4.1 mmol), DCC (856 mg, 5.4 mmol), and HOBt (540 mg, 5.4 mmol) were mixed in DMF (10 mL). Ammonium hydroxide (28%, 22 mL) was added to the mixture at 0° C. The reaction was stirred over night and purified by silica gel chromatography (70% -90% EtOAc/Hexane) to provide the title compound (700 mg, 87.5%). MS (DCI) m/z 194 (M+H)$^+$.

EXAMPLE 75B 3-tert-butyl-4-[((2R,5S)-5-{[(2S)-2-cyanopyrrolidin-1-yl]carbonyl}pyrrolidin-2-yl)methoxy]benzamide The title compound was synthesized by substituting 4-bromophenol in Example 15 with the above benzamide followed by removal of the Boc group as described in Example 1G. $^1$H NMR (500 MHz, MeOH-d$_4$) δ ppm 1.45 (s, 9H), 2.02–2.39 (m, 6H), 2.39–2.49 (m, 1H), 2.52–2.67 (m, 1H), 3.61–3.77 (m, 2H), 4.21–4.32 (m, 1H), 4.38 (dd, J=10.29, 4.68 Hz, 1 ), 4.57 (dd, J=10.45, 7.64 Hz, 1H), 4.75 (dd, J=8.73, 5.30 Hz, 1H), 4.83–4.89 (m, 1H), 7.12 (d, J=8.42 Hz, 1H), 7.77 (dd, J=8.73, 2.18 Hz, 1H), 7.89 (d, J=2.18 Hz, 1H). MS (ESI) m/z 415 (M+H)$^+$.

EXAMPLE 76

(2S)-1-[((2S,5R)-5-{[2-isopropyl-4-(1H-tetraazol-5-yl)phenoxy]methyl}pyrrolidin-2-yl)carbonyl]pyrrolidine-2-carbonitrile

EXAMPLE 76A

4-Bromo-2-isopropyl-phenol

The title compound was synthesized by substituting 2-tert-butylphenol in Example 47A with 2-isopropylphenol. MS (DCI) m/z 215, 217 (M+H)+.

EXAMPLE 76B 4-cyano-2-isopropyl-phenol

4-Bromo-2-isopropyl-phenol (500 mg, 2.3 mmol), $Zn(CN)_2$ (270 mg, 2.3 mmol) and tetrakis(triphenylphosophine)palladium (237 mg) were mixed in DMF (1 mL) in a microwave reaction tube. It was reacted under microwave condition at 180° C. for 20 minutes. The mixture was filted and purified by by silica gel chromatography (40% -60% EtOAc/Hexane) to provide the title compound (220 mg, 60%). MS (DCI) m/z 162 (M+H)+.

EXAMPLE 76C 2S-(2S-Cyano-pyrrolidine-1-carbonyl)-5R-[2-isopropyl-4-(1H-tetrazol-5-yl)-phenoxymethyl]-pyrrolidine-1-carboxylic acid tert-butyl ester The title compound was synthesized by substituting 4-hydroxy-3-chlorobenzonitrile in Example 50A with 4-hydroxy-3-isopropylbenzonitrile.

EXAMPLE 76D (2S)-1-[((2S,5R)-5-{[2-isopropyl-4-(1H-tetraazol-5-yl)phenoxy]methyl}pyrrolidin-2-yl)carbonyl]pyrrolidine-2-carbonitrile The Boc group was removed according to procedure described in Example 1G to give the title compound along with the other isomer with tert-butyl group attached to the tetrazole ring. $^1$H NMR (500 MHz, MeOH-d$_4$) δ ppm 1.30 (dd, J=11.85, 6.86 Hz, 6H), 1.95–2.09 (m, 1H), 2.04–2.38 (m, 6H), 2.43–2.54 (m, 1H), 3.62–3.79 (m, 1H), 3.87–4.06 (m, 1 ), 4.29–4.42 (m, 3H), 4.46–4.55 (m, 2H), 4.81–4.86 (m, 1H), 7.09 (d, J=8.74 Hz, 1H), 7.85 (dd, J=8.58, 2.03 Hz, 1H), 7.97 (d, J=1.87 Hz, 1H). MS (ESI) m/z 410 (M+H)+.

EXAMPLE 77

3-[((2R,5S)-5-{[(2S)-2-cyanopyrrolidin-1-yl]carbonyl}pyrrolidin-2-yl)methoxy]pyridine-2-carboxylic acid

EXAMPLE 77A

3-Hydroxy-pyridine-2-carboxylic acid tert-butyl ester

3-Hydroxypicolinic acid (500 mg, 3.6 mmol) was stirred in toluene (4 mL) and heated to 80° C. N,N-dimethylformamide di-t-butyl acetal (1.9 ml, 7.97 mmol) was added in portions. The mixture was stirred for 2 hours and then concentrated. It was purified by column chromatography to give the product (300 mg, 46%). MS (DCI) m/z 196 (M+H)+.

EXAMPLE 77B

The title compound was synthesized by substituting 3-tert-butyl-4-hydroxyl-benzoic acid tert-butyl ester in Example 47F with the above ester followed by removal of the Boc group described in Example 1G. $^1$H NMR (500 MHz, MeOH-d$_4$) δ ppm 2.00–2.10 (m, 1H), 2.11–2.45 (m, 6H), 2.54–2.69 (m, 1H), 3.67 (t, J=7.02 Hz, 2H), 4.21–4.31 (m, J=7.80, 3.43 Hz, 1 H), 4.38–4.48 (m, 1H), 4.57 (dd, J=10.45, 3.59 Hz, 1H), 4.74 (dd, J=8.73, 6.24 Hz, 1H), 4.79–4.82 (m, 1H), 7.68 (dd, J=8.73, 4.68 Hz, 1H), 7.84 (d, J=8.11 Hz, 1H), 8.32 (d, J=4.06 Hz, 1 H). MS (ESI) m/z 345 (M+H)+.

EXAMPLE 78

(2S)-1-[((2S,5R)-5-{[4-(1-tert-butyl-1H-tetraazol-5-yl)-2-isopropylphenoxy]methyl}pyrrolidin-2-yl)carbonyl]pyrrolidine-2-carbonitrile The title compound was obtained when the tert-butyl group was migrated onto the tetrazole ring in the removal of the Boc group in Example 76D. $^1$H NMR (400 MHz, MeOH-d$_4$) δ ppm 1.30 (dd, J=11.51, 6.90 Hz, 6H), 1.80 (s, 9H), 2.02–2.48 (m, 7H), 2.53–2.68 (m, 1H), 3.50–3.63 (m, 1H), 3.61–3.76 (m, 2H), 4.18–4.28 (m, 1H), 4.46 (d, J=4.91 Hz, 2H), 4.65–4.76 (m, 1H), 4.83–4.90 (m, 1H), 7.14 (d, J=8.90 Hz, 1H), 7.90–7.97 (m, 1 H), 8.01 (d, J=1.84 Hz, 1H). MS (ESI) m/z 480 (M+H)+.

EXAMPLE 79

(2S)-1-[((2S,5R)-5-{[4-(1-tert-butyl-1H-tetraazol-5-yl)-2-chlorophenoxy]methyl}pyrrolidin-2-yl)carbonyl]pyrrolidine-2-carbonitrile The title compound was obtained when the tert-butyl group was migrated onto the tetrazole ring in the removal of the Boc group in Example 50B. $^1$H NMR (400 MHz, MeOH-d4) δ ppm 1.80 (s, 9H), 2.01–2.48 (m, 7H), 2.51–2.67 (m, 1H), 3.61–3.76 (m, 2H), 4.20–4.33 (m, 1H), 4.52 (d, J=5.52 Hz, 2H), 4.66–4.75 (m, 1H), 4.82–4.88 (m, 1H), 7.32 (d, J=8.59 Hz, 1H), 8.06 (dd, J=8.59, 2.15 Hz, 1H), 8.14 (d, J=1.84 Hz, 1H). MS (ESI) m/z 458, 460 (M+H)+.

EXAMPLE 80

5-chloro-2-[((2R,5S)-5-{[(2S)-2-cyanopyrrolidin-1-yl]carbonyl}pyrrolidin-2-yl)methoxy]benzoic acid

EXAMPLE 80A

5-Chloro-2-hydroxy-benzoic acid tert-butyl ester

5-Chloro-2-hydroxy-benzoic acid (500 mg, 2.9 mmol), DCC (720 mg, 3.5 mmol) were mixed in t-butanol (5 mL). DMAP (50 mg) was added to the mixture. After 2 hours, the mixture was concentrated in vacuo and the resulting residue was purified by silica gel chromatography (0% then 10% EtOAc/Hexane) to give the desired tert-butyl ester (600 mg, 90%). MS (DCI) m/z 229, 231 (M+H)+.

EXAMPLE 80B 5-chloro-2-[((2R,5S)-5-{[(2S)-2-cyanopyrrolidin-1-yl]carbonyl}pyrrolidin-2-yl)methoxy]benzoic acid The title compound was synthesized by substituting 3-tert-butyl-4-hydroxyl-benzoic acid tert-butyl ester in Example 47F the above phenol followed by removal of the Boc group described in Example 1G. $^1$H NMR (500 MHz, MeOH-d$_4$) δ ppm 1.97–2.07 (m, 1H), 2.11–2.39 (m, 6H), 2.53–2.63 (m, 1H), 3.61–3.72 (m, 2H), 4.13–4.24 (m, 1H), 4.32–4.40 (m, 1 H), 4.46 (dd, J=10.45, 3.59 Hz, 1H), 4.69 (dd, J=8.73, 5.93 Hz, 1H), 4.80–4.84 (m, 1H), 7.22 (d, J=8.74 Hz, 1H), 7.55 (dd, J=8.73, 2.81 Hz, 1H), 7.84 (d, J=2.81 Hz, 1H). MS (ESI) m/z 378, 380 (M+H)$^+$.

EXAMPLE 81

{2-[((2R,5S)-5-{[(2S)-2-cyanopyrrolidin-1-yl]carbonyl}pyrrolidin-2-yl)methoxy]phenyl}acetic acid

EXAMPLE 81A (2-Hydroxy-phenyl)-acetic acid tert-butyl ester

Di-tert-butyl dicarbonate (218 mg, 0.1 mmol) was added to a solution of (2-hydroxybenzyl)triphenylphosphonium bromide (300 mg, 0.67 mmol) and triethylamine (0.32 mL, 0.3 mmol) in dry dichloromethane at room temperature under argon atmosphere. The mixture was stirred for 16 h and then poured into aqueous pH 7 buffer solution. Extraction with ethyl acetate followed by chromatography on silica gel (hexane/ethyl acetate=4/1) gave desired product (66 mg, 30%). MS (DCI) m/z 330 (M+H)$^+$.

EXAMPLE 81B

{2-[((2R,5S)-5-{[(2S)-2-cyanopyrrolidin-1-yl]carbonyl}pyrrolidin-2-yl)methoxy]phenyl}acetic acid The title compound was synthesized by substituting 3-tert-butyl-4-hydroxyl-benzoic acid tert-butyl ester in Example 47F with the above phenol followed by removal of the Boc group described in Example 1G. $^1$H NMR (400 MHz, MeOH-d4) δ ppm 1.98–2.45 (m, 7H), 2.50–2.64 (m, 1H), 3.61–3.76 (m, 4H), 4.08–4.20 (m, 1H), 4.33–4.44 (m, 2H), 4.69 (dd, J=9.21, 5.52 Hz, 1H), 4.82–4.88 (m, 1H), 6.92–7.10 (m, 2H), 7.20–7.34 (m, 2H). MS (ESI) m/z 358 (M+H)$^+$.

EXAMPLE 82

3-[((2R,5S)-5-{[(2S)-2-cyanopyrrolidin-1-yl]carbonyl}pyrrolidin-2-yl)methoxy]-4-fluorobenzoic acid The title compound was synthesized by substituting 3-tert-butyl-4-hydroxyl-benzoic acid tert-butyl ester in Example 47F with 4fluoro-3-hydroxy-benzoic acid tert-butyl ester followed by removal of the Boc group described in Example 1G. $^1$H NMR (500 MHz, MeOH-d$_4$) δ ppm 0.66–0.77 (m, 1H), 0.81–1.14 (m, 6H), 1.22–1.34 (m, 1H), 2.30–2.41 (m, 2H), 2.84–2.95 (m, 1H), 3.13–3.22 (m, 2H), 3.39 (dd, J=9.00, 5.95 Hz, 1H), 3.50–3.55 (m, 2 H), 5.95 (dd, J=10.98, 8.54 Hz, 1H), 6.38–6.45 (m, 1H), 6.51 (dd, J=8.09, 1.98 Hz, 1H). MS (ESI) m/z 362 (M+H)$^+$.

EXAMPLE 83

3-[((2R,5S)-5-{[(2S)-2-cyanopyrrolidin-1-yl]carbonyl}pyrrolidin-2-yl)methoxy]-4-isopropylbenzoic acid The title compound was synthesized by substituting 3-hydroxypicolinic acid in Example 77 with 3-hydroxy-4-isopropyl-benzoic acid (Journal; Croxall; Sowa; Nieuwland; JACSAT; *J.Amer.Chem.Soc.;* 1935, 57, 1549.). $^1$H NMR (500 MHz, MeOH-d4) δ ppm 1.26 (dd, J=15.91, 6.86 Hz, 6H), 2.07–2.45 (m, 7H), 2.56–2.66 (m, 1H), 3.49–3.59 (m, 1H), 3.62–3.74 (m, 2 H), 4.17–4.27 (m, 1H), 4.44 (d, J=4.99 Hz, 2H), 4.71 (dd, J=9.05, 5.62 Hz, 1H), 4.85 (dd, J=7.80, 4.37 Hz, 1H), 7.38 (d, J=8.11 Hz, 1H), 7.61 (d, J=1.56 Hz, 1H), 7.69 (dd, J=7.80, 1.56 Hz, 1H). MS (ESI) m/z 386 (M+H)$^+$.

EXAMPLE 84

2-[5-(2-Cyano-pyrrolidine-1-carbonyl)-pyrrolidin-2-ylmethoxy]-naphthalene-1-carboxylic acid The title compound was synthesized by substituting 3-hydroxypicolinic acid in Example 77 with 2-hydroxy-naphthalene-1-carboxylic acid. $^1$H NMR (500 MHz, MeOH-d$_4$) δ ppm 1.98–2.07 (m, 1H), 2.10–2.45 (m, 6H), 2.53–2.64 (m, 1H), 3.60–3.75 (m, 2H), 4.10–4.25 (m, 1 H), 4.51–4.61 (m, 2H), 4.70 (dd, J=8.89, 5.77 Hz, 1H), 4.84 (dd, J=7.80, 4.37 Hz, 1H), 7.42–7.49 (m, 1H), 7.51 (d, J=9.05 Hz, 1H), 7.53–7.59 (m, 1H), 7.91 (dd, J=11.23, 8.42 Hz, 2H), 8.03 (d, J=9.05 Hz, 1H). MS (ESI) m/z 394 (M+H)$^+$.

EXAMPLE 85

3-chloro-4-[((2R,5S)-5-{[(2S)-2-cyanopyrrolidin-1-yl]carbonyl}pyrrolidin-2-yl)methoxy]-N,N-dimethylbenzamide

EXAMPLE 85A

3-Chloro-4-hydroxy-N,N-dimethyl-benzamide

3-Chloro-4-hydroxy-benzoic acid (800 mg, 4.6 mmol), DCC (856 mg, 5.4 mmol), and HOBt (540 mg, 5.4 mmol) were mixed in DMF (10 mL). N,N-dimethyl amine (2M in THF, 4.6 mL) was added to the mixture at 0° C. The reaction was stirred over night and purified by silica gel chromatography (70%–90% EtOAc/Hexane) to provide the title compound (700 mg, 87.5%). MS (DCI) m/z 200, 202 (M+H)$^+$.

EXAMPLE 85B

The title compound was synthesized by substituting 3-tert-butyl-4-hydroxyl-benzoic acid tert-butyl ester in Example 47F with the above phenol followed by removal of the Boc group described in Example 1G. $^1$H NMR (400 MHz, MeOH-d$_4$) δ ppm 2.01–2.47 (m, 7H), 2.53–2.64 (m, 1H), 2.97–3.13 (m, 6H), 3.61–3.74 (m, 2H), 4.18–4.29 (m, 1H), 4.46–4.51 (m, 2 H), 4.70 (dd, J=8.59, 5.83 Hz, 1H), 4.83 (dd, J=7.83, 4.45 Hz, 1H), 7.22 (d, J=8.59 Hz, 1H), 7.41 (dd, J=8.44, 1.99 Hz, 1H), 7.53 (d, J=2.15 Hz, 1H). MS (ESI) m/z 405, 407 (M+H)$^+$.

EXAMPLE 86

(2S)-1-[((2S,5R)-5-{[(2-chloro-1-oxidopyridin-3-yl)oxy]methyl}pyrrolidin-2-yl)carbonyl]pyrrolidine-2-carbonitrile

EXAMPLE 86A 2S-(2-Chloro-pyridin-3-yloxymethyl)-5R-(2S-cyano-pyrrolidine-1-carbonyl)-pyrrolidine-1-carboxylic acid tert-butyl ester The compound of example 14A (0.167 mmol), 2-chloro-pyridin-3-ol (0.3 mmol) and triethylamine (0.334 mmol) were mixed in 2 mL of benzene. Cyanomethylenetri-n-butylphosphorane (CMBP, 0.334 mmol) was added and the mixture was heated to 55° C. After the reaction was over, the mixture was purified by reverse-phase HPLC to give the title compound (40% yield). MS (ESI) m/z 435, 437 (M+H).

EXAMPLE 86B (2S)-1-[((2S,5R)-5-{[(2-chloro-1-oxidopyridin-3-yl)oxy]methyl}pyrrolidin-2-yl)carbonyl]pyrrolidine-2-carbonitrile The above compound (77 mg, 0.14 mmol) and mCPBA (96 mg, 77%, 0.35 mmol) were mixed in $CH_2Cl_2$. The reaction was stirred over night and purified by reverse phase HPLC to provide the corresponding N-oxide. (51 mg, 64%). MS (ESI) m/z 451, 453 (M+H)$^+$.

The Boc group was removed according to Example 1G to give the title compound. $^1$H NMR (500 MHz, MeOH-d$_4$) δ ppm 2.01–2.46 (m, 7H), 2.51–2.69 (m, 1H), 3.61–3.75 (m, 2 H), 4.19–4.33 (m, 1H), 4.51–4.63 (m, 2H), 4.73 (dd, J=8.73, 5.62 Hz, 1H), 4.81–4.86 (m, 1 H), 7.36–7.48 (m, 2H), 8.21 (dd, J=6.40, 1.40 Hz, 1H). MS (ESI) m/z 351, 353 (M+H)$^+$.

EXAMPLE 87

(2S)-1-({(2S,5R)-5-[(2-chloro-4-morpholin-4-ylphenoxy)methyl]pyrrolidin-2-yl}carbonyl)pyrrolidine-2-carbonitrile The oven dried flask was charged with Pd$_2$(dba)$_3$ (5 mg, 0.005 mmol), (o-biphenyl)P(t-Bu)$_2$ (3 mg, 0.01 mmol) and NaH (11 mg, 0.27 mmol) and filled with argon. Toluene (1 mL), compound of Example 63A (45 mg, 0.088 mmol) and mophline (40 μL) were added. The mixture was heated to 80° C. for 1 hour. The mixture was then cooled to room temperature, filtered, and purified by reverse phase HPLC to give the product. (40 mg, 87%). MS (ESI) m/z 519, 521 (M+H)$^+$.

The Boc group was removed according to Example 1G to give the title compound. $^1$H NMR (400 MHz, MeOH-d$_4$) δ ppm 1.94–2.44 (m, 7H), 2.49–2.66 (m, 1H), 3.05–3.11 (m, 4 H), 3.63–3.71 (m, 1H), 3.77–3.86 (m, 5H), 4.12–4.20 (m, 1H), 4.31–4.37 (m, 2H), 4.64–4.73 (m, 1H), 4.83 (dd, J=7.98, 3.68 Hz, 1H), 6.92 (dd, J=9.05, 2.92 Hz, 1H), 7.06 (d, J=2.76 Hz, 1H), 7.10 (dd, J=8.90, 3.38 Hz, 1H). MS (ESI) m/z 419, 421 (M+H)$^+$.

EXAMPLE 88

(2S)-1-({(2S,5R)-5-[(4-amino-2-chlorophenoxy)methyl]pyrrolidin-2-yl}carbonyl)pyrrolidine-2-carbonitrile

EXAMPLE 88A 2S-(2S-Cyano-pyrrolidine-1-carbonyl)-5R-(2-chloro-4-nitro-phenoxymethyl)-pyrrolidine-1-carboxylic acid tert-butyl ester The title compound was synthesized by substituting 3-tert-butyl-4-hydroxy-benzoic acid tert-butyl ester in Example 47F with 2-chloro-4-nitro-phenol. MS (ESI) m/z 479, 481 (M+H)$^+$.

EXAMPLE 88B 2R-(4-Amino-2-chloro-phenoxymethyl)-5S-(2S-cyano-pyrrolidine-1-carbonyl)-pyrrolidine-1-carboxylic acid tert-butyl ester The above compound (50 mg, 0.14 mmol) and NH$_4$Cl (8 mg, 0.14 mmol) were mixed in EtOH/H$_2$O (1 mL: 0.2 mL). Iron powder (25 mg, 0.98 mmol) was added to the mixture and it was heated to 50° C. for 1 hour. It was filtered and ethyl acetate (25 mL) was added to the mixture. The solution was washed with brine (2×), then dried with NaSO$_4$. The solution was then concentrated in vacuo to give the titled analine. (48 mg, 100%). MS (ESI) m/z 449, 451 (M+H)$^+$.

EXAMPLE 88C (2S)-1-({(2S,5R)-5-[(4-amino-2-chlorophenoxy)methyl]pyrrolidin-2-yl}carbonyl)pyrrolidine-2-carbonitrile The Boc group was removed according to Example 1G to give the title compound. $^1$H NMR (500 MHz, MeOH-d$_4$) δ ppm 1.97–2.47 (m, 7H), 2.53–2.66 (m, 1H), 3.58–3.75 (m, 2 H), 4.16–4.26 (m, 1H), 4.34–4.43 (m, 2H), 4.69 (dd, J=8.89, 6.08 Hz, 1H), 4.83 (dd, J=7.96, 4.52 Hz, 1H), 7.04–7.08 (m, J=2.50 Hz, 1H), 7.17 (d, J=8.74 Hz, 1H), 7.20 (d, J=2.50 Hz, 1 H).

EXAMPLE 89

3-chloro-4-[((2R,5S)-5-{[(2S)-2-cyanopyrrolidin-1-yl]carbonyl}pyrrolidin-2-yl)methoxy]-1-naphthoic acid

EXAMPLE 89A

4-Hydroxy-naphthalene-1-carboxylic acid tert-butyl ester

The title compound was synthesized by substituting 3-hydroxypicolinic acid in Example 77A with 4-hydroxy-naphthalene-1-carboxylic acid. MS (ESI) m/z 245 (M+H)$^+$.

EXAMPLE 89B

3-Chloro-4-hydroxy-naphthalene-1-carboxylic acid tert-butyl ester

The title compound was synthesized by substituting 5-hydroxy-nicotinic acid tert-butyl ester in Example 52B with the above ester. MS (ESI) m/z 279, 281 (M+H)+.

EXAMPLE 89C

The title compound was synthesized by substituting 3-tert-butyl-4-hydroxyl-benzoic acid tert-butyl ester in Example 47F with the above ester followed by removal of the Boc group described in Example 1G. $^1$H NMR (400 MHz, MeOH-d$_4$) δ ppm 1.96–2.50 (m, 7H), 2.58–2.80 (m, 1H), 3.63–3.76 (m, 2H), 4.32–4.51 (m, 2H), 4.61 (dd, J=10.59, 8.13 Hz, 1H), 4.75–4.79 (m, 1H), 4.89 (dd, J=7.98, 4.60 Hz, 1H), 7.62–7.77 (m, 2H), 8.25 (s, 1H), 8.29–8.39 (m, 1H), 8.94–9.07 (m, 1H). MS (ESI) m/z 428, 430 (M+H)+.

EXAMPLE 90

3-bromo-4-[((2R,5S)-5-{[(2S)-2-cyanopyrrolidin-1-yl]carbonyl}pyrrolidin-2-yl)methoxy]benzoic acid The title compound was synthesized using the same reaction sequence of Example 80 by substituting 5-chloro-2-hydroxy-benzoic acid in Example 80A with 5-bromo-2-hydroxy-benzoic acid. $^1$H NMR (300 MHz, MeOH-d$_4$) δ ppm 2.02–2.49 (m, 7H), 2.49–2.64 (m, 1H), 3.61–3.77 (m, 2H), 4.20–4.34 (m, 1H), 4.52 (d, J=5.42 Hz, 2H), 4.64–4.73 (m, 1 H), 4.77–4.82 (m, 1H), 7.20 (d, J=8.81 Hz, 1H), 8.03 (dd, J=8.81, 2.03 Hz, 1H), 8.21 (d, J=2.37 Hz, 1H). MS (ESI) m/z 422, 424 (M+H)+.

EXAMPLE 91

6-chloro-5-[((2R,5S)-5-{[(2S)-2-cyanopyrrolidin-1-yl]carbonyl}pyrrolidin-2-yl)methoxy]nicotinic acid 1-oxide The title compound was synthesized by substituting 2S-(2-chloro-pyridin-3-yloxymethyl)-5R-(2S-cyano-pyrrolidine-1-carbonyl)-pyrrolidine-1-carboxylic acid tert-butyl ester (Example 86A) in Example 86B with (2S)-1-{(5R)-5-((5-carboxy-2-chloropyridyl-3-oxy)-methyl)-L-prolyl}-pyrrolidine-2-carbonitrile (Example 52C). $^1$H NMR (500 MHz, DMSO-d$_6$) δ ppm 1.85–1.96 (m, 1H), 1.98–2.10 (m, 4H), 2.11–2.22 (m, 1H), 2.21–2.36 (m, 4 ), 4.49–4.67 (m, 4H), 4.84 (dd, J=7.80, 4.99 Hz, 1H), 7.57 (s, 1H), 8.47 (s, 1H), 8.78 (s, 1H), 9.99 (s, 1H). MS (ESI) m/z 395, 397 (M+H)+.

EXAMPLE 92

6-[((2R,5S)-5-{[(2S)-2-cyanopyrrolidin-1-yl]carbonyl}pyrrolidin-2-yl)methoxy]-2-naphthoic acid The title compound was synthesized by substituting 5-chloro-2-hydroxy-benzoic acid in Example 80 with 6-hydroxy-naphthalene-1-carboxylic acid. $^1$H NMR (400 MHz, MeOH-d$_4$) δ ppm 1.93–2.48 (m, 7H), 2.55–2.70 (m, 1H), 3.61–3.76 (m, 2H), 4.16–4.32 (m, 1H), 4.50–4.59 (m, 2H), 4.72 (dd, J=8.90, 5.83 Hz, 1H), 4.85 (dd, J=7.67, 4.60 Hz, 1H), 7.33 (dd, J=8.90, 2.46 Hz, 1H), 7.42 (d, J=2.15 Hz, 1H), 7.86 (d, J=8.59Hz, 1H), 7.96 (d, J=8.90 Hz, 1H), 8.02 (dd, J=8.75, 1.38 Hz, 1H), 8.55 (s, 1H). MS (ESI) m/z 394 (M+H)+.

EXAMPLE 93

(2S)-1-[((2S,5R)-5-{[2-chloro-4-(methylsulfonyl)phenoxy]methyl}pyrrolidin-2-yl)carbonyl]pyrrolidine-2-carbonitrile

EXAMPLE 93A 2-chloro-4-methanesulfonyl-phenol

4-Methanesulfonylphenol (2.0 g, 11.6 mmol) mixed with 21:14 mL of EtOH:conc HCl was cooled to 0° C., then KClO$_3$ (0.708 g, 5.81 mmol) dissolved in 17 mL of water was added slowly. After reaction overnight, the mixture was extracted with EtOAc and the extracts were concentrated in vacuum. The resulting residue was purified by reverse-phase HPLC to give both 1-chloro-2-methanesulfonyl-4-methoxybenzene and 2-chloro-1-methanesulfonyl-3-methoxy-benzene. MS (DCI) m/z 224 (M+NH$_4$)+.

EXAMPLE 93B (2S)-1-[((2S,5R)-5-{[2-chloro-4-(methylsulfonyl)phenoxy]methyl}pyrrolidin-2-yl)carbonyl]pyrrolidine-2-carbonitrile The title compound was synthesized by substituting 3-tert-butyl-4-hydroxyl-benzoic acid tert-butyl ester in Example 47F with 2-chloro-4-methanesulfonyl-phenol followed by removal of the Boc group described in Example 1G. 1H NMR (500 MHz, MeOH-d4) δ ppm 2.04–2.37 (m, 6H), 2.37–2.45 (m, 1H), 2.55–2.64 (m, J=13.27, 8.09 Hz, 1H), 3.13 (s, 3H), 3.63–3.72 (m, 2 H), 4.21–4.31 (m, 1H), 4.54–4.58 (m, 2H), 4.72 (dd, J=8.85, 5.80 Hz, 1H), 4.83 (dd, J=7.93, 4.58 Hz, 1H), 7.37 (d, J=8.85 Hz, 1H), 7.91 (dd, J=8.54, 2.14 Hz, 1H), 8.00 (d, J=2.44 Hz, 1 H). MS (ESI) m/z 412 (M+H)+.

EXAMPLE 94

(2S)-1-[((2S,5R)-5-{[4-chloro-2-(hydroxymethyl)phenoxy]methyl}pyrrolidin-2-yl)carbonyl]pyrrolidine-2-carbonitrile

EXAMPLE 94A 2-(tert-Butyl-dimethyl-silanyloxymethyl)-4-chlorophenol

4-Chloro-2-hydroxymethyl-phenol (100 mg, 0.6 mmol), TBSCl (104 mg, 0.66 mmol) and imidazol (51.2 mg, 0.72 mmol) were mixed in CH$_2$Cl$_2$. The mixture was stirred for 1 hour and lo concentrated in vacuo. The residue was purified by chromatography on silica gel (hexane/ethyl acetate=5/1) to give the desired product (225 mg, 100%). MS (DCI) m/z 273, 275 (M+H)+.

EXAMPLE 94B

2R-[2-(tert-Butyl-dimethyl-silanyloxymethyl)-4-chloro-phenoxymethyl]-5S-(2S-cyano-pyrrolidine-1-carbonyl)-pyrrolidine-1-carboxylic acid tert-butyl ester The title compound was synthesized by substituting 3-tert-butyl-4-hydroxy-benzoic acid tert-butyl ester in Example 47F with the above phenol. MS (ESI) m/z 578, 580 (M+H)$^+$.

EXAMPLE 94C (2S)-1-[((2S,5R)-5-{[4-chloro-2-(hydroxymethyl)phenoxy]methyl}pyrrolidin-2-yl)carbonyl]pyrrolidine-2-carbonitrile The above compound (100 mg, 0.17 mmol) in THF (1 mL) was treated with TBAF (1M in THF, 0.1 mL). After the reaction was over, the product was purified by reverse phase HPLC to give the desired product. MS (ESI) m/z 464, 466 (M+H)$^+$.

The Boc group was removed according to Example 1G to give the title compound. $^1$H NMR (400 MHz, MeOH-d$_4$) δ ppm 1.97–2.09 (m, 1H), 2.09–2.43 (m, 6H), 2.52–2.65 (m, 1 H), 3.62–3.71 (m, 2H), 4.09–4.22 (m, 1H), 4.29–4.42 (m, 2H), 4.65–4.73 (m, 3H), 4.84 (dd, J=7.67, 4.60 Hz, 1H), 7.02 (d, J=8.90 Hz, 1H), 7.27 (dd, J=8.75, 2.61 Hz, 1H), 7.39 (d, J=2.76 Hz, 1H). MS (ESI) m/z 380, 382 (M+H)$^+$.

EXAMPLE 95

5-chloro-6-[((2R,5S)-5-{[(2S)-2-cyanopyrrolidin-1-yl]carbonyl}pyrrolidin-2-yl)methoxy]-2-naphthoic acid The title compound was synthesized using the same reaction sequence of Example 89 by substituting 4-hydroxy-naphthalene-1-carboxylic acid in Example 89A with 6-hydroxy-naphthalene-2-carboxylic acid. $^1$H NMR (400 MHz, MeOH-d$_4$) δ ppm 2.03–2.51 (m, 7H), 2.56–2.69 (m, 1H), 3.63–3.75 (m, 2H), 4.22–4.35 (m, 1H), 4.58–4.66 (m, 2H), 4.73 (dd, J=8.75, 5.98 Hz, 1H), 4.85 (dd, J=7.52, 4.45 Hz, 1H), 7.60 (d, J=9.21 Hz, 1H), 8.06 (d, J=8.90 Hz, 1 H), 8.15 (dd, J=8.90, 1.53 Hz, 1H), 8.27 (d, J=8.90 Hz, 1H), 8.63 (d, J=1.23 Hz, 1H). MS (ESI) m/z 428, 430 (M+H)$^+$.

EXAMPLE 96

(2S)-1-[((2S,5R)-5-{[(6-chloro-1,3-benzodioxol-5-yl)oxy]methyl}pyrrolidin-2-yl)carbonyl]pyrrolidine-2-carbonitrile

EXAMPLE 96A

6-Chloro-benzo[1,3]dioxol-5-ol

The title compound was synthesized by substituting 5-hydroxy-nicotinic acid tert-butyl ester in Example 52B with sesamol.

EXAMPLE 96B (2S)-1-[((2S,5R)-5-{[(6-chloro-1,3-benzodioxol-5-yl)oxy]methyl}pyrrolidin-2-yl)carbonyl]pyrrolidine-2-carbonitrile The title compound was synthesized by substituting 3-tert-butyl-4-hydroxyl-benzoic acid tert-butyl ester in Example 47F with the above phenol followed by removal of the Boc group described in Example 1G. $^1$H NMR (400 MHz, MeOH-d$_4$) δ ppm 1.96–2.48 (m, 7H), 2.46–2.66 (m, 1H), 3.56–3.74 (m, 2H), 4.10–4.22 (m, 1H), 4.26–4.37 (m, 2H), 4.68 (dd, J=8.75, 5.98 Hz, 1H), 4.85 (dd, J=7.83, 4.45 Hz, 1H), 5.97 (s, 2H), 6.89 (d, J=17.18 Hz, 1H). MS (ESI) m/z 378, 380 (M+H)$^+$.

EXAMPLE 97

N-{4-[((2R,5S)-5-{[(2S)-2-cyanopyrrolidin-1-yl]carbonyl}pyrrolidin-2-yl)methoxy]-1-naphthyl}methanesulfonamide

EXAMPLE 97A 2-(4-Amino-naphthalen-1-yloxymethyl)-5-(2-cyano-pyrrolidine-1-carbonyl)-pyrrolidine-1-carboxylic acid tert-butyl ester The title compound was synthesized by substituting 2-methoxy-4cyanophenol in Example 42 with 4-amino-naphthalen-1-ol HCl salt. MS (ESI) m/z 465 (M+H)$^+$.

EXAMPLE 97B

N-{4-[((2R,5S)-5-{[(2S)-2-cyanopyrrolidin-1-yl]carbonyl}pyrrolidin-2-yl)methoxy]-1-naphthyl}methanesulfonamide The compound of Example 97A (32 mg, 0.07 mmol) was dissolved in CH$_2$Cl$_2$ (1 mL) and pyridine (0.5 mL) in a microwave reaction tube. Methanesulfonyl chloride (6.0 μL, 0.21 mmol) was added. It was reacted under microwave condition at 130° C. for 20 minutes. The mixture was filtered and purified by reverse phase HPLC to give the desired sulfonamide.

The title compound was obtained after removal of the Boc group as described in Example 1G. $^1$H NMR (400 MHz, MeOH-d$_4$) δ ppm 1.98–2.45 (m, 7H), 2.03 (s, 3H), 2.51–2.67 (m, 1 H), 3.59–3.71 (m, 2H), 3.78 (d, J=6.75 Hz, 2H), 4.10–4.26 (m, 1H), 4.65 (dd, J=9.21, 5.52 Hz, 1H), 4.86 (dd, J=7.67, 4.60 Hz, 1H), 6.71 (d, J=8.29 Hz, 1H), 7.33–7.66 (m, 3 h), 8.08 (d, J=8.29 Hz, 1H), 8.15 (d, J=7.98 Hz, 1H). MS (ESI) m/z 443 (M+H)$^+$.

EXAMPLE 98

(2S)-1-[((2S,5R)-5-{[2-bromo-4-(methylsulfonyl)phenoxy]methyl}pyrrolidin-2-yl)carbonyl]pyrrolidine-2-carbonitrile

EXAMPLE 98A 2-bromo-4-methanesulfonyl-phenol

4-Methanesulfonylphenol was brominated using the procedure described in Example 47A. MS (DCI) m/z 252, 254 (M+H)$^+$.

EXAMPLE 98 B (2S)-1-[((2S,5R)-5-}[2-bromo-4-(methylsulfonyl)
phenoxy]methyl}pyrrolidin-2-yl)carbonyl]pyrroli-
dine-2-carbonitrile The title compound was synthesized by substituting 3-tert-butyl-4-hydroxy-benzoic acid tert-butyl ester in Example 47F with 2-chloro-4-methanesulfonyl-phenol followed by removal of the Boc group described in Example 1G. 1H NMR (400 MHz, MeOH-d4) δ ppm 2.06–2.48 (m, 7H), 2.60 (dd, J=13.35, 7.83 Hz, 1H), 3.13 (s, 3H), 3.63–3.73 (m, 2H), 4.24–4.34 (m, 1H), 4.53–4.59 (m, 2H), 4.73 (dd, J=8.44, 5.98 Hz, 1H), 4.82–4.87 (m, 1H), 7.33 (d, J=8.90 Hz, 1 H), 7.95 (dd, J=8.75, 2.30 Hz, 1H), 8.15 (d, J=2.46 Hz, 1H). MS (ESI) m/z 456, 458 (M+H)$^+$.

EXAMPLE 99

(2S)-1-[((2S,5R)-5-{[(6-bromo-1,3-benzodioxol-5-
yl)oxy]methyl}pyrrolidin-2-yl)carbonyl]pyrrolidine-
2-carbonitrile

EXAMPLE 99A 6-bromo-benzo[1,3]dioxol-5-ol

The title compound was synthesized by substituting 3-hydroxy-benzoic acid in Example 52A with sesamol.

EXAMPLE 99

(2S)-1-[((2S,5R)-5-{[(6-bromo-1,3-benzodioxol-5-
yl)oxy]methyl}pyrrolidin-2-yl)carbonyl]pyrrolidine-
2-carbonitrile The title compound was synthesized by substituting 3-tert-butyl-4-hydroxyl-benzoic acid tert-butyl ester in Example 47F with the above phenol followed by removal of the Boc group described in Example 1G. $^1$H NMR (500 MHz, MeOH-d$_4$) δ ppm 1.98–2.06 (m, 1H), 2.12–2.39 (m, 6H), 2.51–2.62 (m, 1H), 3.62–3.72 (m, 2H), 4.08–4.14 (m, 1H), 4.25–4.32 (m, 2 H), 4.61 (dd, J=8.73, 6.24 Hz, 1H), 4.84 (dd, J=7.80, 4.37 Hz, 1H), 5.97 (s, 2H), 6.85 (s, 1H), 7.04 (s, 1H). MS (ESI) m/z 422, 424 (M+H)$^+$.

EXAMPLE 100

2-chloro-N-{3-chloro-4-[((2R,5S)-5-{[(2S)-2-cyan-
opyrrolidin-1-yl]carbonyl}pyrrolidin-2-yl)methoxy]
phenyl}benzenesulfonamide

EXAMPLE 100A

2R-[2-Chloro-4-(2-chloro-benzenesulfonylamino)-
phenoxymethyl]-5S-(2S-cyano-pyrrolidine-1-carbo-
nyl)-pyrrolidine-1-carboxylic acid tert-butyl ester The compound of Example 88B (32 mg, 0.07 mmol) was dissolved in CH$_2$Cl$_2$ (1 mL) and pyridine (0.5 mL) in a microwave reaction tube. 2-Chloro-benzenesulfonyl chloride (6.0 μL, 0.21 mmol) was added. It was reacted under microwave condition at 130° C. for 20 minutes. The mixture was filtered and purified by reverse phase HPLC to provide the title compound (30 mg, 70%). MS (ESI) m/z 623, 625 (M+H)$^+$.

EXAMPLE 100B (2S)-1-[((2S,5R)-5-{[(6-bromo-1,3-benzodioxol-5-
yl)oxy]methyl}pyrrolidin-2-yl)carbonyl]pyrrolidine-
2-carbonitrile The Boc group was removed according to Example 1G to give the title compound. $^1$H NMR (400 MHz, MeOH-d$_4$) δ ppm 1.92–2.05 (m, 1H), 2.07–2.45 (m, 6H), 2.49–260 (m, 1 H), 3.58–3.71 (m, 2H), 4.09–4.18 (m, 1H), 4.31 (d, J=6.14 Hz, 2H), 4.64 (dd, J=8.75, 5.98 Hz, 1H), 4.81–4.85 (m, 1H), 6.97–7.03 (m, 1H), 7.06–7.12 (m, 1H), 7.22 (d, J=2.45 Hz, 1 H), 7.36–7.44 (m, 1H), 7.51–7.59 (m, 2H), 7.99 (dd, J=7.83, 1.38 Hz, 1H). MS (ESI) m/z 523, 525 (M+H)$^+$.

EXAMPLE 101

N-{3-chloro-4-[((2R,5S)-5-{[(2S)-2-cyanopyrroli-
din-1-yl]carbonyl}pyrrolidin-2-yl)methoxy]
phenyl}methanesulfonamide The title compound was synthesized by substituting 2-chloro-benzenesulfonyl chloride in Example 100A with methanesulfonyl chloride. $^1$H NMR (500 MHz, MeOH-d$_4$) δ ppm 1.99–2.11 (m, 1H), 2.11–2.44 (m, 6H), 2.53–2.64 (m, 1H), 3.43 (s, 3H), 3.60–3.73 (m, 2H), 4.16–4.28 (m, 1H), 4.50 (d, J=5.80 Hz, 2H), 4.70 (dd, J=8.70, 5.95 Hz, 1H), 4.81–4.84 (m, J=4.88 Hz, 1H), 7.24 (d, J=8.85 Hz, 1H), 7.42 (dd, J=8.70, 2.59 Hz, 1H), 7.57 (d, J=2.44 Hz, 1H). MS (ESI) m/z 427, 429 (M+H)$^+$.

EXAMPLE 102

N-{3-chloro-4-[((2R,5S)-5-{[(2S)-2-cyanopyrroli-
din-1-yl]carbonyl}pyrrolidin-2-yl)methoxy]
phenyl}acetamide 2R-(4-Amino-2-chloro-phenoxymethyl)-5S-(2S-cyano-pyrrolidine-1-carbonyl)-pyrrolidine-1-carboxylic acid tert-butyl ester (Example 88B) (32 mg, 0.07 mmol) was dissolved in CH$_2$Cl$_2$ (1 mL). Acetyl chloride (6.0 μL, 0.21 mmol) and triethylamine (30 μL, 0.21 mmol) were added. After the reaction was over, it was purified by reverse phase HPLC to provide the desired amide (25 mg, 78%). MS (ESI) m/z 491, 493 (M+H)$^+$.

The Boc group was removed according to Example 1G to give the title compound. $^1$H NMR (400 MHz, MeOH-d$_4$) δ ppm 1.97–2.09 (m, 1H), 2.10 (s, 3H), 2.13–2.45 (m, 6H), 2.59 (dd, J=12.58, 8.59 Hz, 1H), 3.60–3.73 (m, 2H), 4.13–4.26 (m, 1H), 4.39 (d, J=5.22 Hz, 2H), 4.68 (dd, J=8.59, 6.44 Hz, 1H), 4.84 (dd, J=7.67, 4.60 Hz, 1H), 7.12 (d, J=9.21 Hz, 1H), 7.42 (dd, J=8.90, 2.45 Hz, 1H), 7.72 (d, J=2.45 Hz, 1H). MS (ESI) m/z 523, 525 (M+H)$^+$.

EXAMPLE 103

(2S)-1-({(2S,5R)-5-[(1-benzothien-4-yloxy)methyl]pyrrolidin-2-yl}carbonyl)pyrrolidine-2-carbonitrile

EXAMPLE 103A 2R-(Benzo[b]thiophen-4-yloxymethyl)-5S-(2S-cyano-pyrrolidine-1-carbonyl)-pyrrolidine-1-carboxylic acid tert-butyl ester The title compound was synthesized by substituting 3-tert-butyl-4-hydroxy-benzoic acid tert-butyl ester in Example 47F with benzo[b]thiophen-4-ol (*J Am Chem Soc* 1935, 57, 1611).

EXAMPLE 103B (2S)-1-({(2S,5R)-5-[(1-benzothien-4-yloxy)methyl]pyrrolidin-2-yl}carbonyl)pyrrolidine-2-carbonitrile The above ether (50 mg) was treated with 2 mL of 4N HCl in isopropanol (prepared by diluting 2 mL of conc HCl to 6 mL with isopropanol) at room temperature for 4 hours. Purification by reverse HPLC [0–70% $CH_3CN/H_2O$ with 0.1% trifluoroacetic acid (TFA) in aq. eluent] gave the title compound. $^1$H NMR (400 MHz, MeOH-$d_4$) δ ppm 2.06–2.46 (m, 8H), 2.56–2.69 (m, 1H), 3.63–3.75 (m, 2H), 4.20–4.31 (m, 1H), 4.49–4.56 (m, J=5.52 Hz, 2H), 4.74 (dd, J=8.90, 5.52 Hz, 1H), 4.87 (dd, J=7.83, 4.45 Hz, 1H), 6.92 (d, J=7.98 Hz, 1H), 7.31 (t, J=7.98 Hz, 1H), 7.48 (d, J=5.52 Hz, 1H), 7.54 (d, J=7.98 Hz, 1H), 7.67 (d, J=5.52 Hz, 1H). MS (ESI) m/z 356 (M+H)$^+$.

EXAMPLE 104

(2S)-1-[((2S,5R)-5-{[4-bromo-2-(methylsulfonyl)phenoxy]methyl}pyrrolidin-2-yl)carbonyl]pyrrolidine-2-carbonitrile

EXAMPLE 104A

2-Methanesulfonyl-phenol

2-Methylsulfanyl-phenol (1 g, 7.1 mmol) and mCPBA (8 g, 77%, 35.5 mmol) were mixed in $CH_2Cl_2$. The reaction was stirred over night and purified by silica gel chromatography to provide the title compound (900 mg, 75%). MS (DCI) m/z 173 (M+H)$^+$.

EXAMPLE 104

(2S)-1-[((2S,5R)-5-{[4-bromo-2-(methylsulfonyl)phenoxy]methyl-pyrrolidin-2-yl)carbonyl]pyrrolidine-2-carbonitrile The title compound was synthesized using the same reaction sequence of Example 56 by substituting 3-hydroxy benzoic acid in Example 56A with 2-methanesulfonyl-phenol and the rest of the reaction sequence. $^1$H NMR (500 MHz, MeOH-$d_4$) δ ppm 2.07–2.43 (m, 7H), 2.54–2.68 (m, 1H), 3.31 (s, 3H), 3.61–3.72 (m, 2H), 4.21–4.32 (m, 1H), 4.46–4.53 (m, 1H), 4.61 (dd, J=10.61, 3.43 Hz, 1H), 4.73 (dd, J=9.05, 5.62 Hz, 1H), 4.82 (dd, J=7.80, 4.37 Hz, 1H), 7.31 (d, J=9.05 Hz, 1H), 7.86 (dd, J=8.89, 2.65 Hz, 1H), 8.02 (d, J=2.50 Hz, 1H). MS (ESI) m/z 456, 458 (M+H)$^+$.

EXAMPLE 105

6-[((2R,5S)-5-{[(2S)-2-cyanopyrrolidin-1-yl]carbonyl}pyrrolidin-2-yl)methoxy]-1-naphthoic acid The title compound was synthesized by substituting 3-hydroxypicolinic acid in Example 77A with 6-hydroxy-naphthalene-1-carboxylic acid and the rest of the reaction sequence. $^1$H NMR (500 MHz, MeOH-$d_4$) δ ppm 2.00–2.12 (m, 1H), 2.11–2.45 (m, 6H), 2.56–2.68 (m, 1H), 3.62–3.74 (m, 2H), 4.18–4.26 (m, 1H), 4.50–4.54 (m, 2H), 4.72 (dd, J=9.05, 5.62 Hz, 1H), 4.85 (dd, J=7.95, 4.52 Hz, 1H), 7.35 (dd, J=9.51, 2.65 Hz, 1H), 7.43 (d, J=2.50 Hz, 1H), 7.51 (dd, J=8.11, 7.49 Hz, 1H), 8.02 (d, J=8.42 Hz, 1H), 8.09 (dd, J=7.33, 1.40 Hz, 1H), 8.89 (d, J=9.67 Hz, 1H). MS (ESI) m/z 394 (M+H)$^+$.

EXAMPLE 106

N-{3-bromo-4-[((2R,5S)-5-{[(2S)-2-cyanopyrrolidin-1-yl]carbonyl}pyrrolidin-2-yl)methoxy]phenyl}acetamide

EXAMPLE 106A 2R-(4-Amino-2-bromo-phenoxymethyl)-5S-(2S-cyano-pyrrolidine-1-carbonyl)-pyrrolidine-1-carboxylic acid tert-butyl ester The title compound was synthesized by substituting 2-chloro-4-nitro-phenol in Example 88A with 2-bromo-4-nitro-phenol and subsequent reduction of the nitro group as described in Example 88B. MS (ESI) m/z 493, 495 (M+H)$^+$.

EXAMPLE 106B

The title compound was synthesized by substituting 2R-(4-amino-2-chloro-phenoxymethyl)-5S-(2S-cyano-pyrrolidine-1-carbonyl)-pyrrolidine-1-carboxylic acid tert-butyl ester in Example 102 with the above amine followed by the removal of the Boc group according to Example 1G. $^1$H NMR (500 MHz, MeOH-$d_4$) δ ppm 2.03–2.10 (m, 1H), 2.09–2.12 (s, 3H), 2.12–2.46 (m, 6H), 2.52–2.65 (m, 1H), 3.56–3.77 (m, 2H), 4.14–4.26 (m, 1H), 4.35–4.43 (m, 2H), 4.68 (dd, J=8.54, 6.10 Hz, 1H), 4.80–4.87 (m, 1H), 7.10 (d, J=8.85 Hz, 1H), 7.48 (dd, J=8.85, 2.75 Hz, 1H), 7.88 (d, J=2.44 Hz, 1H). MS (ESI) m/z 435, 437 (M+H)$^+$.

EXAMPLE 107

N-{3-bromo-4-[((2R,5S)-5-{[(2S)-2-cyanopyrrolidin-1-yl]carbonyl}pyrrolidin-2-yl)methoxy]phenyl}methanesulfonamide

EXAMPLE 107A

The compound of Example 106A (34 mg, 0.07 mmol) was dissolved in $CH_2Cl_2$ (1 mL) and pyridine (0.5 mL) in a microwave reaction tube. Methanesulfonyl chloride (6.0 μL, 0.21 mmol) was added. The mixture was heated to 130° C. in a microwave reactor and kept for 20 minutes. The mixture was filtered and purified by reverse phase HPLC to provide the title compound (30 mg, 70%). MS (ESI) m/z 571, 573 (M+H)$^+$.

EXAMPLE 107B

N-{3-bromo-4-[((2R,5S)-5-{[(2S)-2-cyanopyrrolidin-1-yl]carbonyl}pyrrolidin-2-yl)methoxy]phenyl}methanesulfonamide The Boc group was removed according to Example 1G to give the title compound. $^1$H NMR (500 MHz, MeOH-$d_4$) δ ppm 2.01–2.44 (m, 7H), 2.54–2.67 (m, 1H), 2.93 (s, 3H), 3.61–3.73 (m, 2H), 4.14–4.28 (m, 1H), 4.35–4.46 (m, 2H), 4.70 (dd, J=8.89, 6.08 Hz, 1H), 4.84 (dd, J=7.80, 4.37 Hz, 1H), 7.13 (d, J=8.73 Hz, 1H), 7.27 (dd, J=8.73, 2.50 Hz, 1 H), 7.51 (d, J=2.50 Hz, 1H). MS (ESI) m/z 471, 473 (M+H)$^+$.

EXAMPLE 108

N-{3-bromo-4-[((2R,5S)-5-{[(2S)-2-cyanopyrrolidin-1-yl]carbonyl}pyrrolidin-2-yl)methoxy]phenyl}benzenesulfonamide The title compound was synthesized by substituting methanesulfonyl chloride in Example 107A with phenyl sulfonyl chloride followed by the removal of the Boc group as described in Example 1G. $^1$H NMR (500 MHz, MeOH-$d_4$) δ ppm 2.00–2.08 (m, 1H), 2.10–2.39 (m, 6H), 2.52–2.63 (m, 1H), 3.61–3.72 (m, 2H), 4.14–4.21 (m, 1H), 4.30–4.37 (m, 2H), 4.66 (dd, J=8.58, 6.08 Hz, 1H), 4.83 (dd, J=7.96, 4.52 Hz, 1H), 6.98–7.02 (m, 1H), 7.07 (dd, J=8.73, 2.50 Hz, 1H), 7.29 (d, J=2.81 Hz, 1H), 7.49 (t, J=7.64 Hz, 2H), 7.58 (t, J=7.33 Hz, 1H), 7.72 (dd, J=8.42, 1.25 Hz, 2H). MS (ESI) m/z 533, 535 (M+H)$^+$.

EXAMPLE 109

N-{3-bromo-4-[((2R,5S)-5-{[(2S)-2-cyanopyrrolidin-1-yl]carbonyl}pyrrolidin-2-yl)methoxy]phenyl}-2-chlorobenzenesulfonamide The title compound was synthesized by substituting methanesulfonyl chloride in Example 107A with 2-chloro-benzenesulfonyl chloride followed by the removal of the Boc group as described in Example 1G. $^1$H NMR (500 MHz, MeOH-$d_4$) δ ppm 2.00–2.06 (m, 1H), 2.10–2.38 (m, 6H), 2.50–2.61 (m, J=12.95, 7.96 Hz, 1H), 3.59–3.70 (m, 2H), 4.09–4.20 (m, 1H), 4.27–4.35 (m, 2H), 4.65 (dd, J=8.74, 6.24 Hz, 1H), 4.82 (dd, J=7.95, 4.52 Hz, 1 H), 6.98 (d, J=8.73 Hz, 1H), 7.14 (dd, J=8.89, 2.65 Hz, 1H), 7.36–7.44 (m, 2H), 7.51–7.61 (m, 2H), 7.98 (dd, J=7.95, 1.40 Hz, 1H). MS (ESI) m/z 567, 569 (M+H)$^+$.

EXAMPLE 110 methyl 2,3-dichloro-4-[((2R,5S)-5-{[(2S)-2-cyanopyrrolidin-1-yl]carbonyl}pyrrolidin-2-yl)methoxy]benzoate

EXAMPLE 110A 2,3-dichloro-4-hydroxy-benzoic acid methyl ester

The title compound was synthesized by substituting 1-benzyloxy-4-bromo-2-tert-butyl-benzene in Example 47C with 2,3-dichloro-4-bromobenzene. MS (ESI) m/z −219, −211 (M−H)$^-$.

EXAMPLE 110B methyl 2,3-dichloro-4-[((2R,5S)-5-{[(2S)-2-cyanopyrrolidin-1-yl]carbonyl}pyrrolidin-2-yl)methoxy]benzoate The title compound was synthesized by substituting 3-tert-butyl-4-hydroxy-benzoic acid tert-butyl ester in Example 47F with 2,3dichloro-4-hydroxy-benzoic acid methyl ester followed by removal of the Boc group described in Example 103B. $^1$H NMR (500 MHz, MeOH-$d_4$) δ ppm 2.03–2.37 (m, 6H), 2.37–2.45 (m, 1H), 2.54–2.63 (m, J=13.26, 7.96 Hz, 1H), 3.63–3.72 (m, 2H), 3.90 (s, 3H), 4.22–4.30 (m, J=6.71, 6.71 Hz, 1H), 4.51–4.56 (m, 2H), 4.71 (dd, J=8.73, 5.93 Hz, 1H), 4.84 (dd, J=7.95, 4.21 Hz, 1H), 7.20 (d, J=9.05 Hz, 1H), 7.84 (d, J=8.73 Hz, 1 H). MS (ESI) m/z 426 (M+H)$^+$.

EXAMPLE 111

3-[((2R,5S)-5-{[(2S)-2-cyanopyrrolidin-1-yl]carbonyl}pyrrolidin-2-yl)methoxy]-4-methoxybenzoic acid

EXAMPLE 111A 3-hydroxy-4-methoxy-benzoic acid tert-butyl ester

The title compound was synthesized by substituting 3-hydroxypicolinic acid in Example 77A with 4-methoxy-3-hydroxy-benzoic acid. MS (DCI) m/z 225(M+H)$^+$.

EXAMPLE 111B

3-[((2R,5S)-5-{[(2S)-2-cyanopyrrolidin-1-yl]carbonyl}pyrrolidin-2-yl)methoxy]-4-methoxybenzoic acid The title compound was synthesized by substituting 3-tert-butyl-4-hydroxy-benzoic acid tert-butyl ester in Example 47F with 3-hydroxy-4-methoxy-benzoic acid tert-butyl ester followed by removal of the Boc group described in Example 103B. $^1$H NMR (400 MHz, MeOH-$d_4$) δ ppm 1.98–2.09 (m, 1H), 2.11–2.41 (m, 7H), 2.53–2.67 (m, J=12.73, 8.75 Hz, 1H), 3.63–3.72 (m, 2H), 3.96 (s, 3H), 4.12–4.22 (m, 1H), 4.30–4.44 (m, 2H), 4.68 (dd, J=8.90, 6.44 Hz, 1H), 4.85 (dd, J=7.98, 4.30 Hz, 1H), 7.08–7.15 (m, 1H), 7.68 (d, J=2.15 Hz, 1H), 7.78 (dd, J=8.44, 1.99 Hz, 1H). MS (ESI) m/z 374 (M+H)$^+$.

EXAMPLE 112

2,3-dichloro-4-[((2R,5S)-5-{[(2S)-2-cyanopyrrolidin-1-yl]carbonyl}pyrrolidin-2-yl)methoxy]benzoic acid

EXAMPLE 112A 2,3-dichloro-4-hydroxy-benzoic acid tert-butyl ester

The title compound was synthesized by substituting 4-benzyloxy-3-tert-butyl-benzoic acid methyl ester in Example 47D with 2,3dichloro-4-hydroxy-benzoic acid methyl ester (made in Example 110A).

EXAMPLE 112B 2R-(4-tert-butoxycarbonyl-2,3-dichloro-phenoxymethyl)-5S-(2S-cyano-pyrrolidine-1-carbonyl)-pyrrolidine-1-carboxylic acid tert-butyl ester The title compound was synthesized by substituting 3-tert-butyl-4-hydroxy-benzoic acid tert-butyl ester in Example 47F with the above tert-butyl ester.

EXAMPLE 112C 2,3-dichloro-4-[((2R,5S)-5-{[(2S)-2-cyanopyrrolidin-1-yl]carbonyl}pyrrolidin-2-yl)methoxy]benzoic acid The Boc and tert-butyl groups were removed by procedure described in Example 103B. $^1$H NMR (500 MHz, MeOH-$d_4$) δ ppm 2.03–2.12 (m, 1H), 2.13–2.45 (m, 6H), 2.55–2.64 (m, 1H), 3.62–3.74 (m, 2H), 4.22–4.30 (m, 1H), 4.50–4.55 (m, J=1.25 Hz, 2 H), 4.72 (dd, J=8.73, 5.93 Hz, 1H), 4.84 (none, 1H), 7.19 (d, J=8.73 Hz, 1H), 7.87 (d, J=8.74 Hz, 1H). MS (ESI) m/z 412 (M+H)$^+$.

EXAMPLE 113

(2S)-1-({(2S,5R)-5-[(2,4-dichloro-5-nitrophenoxy)methyl]pyrrolidin-2-yl}carbonyl)pyrrolidine-2-carbonitrile

EXAMPLE 113A 2S-(2S-Cyano-pyrrolidine-1-carbonyl)-5R-(2,4-dichloro-5-nitro-phenoxymethyl)-pyrrolidine-1-carboxylic acid tert-butyl ester The title compound was synthesized by substituting 3-tert-butyl-4-hydroxy-benzoic acid tert-butyl ester in Example 47F with 2,4dichloro-5-nitrophenol.

EXAMPLE 113B (2S)-1-({(2S,5R)-5-[(2,4-dichloro-5-nitrophenoxy)methyl]pyrrolidin-2-yl}carbonyl)pyrrolidine-2-carbonitrile The Boc group of the above ether was removed according to Example 103B. $^1$H NMR (400 MHz, MeOH-$d_4$) δ ppm 2.03–2.45 (m, 8H), 2.54–2.66 (m, 1H), 3.63–3.72 (m, 2H), 4.21–4.31 (m, 1H), 4.48–4.57 (m, 2H), 4.72 (dd, J=8.59, 6.14 Hz, 1H), 4.81–4.87 (m, 1H), 7.80 (d, J=1.23 Hz, 2H). MS (ESI) m/z 413 (M+H)$^+$.

EXAMPLE 114 tert-butyl 2,3-dichloro-4-[((2R,5S)-5-{[(2S)-2-cyanopyrrolidin-1-yl]carbonyl}pyrrolidin-2-yl)methoxy]benzoate The title compound was synthesized when only the Boc group in Example 112B was removed. $^1$H NMR (500 MHz, MeOH-$d_4$) δ ppm 1.59 (s, 9H), 2.04–2.11 (m, J=13.26, 8.27 Hz, 1H), 2.13–2.45 (m, 6H), 2.59 (dd, J=13.26, 7.64 Hz, 1H), 3.62–3.72 (m, 2H), 4.22–4.30 (m, 2H), 4.52 (d, J=4.99 Hz, 1H), 4.71 (dd, J=8.73, 5.93 Hz, 1H), 4.84 (dd, J=7.95, 4.21 Hz, 1H), 7.18 (d, J=8.73 Hz, 1H), 7.70 (d, J=8.74 Hz, 1H). MS (ESI) m/z 468(M+H)$^+$.

EXAMPLE 115 ethyl 4-chloro-3-[((2R,5S)-5-{[(2S)-2-cyanopyrrolidin-1-yl]carbonyl}pyrrolidin-2-yl)methoxy]benzoate The title compound was synthesized by substituting 3-tert-butyl-4-hydroxy-benzoic acid tert-butyl ester in Example 47F with 4chloro-3-hydroxy-benzoic acid ethyl ester followed by removal of the Boc group described in Example 103B. $^1$H NMR (500 MHz, MeOH-$d_4$) δ ppm 1.39 (t, J=7.18 Hz, 3H), 2.06–2.45 (m, 7H), 2.56–2.65 (m, J=13.26, 8.27 Hz, 1H), 3.63–3.72 (m, 2H), 4.21–4.29 (m, J=8.42, 4.06 Hz, 1H), 4.38 (q, J=7.18 Hz, 2H), 4.47–4.55 (m, 2H), 4.70 (dd, J=8.73, 6.24 Hz, 1H), 4.84 (dd, J=7.95, 4.21 Hz, 1H), 7.54 (d, J=8.11 Hz, 1H), 7.68 (dd, J=8.42, 1.87 Hz, 1H), 7.74 (d, J=1.56 Hz, 1H). MS (ESI) m/z 406 (M+H)$^+$.

EXAMPLE 116 isopropyl 4-chloro-3-[((2R,5S)-5-{[(2S)-2-cyanopyrrolidin-1-yl]carbonyl}pyrrolidin-2-yl)methoxy]benzoate

EXAMPLE 116A 4-chloro-3-hydroxy-benzoic acid isopropyl ester

4-Chloro-3-hydroxy-benzoic acid (100 mg, 0.58 mmol) and 1 mL of isopropanol were mixed and then heated to 85° C. for overnight. The mixture was then concentrated in vacuum and the resulting residue was purified by flash chromatography (8–20% EtOAc/Hex) to give the desired ester (94 mg, 75%). MS (DCI) m/z 215 (M+H)$^+$, 232 (M+NH$_4$)$^+$.

EXAMPLE 116B isopropyl 4-chloro-3-[((2R,5S)-5-{[(2S)-2-cyanopyrrolidin-1-yl]carbonyl}pyrrolidin-2-yl)methoxy]benzoate The title compound was synthesized by substituting 3-tert-butyl-4-hydroxy-benzoic acid tert-butyl ester in Example 47F with 4-chloro-3-hydroxy-benzoic acid isopropyl ester followed by removal of the Boc group described in Example 103B. $^1$H NMR (500 MHz, MeOH-$d_4$) δ ppm 1.37 (d, J=6.24 Hz, 6H), 2.05–2.46 (m, 7H), 2.56–2.63 (m, 1H), 3.63–3.72 (m, 2H), 4.22–4.29 (m, 1H), 4.47–4.55 (m, 2H), 4.71 (dd, J=8.73, 5.93 Hz, 1H), 4.84 (dd, J=7.96, 4.52 Hz, 1 H), 5.18–5.27 (m, J=6.24, 6.24, 6.24, 6.24, 6.24, 6.24 Hz, 1H), 7.53 (d, J=8.42 Hz, 1H), 7.66 (dd, J=8.27, 1.72 Hz, 1H), 7.72 (d, J=1.87 Hz, 1H). MS (ESI) m/z 420 (M+H)$^+$.

EXAMPLE 117

N-{2,4-dichloro-5-[((2R,5S)-5-{[(2S)-2-cyanopyrrolidin-1-yl]carbonyl}pyrrolidin-2-yl)methoxy]phenyl}acetamide

EXAMPLE 117A 2-(5-Amino-2,4-dichloro-phenoxymethyl)-5-(2-cyano-pyrrolidine-1-carbonyl)-pyrrolidine-1-carboxylic acid tert-butyl ester 2S-(2S-Cyano-pyrrolidine-1-carbonyl)-5R-(2,4-dichloro-5-nitro-phenoxymethyl)-pyrrolidine-1-carboxylic acid tert-butyl ester (from Example 113A) (934 mg, 1.82 mmol), iron powder (708 mg, 12.7 mmol), NH₄Cl (68 mg, 1.27 mmol) were mixed in 5.5:1.9 mL of EtOH:H₂O and the mixture was heated to 70° C. After 2 hours, EtOAc was added and the mixture was filtered through Celite. The filtrate was concentrated in vacuum and the resulting residue was used directly in the next step. MS (ESI) m/z 483 (M+H)$^+$.

EXAMPLE 117B 2-(5-Acetylamino-2,4-dichloro-phenoxymethyl)-5-(2-cyano-pyrrolidine-1-carbonyl)-pyrrolidine-1-carboxylic acid tert-butyl ester To the above amine (0.1 mmol) and Et₃N (0.4 mmol) in dichloromethane was added acetyl chloride (0.25 mmol). After the reaction was complete, the mixture was quenched by water (50 μL) and acetonitrile (c.a. 1 mL) was added. The mixture was then purified by reverse-phase HPLC to give the desired product, which is used in the next step without characterization.

EXAMPLE 117C

N-{2,4-dichloro-5-[((2R,5S)-5-{[(2S)-2-cyanopyrrolidin-1-yl]carbonyl}pyrrolidin-2-yl)methoxy]phenyl}acetamide The Boc group was removed as described in Example 103B to give the title compound. $^1$H NMR (500 MHz, MeOH-d₄) δ ppm 2.01–2.10 (m, 1H), 2.12–2.19 (m, 1H), 2.21 (s, 3H), 2.22–2.44 (m, 5H), 2.53–2.64 (m, 1H), 3.61–3.72 (m, 2H), 4.17–4.25 (m, 1H), 4.39–4.46 (m, 2H), 4.68 (dd, J=8.85, 6.10 Hz, 1H), 4.81–4.84 (m, 1H), 7.53 (s, 1H), 7.74 (s, 1H). MS (ESI) m/z 425 (M+H)$^+$.

EXAMPLE 118

N-{2,4-dichloro-5-[((2R,5S)-5-{[(2S)-2-cyanopyrrolidin-1-yl]carbonyl}pyrrolidin-2-yl)methoxy]phenyl}acrylamide The title compound was synthesized by substituting acetyl chloride in 117B with acryloyl chloride. $^1$H NMR (500 MHz, MeOH-d₄) δ ppm 2.02–2.44 (m, 7H), 2.54–2.64 (m, J=13.10, 8.42 Hz, 1H), 3.63–3.72 (m, 2H), 4.19–4.26 (m, 1H), 4.42–4.48 (m, 2H), 4.69 (dd, J=8.73, 6.24 Hz, 1H), 4.84 (dd, J=7.80, 4.37 Hz, 1H), 5.85 (dd, J=10.29, 1.56 Hz, 1H), 6.43 (ddd, 1H), 6.59 (dd, J=17.00, 10.14 Hz, 1H), 7.55 (s, 1H), 7.85 (s, 1H). MS (ESI) m/z 437 (M+H)$^+$.

EXAMPLE 119

N-{2,4-dichloro-5-[((2R,5S)-5-{[(2S)-2-cyanopyrrolidin-1-yl]carbonyl}pyrrolidin-2-yl)methoxy]phenyl}benzamide The title compound was synthesized by substituting acetyl chloride in Example 107B with benzoyl chloride followed by removal of the Boc group described in Example 103B. $^1$H NMR (500 MHz, MeOH-d₄) δ ppm 2.04–2.46 (m, 7H), 2.55–2.65 (m, 1H), 3.63–3.73 (m, 2 H), 4.20–4.29 (m, 1H), 4.44–4.53 (m, 2H), 4.70 (dd, J=8.74, 6.24 Hz, 1H), 4.84 (dd, J=7.80, 4.37 Hz, 1H), 7.55 (t, J=7.64 Hz, 2H), 7.58–7.67 (m, 2H), 7.78 (s, 1H), 7.98 (d, J=7.18 Hz, 2 H). MS (ESI) m/z 487 (M+H)$^+$.

EXAMPLE 120

N-{2,4-dichloro-5-[((2R,5S)-5-{[(2S)-2-cyanopyrrolidin-1-yl]carbonyl}pyrrolidin-2-yl)methoxy]phenyl}-2-methoxyacetamide The title compound was synthesized by substituting acetyl chloride in Example 107B with methoxyacetyl chloride followed by removal of the Boc group described in Example 103B. $^1$H NMR (500 MHz, MeOH-d₄) δ ppm 2.02–2.44 (m, 7H), 2.54–2.63 (m, J=13.26, 8.27 Hz, 1 H), 3.54 (s, 3H), 3.62–3.71 (m, 2H), 4.10 (s, 2H), 4.19–4.26 (m, J=8.42, 4.37 Hz, 1H), 4.41–4.49 (m, 2H), 4.69 (dd, J=8.74, 6.24 Hz, 1H), 4.84 (dd, J=7.95, 4.21 Hz, 1H), 7.55 (s, 1H), 8.09 (s, 1H). MS (ESI) m/z 455 (M+H)$^+$.

EXAMPLE 121

N-{2,4-dichloro-5-[((2R,5S)-5-{[(2S)-2-cyanopyrrolidin-1-yl]carbonyl}pyrrolidin-2-yl)methoxy]phenyl}-2-(2-methoxyethoxy)acetamide The title compound was synthesized by substituting acetyl chloride in Example 107B with (2-methoxy-ethoxy)-acetyl chloride followed by removal of the Boc group described in Example 103B. $^1$H NMR (500 MHz, MeOH-d₄) δ ppm 2.07 (dd, J=13.12, 8.54 Hz, 1H), 2.12–2.44 (m, 7H), 2.54–2.63 (m, J=13.27, 8.39 Hz, 1H), 3.39 (s, 3H), 3.62–3.65 (m, 2H), 3.65–3.72 (m, 2H), 3.78–3.82 (m, 2H), 4.20 (s, 2H), 4.21–4.25 (m, 1H), 4.41–4.48 (m, 2H), 4.69 (dd, J=8.70, 5.95 Hz, 1H), 4.81–4.84 (m, 1H), 7.56 (s, 1H), 8.11 (s, 1H). MS (ESI) m/z 499 (M+H)$^+$.

EXAMPLE 122

N-{2,4-dichloro-5-[((2R,5S)-5-{[(2S)-2-cyanopyrrolidin-1-yl]carbonyl}pyrrolidin-2-yl)methoxy]phenyl}cyclopropanecarboxamide The title compound was synthesized by substituting acetyl chloride in Example 107B with cyclopropanecarbonyl chloride followed by removal of the Boc group described in Example 103B. $^1$H NMR (500 MHz, MeOH-d₄) δ ppm 0.89–0.95 (m, 2H), 0.96–1.02 (m, 2 H), 1.92–1.99 (m, 1H), 2.01–2.11 (m, 1H), 2.12–2.43 (m, 6H), 2.54–2.63 (m, 1H), 3.63–3.71 (m, 2 H), 4.18–4.24 (m, 1H), 4.39–4.45 (m, 2H), 4.69 (dd, J=8.73, 6.24 Hz, 1H), 4.84 (dd, J=7.95, 4.52 Hz, 1H), 7.52 (s, 1H), 7.76 (s, 1H). MS (ESI) m/z 451(M+H)$^+$.

EXAMPLE 123 ethyl 2,4-dichloro-5-[((2R,5S)-5-{[(2S)-2-cyanopyrrolidin-1-yl]carbonyl}pyrrolidin-2-yl)methoxy]phenylcarbamate The title compound was synthesized by substituting acetyl chloride in Example 107B with ethyl chloroformate followed by removal of the Boc group described in Example 103B. $^1$H NMR (500 MHz, MeOH-d₄) δ ppm 1.33 (t, J=7.02 Hz, 3H), 2.07 (dd, J=13.12, 8.24 Hz, 1H), 2.13–2.44 (m, 6H), 2.54–2.63 (m, J=13.12, 8.24 Hz, 1H), 3.62–3.71 (m, 2H), 4.18–4.21 (m, 1H), 4.24 (q, J=7.22 Hz, 2H), 4.40–4.47 (m, 2H), 4.69 (dd, J=8.70, 6.26 Hz, 1H), 4.82–4.83 (m, 1H), 7.48 (s, 1H), 7.78 (s, 1H). MS (ESI) m/z 455 (M+H)$^+$.

EXAMPLE 124

(2S)-1-({(2S,5R)-5-[(5-(bis(methanesulfonyl))amino-2,4-dichlorophenoxy)methyl]pyrrolidin-2-yl}carbonyl)pyrrolidine-2-carbonitrile The title compound was synthesized by substituting acetyl chloride in Example 107B with methanesulfonyl chloride followed by removal of the Boc group described in Example 103B. $^1$H NMR (500 MHz, MeOH-$d_4$) δ ppm 2.02–2.12 (m, 1H), 2.13–2.44 (m, 6 H), 2.59 (ddd, J=16.25, 13.20, 8.39 Hz, 1H), 3.53 and 3.57 (s, 6H), 3.62–3.72 (m, 2H), 4.20–4.28 (m, J=6.87, 6.87 Hz, 1H), 4.51 (d, J=5.80 Hz, 2H), 4.71 (dd, J=8.70, 5.95 Hz, 1H), 4.81–4.83 (m, 1H), 7.39 (s, 1H), 7.73 (s, 1H). MS (ESI) m/z 539 (M+H)$^+$.

EXAMPLE 125

N-{2,4-dichloro-5-[((2R,5S)-5-{[(2S)-2-cyanopyrrolidin-1-yl]carbonyl}pyrrolidin-2-yl)methoxy]phenyl}-1-phenylmethanesulfonamide The title compound was synthesized by substituting acetyl chloride in Example 107B with benzylsulfonyl chloride followed by removal of the Boc group described in Example 103B. $^1$H NMR (500 MHz, MeOH-$d_4$) δ ppm 2.03 (s, 2H), 2.04–2.09 (m, 1H), 2.12–2.43 (m, 6H), 2.53–2.62 (m, J=13.12, 8.24 Hz, 1H), 3.62–3.73 (m, 2H), 4.14–4.25 (m, 2H), 4.52 (s, 2H), 4.70 (dd, J=8.70, 5.95 Hz, 1H), 4.82–4.84 (m, 1H), 6.94 (s, 1H), 7.32–7.41 (m, 5H), 7.48 (s, 1H). MS (ESI) m/z 537(M+H)$^+$.

EXAMPLE 126

N-{2,4-dichloro-5-[((2R,5S)-5-{[(2S)-2-cyanopyrrolidin-1-yl]carbonyl}pyrrolidin-2-yl)methoxy]phenyl}-N'-phenylurea The title compound was synthesized by substituting acetyl chloride in Example 107B with phenylisocyanate followed by removal of the Boc group described in Example 103B. $^1$H NMR (500 MHz, MeOH-$d_4$) δ ppm 2.04–2.45 (m, 8H), 2.54–2.64 (m, 1H), 3.61–3.73 (m, 2 H), 4.22 (dd, J=8.39, 4.42 Hz, 1H), 4.42–4.51 (m, 2H), 4.68 (dd, J=8.54, 6.41 Hz, 1H), 4.81–4.82 (m, 1H), 7.06 (t, J=7.48 Hz, 1H), 7.31 (t, J=7.93 Hz, 2H), 7.43–7.51 (m, 3H), 8.14 (s, 1 H). MS (ESI) m/z 502 (M+H)$^+$.

EXAMPLE 127

N-{2,4-dichloro-5-[((2R,5S)-5-{[(2S)-2-cyanopyrrolidin-1-yl]carbonyl}pyrrolidin-2-yl)methoxy]phenyl}-N'-(3,5-dimethoxyphenyl)urea The title compound was synthesized by substituting acetyl chloride in Example 107B with 3,5-dimethoxyphenylisocyanate followed by removal of the Boc group described in Example 103B. $^1$H NMR (500 MHz, MeOH-$d_4$) δ ppm 2.04–2.45 (m, 8H), 2.54–2.63 (m, 1H), 3.62–3.73 (m, 2H), 3.77 (s, 6H), 3.87 (d, J=2.14 Hz, 1H), 4.18–4.26 (m, 1H), 4.43–4.51 (m, 2H), 4.69 (dd, J=8.70, 6.26 Hz, 1H), 4.80–4.84 (m, 1H), 6.22 (t, J=2.14 Hz, 1H), 6.69 (d, J=1.83 Hz, 2H), 7.47 (s, 1H), 8.13 (s, 1H). MS (ESI) m/z 562 (M+H)$^+$.

EXAMPLE 128

N-{2,4-dichloro-5-[((2R,5S)-5-{[(2S)-2-cyanopyrrolidin-1-yl]carbonyl}pyrrolidin-2-yl)methoxy]phenyl}-N'-(4-nitrophenyl)urea The title compound was synthesized by substituting acetyl chloride in Example 107B with 5-nitrophenylisocyanate followed by removal of the Boc group described in Example 103B. $^1$H NMR (500 MHz, MeOH-$d_4$) δ ppm 2.06–2.46 (m, 8H), 2.55–2.65 (m, 1H), 3.62–3.73 (m, 2H), 4.19–4.27 (m, 1H), 4.44–4.53 (m, 2H), 4.69 (dd, J=8.70, 6.26 Hz, 1H), 4.82–4.84 (m, 1H), 7.50 (s, 1H), 7.54 (t, J=8.09 Hz, 1H), 7.65 (dd, J=7.93, 1.22 Hz, 1H), 7.90 (dd, J=8.09, 1.37 Hz, 1H), 8.19 (s, 1H), 8.66 (t, J=2.14 Hz, 1H). MS (ESI) m/z 547 (M+H)$^+$.

EXAMPLE 129

(2S)-1-({(2S,5R)-5-[(5-amino-2,4-dichlorophenoxy)methyl]pyrrolidin-2-yl}carbonyl)pyrrolidine-2-carbonitrile The Boc group in 2R-(5-amino-2,4-dichloro-phenoxymethyl)-5S-(2S-cyano-pyrrolidine-1-carbonyl)-pyrrolidine-1-carboxylic acid tert-butyl ester (made in Example 107A) was removed according to the procedure described in Example 103B to give the title compound. $^1$H NMR (500 MHz, MeOH-$d_4$) δ ppm 1.97–2.07 (m, 1H), 2.11–2.44 (m, 7H), 2.51–2.63 (m, 1 H), 3.61–3.71 (m, 2H), 4.15–4.23 (m, 1H), 4.32–4.36 (m, 2H), 4.69 (dd, J=8.70, 5.95 Hz, 1H), 4.81–4.84 (m, 1H), 6.61 (s, 1H), 7.21 (s, 1H). MS (ESI) m/z 383 (M+H)$^+$.

EXAMPLE 130 isopropyl 6-chloro-5-[((2R,5S)-5-{[(2S)-2-cyanopyrrolidin-1-yl]carbonyl}pyrrolidin-2-yl)methoxy]nicotinate

EXAMPLE 130A 5-hydroxy-nicotinic acid isopropyl ester

The title compound was synthesized by substituting 4-chloro-3-hydroxybenzoic acid in Example 116A with 5-hydroxy-nicotinic acid. MS (DCI) m/z 182(M+H)$^+$.

EXAMPLE 130B 6-chloro-5-hydroxy-nicotinic acid isopropyl ester

The title compound was synthesized by substituting 5-hydroxy-nicotinic acid tert-butyl ester in Example 52B with 5-hydroxy-nicotinic acid isopropyl ester

EXAMPLE 130C isopropyl 6-chloro-5-[((2R,5S)-5-{[(2S)-2-cyanopyrrolidin-1-yl]carbonyl}pyrrolidin-2-yl)methoxy]nicotinate The title compound was synthesized by substituting 3-tert-butyl-4-hydroxy-benzoic acid tert-butyl ester in Example 47F with 6-chloro-5-hydroxy-nicotinic acid isopropyl ester followed by removal of the Boc group described in Example 103B. $^1$H NMR (500 MHz, MeOH-$d_4$) δ ppm 1.39 (d, J=6.10 Hz, 6H), 2.05–2.46 (m, 7H), 2.55–2.65 (m, 1H), 3.63–3.73 (m, 2H), 4.23–4.31 (m, 1H), 4.52–4.61 (m, 2H), 4.73 (dd, J=8.70, 5.95 Hz, 1H), 4.81–4.85 (m, 1H), 5.23–5.32 (m, 1H), 7.99 (d, J=1.83 Hz, 1H), 8.58 (d, J=1.83 Hz, 1H). MS (ESI) m/z 421(M+H)$^+$.

EXAMPLE 131

(2S)-1-[((2S,5R)-5-{[4-chloro-3-(methylsulfonyl)phenoxy]methyl}pyrrolidin-2-yl)carbonyl]pyrrolidine-2-carbonitrile

EXAMPLE 131A

1-Chloro-2-methanesulfonyl-4-methoxy-benzene

The title compound was synthesized by substituting 4-methanesulfonylphenol in Example 93A with 2-methanesulfonyl-4methoxybenzene. MS (DCI) m/z 238 (M+NH$_4$)$^+$. The other chlorinated product, 2-chloro-3-methanesulfonyl-benzene was separated from the title product by reverse-phase HPLC.

EXAMPLE 131B

4-Chloro-3-methanesulfonyl-phenol 1-chloro-2-methanesulfonyl-4-methoxy-benzene obtained above (282 mg, 1.28 mmol) dissolved in 3 mL of dichloromethane was cooled to −78° C., and then BBr$_3$ solution (1M in CH$_2$Cl$_2$, 1.9 mL) was added slowly. The reaction was stirred overnight during which the reaction was gradually warmed to room temperature. The reaction was quenched by careful addition of water, extracted with EtOAc. The combined extracts were dried over Na$_2$SO$_4$ and concentrated in vacuum. The resulting residue was purified by flash chromatography (30–45% EtOAc/Hex) to give the desired phenol. MS (DCI) m/z 224 (M+NH$_4$)$^+$.

EXAMPLE 131 C (2S)-1-[((2S,5R)-5-{[4-chloro-3-(methylsulfonyl)phenoxy]methyl}pyrrolidin-2-yl)carbonyl]pyrrolidine-2-carbonitrile The title compound was synthesized by substituting 3-tert-butyl-4-hydroxy-benzoic acid tert-butyl ester in Example 47F with 4chloro-3-methanesulfonyl-phenol followed by removal of the Boc group described in Example 103B. $^1$H NMR (500 MHz, MeOH-d$_4$) δ ppm 2.02 (dd, J=13.04, 8.75 Hz, 1H), 2.10–2.45 (m, 7H), 2.61 (dd, J=13.35, 8.44 Hz, 1H), 3.31 (overlaps with solvent peak, 3H), 3.63–3.71 (m, 2H), 4.12–4.23 (m, 1H), 4.38–4.50 (m, 2 H), 4.71 (dd, J=9.05, 5.68 Hz, 1H), 4.82–4.85 (m, J=4.30 Hz, 1H), 7.35 (dd, J=8.59, 3.07 Hz, 1H), 7.61 (d, J=8.59 Hz, 1H), 7.74 (d, J=3.07 Hz, 1H). MS (ESI) m/z 412 (M+H)$^+$.

EXAMPLE 132

(2S)-1-[((2S,5R)-5-{[2-chloro-3-(methylsulfonyl)phenoxy]methyl}pyrrolidin-2-yl)carbonyl]pyrrolidine-2-carbonitrile The title compound was synthesized by substituting 3-tert-butyl-4-hydroxy-benzoic acid tert-butyl ester in Example 47F with 2-chloro-3-methanesulfonyl-phenol (from Example 131A) followed by removal of the Boc group described in Example 103B. $^1$H NMR (500 MHz, MeOH-d$_4$) δ ppm 2.05–2.46 (m, 7H), 2.56–2.66 (m, 1H), 3.31 (overlaps with solvent peak, 3 H), 3.64–3.72 (m, 2H), 4.27 (dd, J=8.29, 3.99 Hz, 1H), 4.46–4.57 (m, 2H), 4.72 (dd, J=8.59, 6.14 Hz, 1H), 4.82–4.86 (m, 1H), 7.49–7.54 (m, 1H), 7.57 (t, J=7.98 Hz, 1H), 7.79 (dd, J=7.67, 1.53 Hz, 1H). MS (ESI) m/z 412(M+H)$^+$.

EXAMPLE 133 ethyl 3-[((2R,5S)-5-{[(2S)-2-cyanopyrrolidin-1-yl]carbonyl}pyrrolidin-2-yl)methoxy]-4,5-difluorobenzoate

EXAMPLE 133A 3,4-difluoro-5-hydroxy-benzoic acid ethyl ester

The title compound was synthesized by substituting 1-benzyloxy-4-bromo-2-tert-butyl-benzene in Example 47C with 2,3-difluoro-5-bromophenol in EtOH. MS (DCI) m/z 220 (M+NH$_4$)$^+$.

EXAMPLE 133B ethyl 3-[((2R,5S)-5-{[(2S)-2-cyanopyrrolidin-1-yl]carbonyl}pyrrolidin-2-yl)methoxy]-4,5-difluorobenzoate The title compound was synthesized by substituting 3-tert-butyl-4-hydroxy-benzoic acid tert-butyl ester in Example 47F with 3,4difluoro-5-hydroxylbenzoic acid ethyl ester followed by removal of the Boc group described in Example 103B. $^1$H NMR (500 MHz, MeOH-d$_4$) δ ppm 1.39 (t, J=7.21 Hz, 3H), 1.97–2.09 (m, J=13.20, 8.59 Hz, 1H), 2.10–2.45 (m, 6H), 2.60 (ddd, J=16.65, 13.27, 8.44 Hz, 1H), 3.62–3.71 (m, 2H), 4.17–4.27 (m, 1H), 4.38 (q, J=7.06 Hz, 2 H), 4.48–4.57 (m, 2H), 4.71 (dd, J=8.90, 5.83 Hz, 1H), 4.82–4.86 (m, 1H), 7.54–7.62 (m, 1 H), 7.62–7.68 (m, J=7.06, 1.84 Hz, 1H). MS (ESI) m/z 408 (M+H)$^+$.

EXAMPLE 134

3-[((2R,5S)-5-{[(2S)-2-cyanopyrrolidin-1-yl]carbonyl}pyrrolidin-2-yl)methoxy]-4,5-difluorobenzoic acid

EXAMPLE 134A 3,4-Difluoro-5-hydroxy-benzoic acid tert-butyl ester

The title compound was synthesized by substituting 4-benzyloxy-3-tert-butyl-benzoic acid methyl ester in Example 47D with 3,4difluoro-5-hydroxy-benzoic acid ethyl ester (form Example 133A). MS (DCI) m/z 231(M+H)$^+$, 248 (M+NH$_4$)$^+$.

EXAMPLE 134B 2R-(5-tert-butoxycarbonyl-2,3-difluoro-phenoxymethyl)-5S-(2S-cyano-pyrrolidine-1-carbonyl)-pyrrolidine-1-carboxylic acid tert-butyl ester The title compound was synthesized by substituting 3-tert-butyl-4-hydroxy-benzoic acid tert-butyl ester in Example 47F with 4,5-difluoro-3-hydroxylbenzoic acid tert-butyl ester.

EXAMPLE 134C

3-[((2R,5S)-5-{[(2S)-2-cyanopyrrolidin-1-yl]carbonyl}pyrrolidin-2-yl)methoxy]-4,5-difluorobenzoic acid Both Boc and tert-butyl groups were removed using procedure described in Example 103B. $^1$H NMR (400 MHz, MeOH-$d_4$) δ ppm 2.03 (ddd, J=17.49, 13.20, 8.59 Hz, 1H), 2.11–2.44 (m, 6H), 2.60 (ddd, J=16.80, 13.27, 8.59 Hz, 1H), 3.62–3.72 (m, 2H), 4.17–4.26 (m, 1H), 4.48–4.56 (m, 2H), 4.71 (dd, J=8.90, 5.83 Hz, 1H), 4.83–4.87 (m, 1H), 7.55–7.62 (m, 1H), 7.63–7.68 (m, J=5.37, 1.69 Hz, 1H). MS (ESI) m/z 380 (M+H)$^+$.

EXAMPLE 135 tert-butyl 3-[((2R,5S)-5-{[(2S)-2-cyanopyrrolidin-1-yl]carbonyl}pyrrolidin-2-yl)methoxy]-4,5-difluorobenzoate The title compound was obtained when only the Boc group in Example 134B was removed using the procedure described in Example 103B. $^1$H NMR (400 MHz, MeOH-$d_4$) δ ppm 1.59 (s, 9H), 2.03 (ddd, J=17.18, 13.04, 8.44 Hz, 1H), 2.11–2.44 (m, 6H), 2.60 (ddd, J=16.80, 13.27, 8.59 Hz, 1H), 3.62–3.72 (m, 2H), 4.16–4.27 (m, 1H), 4.48–4.56 (m, 2H), 4.71 (dd, J=8.90, 5.83 Hz, 1H), 4.83–4.86 (m, 1H), 7.51 (dt, J=10.28, 6.90, 1.84 Hz, 1H), 7.55–7.60 (m, 1H). MS (ESI) m/z 436 (M+H)$^+$.

The following additional compounds, representative of formula (I), may be prepared by one skilled in the art using known synthetic methodology or by using synthetic methodology described in the Schemes and Examples contained herein;

4-[((2R,5S)-5-{[(2S)-2-cyanopyrrolidin-1-yl]carbonyl}pyrrolidin-2-yl)methoxy]-3-methylbenzenesulfonamide;

3-bromo-4-[((2R,5S)-5-{[(2S)-2-cyanopyrrolidin-1-yl]carbonyl}pyrrolidin-2-yl)methoxy]benzenesulfonamide;

3-cyano-4-[((2R,5S)-5-{[(2S)-2-cyanopyrrolidin-1-yl]carbonyl}pyrrolidin-2-yl)methoxy]benzenesulfonamide;

4-[((2R,5S)-5-{[(2S)-2-cyanopyrrolidin-1-yl]carbonyl}pyrrolidin-2-yl)methoxy]-N,3-dimethylbenzenesulfonamide;

3-bromo-4-[((2R,5S)-5-{[(2S)-2-cyanopyrrolidin-1-yl]carbonyl}pyrrolidin-2-yl)methoxy]-N-methylbenzenesulfonamide;

3-cyano-4-[((2R,5S)-5-{[(2S)-2-cyanopyrrolidin-1-yl]carbonyl}pyrrolidin-2-yl)methoxy]-N-methylbenzenesulfonamide;

3-[((2R,5S)-5-{[(2S)-2-cyanopyrrolidin-1-yl]carbonyl}pyrrolidin-2-yl)methoxy]-4-methyl-N-phenylbenzenesulfonamide;

4-chloro-3-[((2R,5S)-5-{[(2S)-2-cyanopyrrolidin-1-yl]carbonyl}pyrrolidin-2-yl)methoxy]-N-phenylbenzenesulfonamide;

3-[((2R,5S)-5-{[(2S)-2-cyanopyrrolidin-1-yl]carbonyl}pyrrolidin-2-yl)methoxy]-4-methoxy-N-phenylbenzenesulfonamide;

N-({3-[((2R,5S)-5-{[(2S)-2-cyanopyrrolidin-1-yl]carbonyl}pyrrolidin-2-yl)methoxy]-4-methylphenyl}sulfonyl)acetamide;

N-({4-chloro-3-[((2R,5S)-5-{[(2S)-2-cyanopyrrolidin-1-yl]carbonyl}pyrrolidin-2-yl)methoxy]phenyl}sulfonyl)acetamide;

N-({3-[((2R,5S)-5-{[(2S)-2-cyanopyrrolidin-1-yl]carbonyl}pyrrolidin-2-yl)methoxy]-4-methoxyphenyl}sulfonyl)acetamide;

3-[((2R,5S)-5-{[(2S)-2-cyanopyrrolidin-1-yl]carbonyl}pyrrolidin-2-yl)methoxy]-4-methylbenzamide;

4-bromo-3-[((2R,5S)-5-{[(2S)-2-cyanopyrrolidin-1-yl]carbonyl}pyrrolidin-2-yl)methoxy]benzamide;

4-cyano-3-[((2R,5S)-5-{[(2S)-2-cyanopyrrolidin-1-yl]carbonyl}pyrrolidin-2-yl)methoxy]benzamide;

3-[((2R,5S)-5-{[(2S)-2-cyanopyrrolidin-1-yl]carbonyl}pyrrolidin-2-yl)methoxy]-N,4-dimethylbenzamide;

4-bromo-3-[((2R,5S)-5-{[(2S)-2-cyanopyrrolidin-1-yl]carbonyl}pyrrolidin-2-yl)methoxy]-N-methylbenzamide;

4-cyano-3-[((2R,5S)-5-{[(2S)-2-cyanopyrrolidin-1-yl]carbonyl}pyrrolidin-2-yl)methoxy]-N-methylbenzamide;

3-[((2R,5S)-5-{[(2S)-2-cyanopyrrolidin-1-yl]carbonyl}pyrrolidin-2-yl)methoxy]-4-methyl-N-phenylbenzamide;

4-bromo-3-[((2R,5S)-5-{[(2S)-2-cyanopyrrolidin-1-yl]carbonyl}pyrrolidin-2-yl)methoxy]-N-phenylbenzamide;

4-cyano-3-[((2R,5S)-5-{[(2S)-2-cyanopyrrolidin-1-yl]carbonyl}pyrrolidin-2-yl)methoxy]-N-phenylbenzamide;

N-{4-chloro-3-[((2R,5S)-5-{[(2S)-2-cyanopyrrolidin-1-yl]carbonyl}pyrrolidin-2-yl)methoxy]phenyl}acetamide;

N-{4-chloro-3-[((2R,5S)-5-{[(2S)-2-cyanopyrrolidin-1-yl]carbonyl}pyrrolidin-2-yl)methoxy]phenyl}-2-furamide;

3-[({4-chloro-3-[((2R,5S)-5-{[(2S)-2-cyanopyrrolidin-1-yl]carbonyl}carbonyl}pyrrolidin-2-yl)methoxy]phenyl}amino)carbonyl]benzoic acid;

6-[({4-chloro-3-[((2R,5S)-5-{[(2S)-2-cyanopyrrolidin-1-yl]carbonyl}pyrrolidin-2-yl)methoxy]phenyl}amino)carbonyl]pyridine-2-carboxylic acid;

N-{4-chloro-3-[((2R,5S)-5-{[(2S)-2-cyanopyrrolidin-1-yl]carbonyl}pyrrolidin-2-yl)methoxy]phenyl}benzenesulfonamide;

2-{4-chloro-3-[((2R,5S)-5-{[(2S)-2-cyanopyrrolidin-1-yl]carbonyl}pyrrolidin-2-yl)methoxy]phenoxy}-2-methylpropanoic acid;

({4-chloro-3-[((2R,5S)-5-{[(2S)-2-cyanopyrrolidin-1-yl]carbonyl}pyrrolidin-2-yl)methoxy]phenyl}amino)(oxo)acetic acid;

3-[((2R,5S)-5-{[(2S)-2-cyanopyrrolidin-1-yl]carbonyl}pyrrolidin-2-yl)methoxy]-4-(trifluoromethyl)benzoic acid;

3-[((2R,5S)-5-{[(2S)-2-cyanopyrrolidin-1-yl]carbonyl}pyrrolidin-2-yl)methoxy]-4-methoxybenzoic acid;

4-chloro-3-[((2R,5S)-5-{[(2S)-2-cyanopyrrolidin-1-yl]carbonyl}pyrrolidin-2-yl)methoxy]-N,N-dimethylbenzamide;

4-chloro-3-[((2R,5S)-5-{[(2S)-2-cyanopyrrolidin-1-yl]carbonyl}pyrrolidin-2-yl)methoxy]-N-pyridin-4-ylbenzamide;

3-chloro-4-[((2R,5S)-5-{[(2S)-2-cyanopyrrolidin-1-yl]carbonyl}pyrrolidin-2-yl)methoxy]benzenesulfonamide;

4-[((2R,5S)-5-{[(2S)-2-cyanopyrrolidin-1-yl]carbonyl}pyrrolidin-2-yl)methoxy]-3-methoxybenzenesulfonamide;

4-[((2R,5S)-5-{[(2S)-2-cyanopyrrolidin-1-yl]carbonyl}pyrrolidin-2-yl)methoxy]-3-isopropylbenzenesulfonamide;

3-chloro-4-[((2R,5S)-5-{[(2S)-2-cyanopyrrolidin-1-yl]carbonyl}pyrrolidin-2-yl)methoxy]-N-methylbenzenesulfonamide;

4-[((2R,5S)-5-{[(2S)-2-cyanopyrrolidin-1-yl]carbonyl}pyrrolidin-2-yl)methoxy]-3-methoxy-N-methylbenzenesulfonamide;

4-[((2R,5S)-5-{[(2S)-2-cyanopyrrolidin-1-yl]carbonyl}pyrrolidin-2-yl)methoxy]-3-isopropyl-N-methylbenzenesulfonamide;

3-[((2R,5S)-5-{[(2S)-2-cyanopyrrolidin-1-yl]carbonyl}pyrrolidin-2-yl)methoxy]-4-isopropyl-N-phenylbenzenesulfonamide;

4-bromo-3-[((2R,5S)-5-{[(2S)-2-cyanopyrrolidin-1-yl]carbonyl}pyrrolidin-2-yl)methoxy]-N-phenylbenzenesulfonamide;

4-cyano-3-[((2R,5S)-5-{[(2S)-2-cyanopyrrolidin-1-yl]carbonyl}pyrrolidin-2-yl)methoxy]-N-phenylbenzenesulfonamide;

N-({3-[((2R,5S)-5-{[(2S)-2-cyanopyrrolidin-1-yl]carbonyl}pyrrolidin-2-yl)methoxy]-4-isopropylphenyl}sulfonyl)acetamide;

N-({4-bromo-3-[((2R,5S)-5-{[(2S)-2-cyanopyrrolidin-1-yl]carbonyl}pyrrolidin-2-yl)methoxy]phenyl}sulfonyl)acetamide;

N-({4-cyano-3-[((2R,5S)-5-{[(2S)-2-cyanopyrrolidin-1-yl]carbonyl}pyrrolidin-2-yl)methoxy]phenyl}sulfonyl)acetamide;

4-chloro-3-[((2R,5S)-5-{[(2S)-2-cyanopyrrolidin-1-yl]carbonyl}pyrrolidin-2-yl)methoxy]benzamide;

3-[((2R,5S)-5-{[(2S)-2-cyanopyrrolidin-1-yl]carbonyl}pyrrolidin-2-yl)methoxy]-4-methoxybenzamide;

3-[((2R,5S)-5-{[(2S)-2-cyanopyrrolidin-1-yl]carbonyl}pyrrolidin-2-yl)methoxy]-4-isopropylbenzamide;

4-chloro-3-[((2R,5S)-5-{[(2S)-2-cyanopyrrolidin-1-yl]carbonyl}pyrrolidin-2-yl)methoxy]-N-methylbenzamide;

3-[((2R,5S)-5-{[(2S)-2-cyanopyrrolidin-1-yl]carbonyl}pyrrolidin-2-yl)methoxy]-4-methoxy-N-methylbenzamide;

3-[((2R,5S)-5-{[(2S)-2-cyanopyrrolidin-1-yl]carbonyl}pyrrolidin-2-yl)methoxy]-4-isopropyl-N-methylbenzamide;

4-chloro-3-[((2R,5S)-5-{[(2S)-2-cyanopyrrolidin-1-yl]carbonyl}pyrrolidin-2-yl)methoxy]-N-phenylbenzamide;

3-[((2R,5S)-5-{[(2S)-2-cyanopyrrolidin-1-yl]carbonyl}pyrrolidin-2-yl)methoxy]-4-methoxy-N-phenylbenzamide;

3-[((2R,5S)-5-{[(2S)-2-cyanopyrrolidin-1-yl]carbonyl}pyrrolidin-2-yl)methoxy]-4-isopropyl-N-phenylbenzamide;

N-{4-chloro-3-[((2R,5S)-5-{[(2S)-2-cyanopyrrolidin-1-yl]carbonyl}pyrrolidin-2-yl)methoxy]phenyl}-2-methoxyacetamide;

N-{4-chloro-3-[((2R,5S)-5-{[(2S)-2-cyanopyrrolidin-1-yl]carbonyl}pyrrolidin-2-yl)methoxy]phenyl}benzamide;

N-{4-chloro-3-[((2R,5S)-5-{[(2S)-2-cyanopyrrolidin-1-yl]carbonyl}pyrrolidin-2-yl)methoxy]phenyl}nicotinamide;

N-{4-chloro-3-[((2R,5S)-5-{[(2S)-2-cyanopyrrolidin-1-yl]carbonyl}pyrrolidin-2-yl)methoxy]phenyl}methanesulfonamide;

(2S)-1-[((2S,5R)-5-{[5-(benzylamino)-2-chlorophenoxy]methyl}pyrrolidin-2-yl)carbonyl]pyrrolidine-2-carbonitrile;

{4-chloro-3-[((2R,5S)-5-{[(2S)-2-cyanopyrrolidin-1-yl]carbonyl}pyrrolidin-2-yl)methoxy]phenoxy}acetic acid;

4-({4-chloro-3-[((2R,5S)-5-{[(2S)-2-cyanopyrrolidin-1-yl]carbonyl}pyrrolidin-2-yl)methoxy]phenyl}amino)-4-oxobutanoic acid;

3-[((2R,5S)-5-{[(2S)-2-cyanopyrrolidin-1-yl]carbonyl}pyrrolidin-2-yl)methoxy]-4-(1H-pyrazol-3-yl)benzoic acid;

3-[((2R,5S)-5-{[(2S)-2-cyanopyrrolidin-1-yl]carbonyl}pyrrolidin-2-yl)methoxy]-4-isopropoxybenzoic acid; and 4-chloro-3-[((2R,5S)-5-{[(2S)-2-cyanopyrrolidin-1-yl]carbonyl}pyrrolidin-2-yl)methoxy]-N-phenylbenzamide.

What is claimed is:

1. A compound of Formula (I)

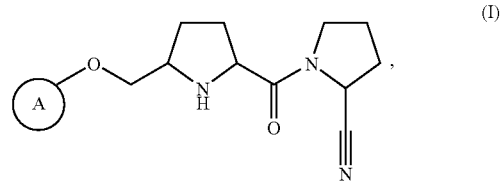

or a therapeutically acceptable salt thereof, wherein
A is selected from the group consisting of

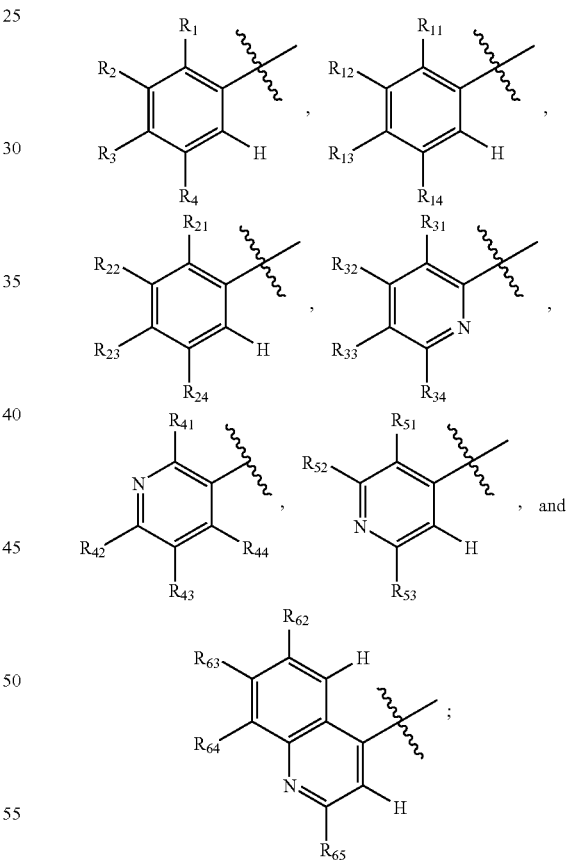

or therapeutically suitable salt, ester or prodrug, thereof, wherein $R_1$ is selected from the group consisting of halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, carboxyalkoxy, alkylcarbonyl, alkylsulfonyl, aryl, heteroaryl, heterocycle, cycloalkyl, arylalkyl, heteroarylalkyl, heterocyclealkyl, hydroxyalkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_2$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

or $R_1$ and $R_2$, together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, naphthalene, furan, imidazole, isothiazole, isoxazole, 1,3-dioxolane, 1,2,3-oxadiazole, 1,2,5-oxadiazole, oxazole, pyrazine, pyrazole, pyridazine, pyrimidine, pyrrole, thiazole, thiophene, triazine, 1,2,3-triazole or unsubstituted pyridine;

$R_3$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_4$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, alkoxy cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

with the proviso that if $R_1$ and $R_2$ and the carbon atoms to which they are attached form a benzene ring, then $R_4$ is not carboxylic acid;

$R_a$ and $R_b$ are independently selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl;

$R_{11}$ is selected from the group consisting of halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{12}$ and $R_{13}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole;

$R_{14}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{21}$ is selected from the group consisting of halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{22}$ is selected from the group consisting of hydrogen, halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{23}$ and $R_{24}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, naphthalene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole;

$R_{31}$ is selected from the group consisting of halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{32}$ is selected from the group consisting of hydrogen, halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{33}$ is selected from the group consisting of hydrogen, halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{34}$ is selected from the group consisting of hydrogen, halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{41}$ is selected from the group consisting of hydrogen, halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{42}$ is selected from the group consisting of hydrogen, halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{43}$ is selected from the group consisting of hydrogen, halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{44}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{51}$ is selected from the group consisting of halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{52}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

or $R_{51}$ and $R_{52}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole;

$R_{53}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; and $R_{62}$, $R_{63}$, $R_{64}$ and $R_{65}$ are each independently selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl.

2. The compound according to claim 1, wherein

A is

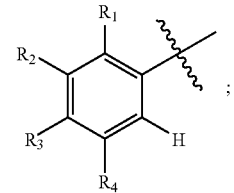
;

$R_1$ is selected from the group consisting of halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, carboxyalkoxy, alkylcarbonyl, alkylsulfonyl, aryl, heteroaryl, heterocycle, cycloalkyl, arylalkyl, heteroarylalkyl, heterocyclealkyl, hydroxyalkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_2$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_3$ is selected from the group consisting of hydrogen, halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_4$ is selected from the group consisting of hydrogen, halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, alkoxycyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; and $R_a$ and $R_b$ are independently selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl.

3. The compound according to claim 1, wherein

A is

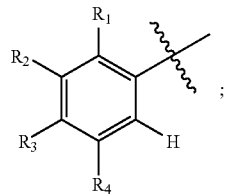

$R_1$ is selected from the group consisting of halo, haloalkyl, haloalkoxy, $R_aR_bN-$, $R_aR_b$Ncarbonyl, alkoxy, alkoxycarbonyl, cyano, hydroxyalkyl, alkyl, alkenyl, carboxy, carboxyalkyl, carboxyalkoxy, alkylcarbonyl, alkylsulfonyl, aryl, heteroaryl, heterocycle, hydroxyalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_2$ is selected from the group consisting of hydrogen, halo, haloalkyl, haloalkoxy, $R_aR_bN-$, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_3$ is selected from the group consisting of hydrogen, halo, haloalkyl, haloalkoxy, $R_aR_bN-$, $R_aR_b$Ncarbonyl, $R_aR_b$Ncarbonylalkyl, $R_aR_b$Nsulfonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_4$ is selected from the group consisting of hydrogen, halo, haloalkyl, haloalkoxy, $R_aR_bN-$, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; and $R_a$ and $R_b$ are independently selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl.

4. The compound according to claim 1, wherein

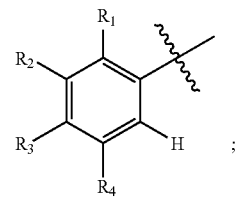

$R_1$ is selected from the group consisting of halo, alkoxy, cyano, alkyl, carboxy, carboxyalkyl, carboxyalkoxy, alkylsulfonyl, heteroaryl and hydroxyalkyl, wherein the heteroaryl is pyrazolyl;

R$_2$ is selected from the group consisting of hydrogen, halo and alkylsulfonyl;

R$_3$ is selected from the group consisting of hydrogen, halo, haloalkyl, R$_a$R$_b$N—, R$_a$R$_b$Ncarbonyl, alkoxy, alkoxycarbonyl, cyano, carboxy, carboxyalkoxy, alkylsulfonyl, heteroaryl and heterocycle, wherein the heteroaryl is tetrazolyl;

R$_4$ is selected from the group consisting of hydrogen, R$_a$R$_b$N—, alkoxycarbonyl, cyano, carboxy, alkylsulfonylNH and nitro; and R$_a$ and R$_b$ are independently selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl.

5. The compound according to claim 1, wherein

A is

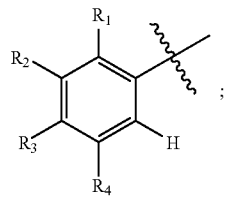
;

R$_1$ and R$_2$, together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, naphthalene, furan, imidazole, isothiazole, isoxazole, 1,3-dioxolane, 1,2,3-oxadiazole, 1,2,5-oxadiazole, oxazole, pyrazine, pyrazole, pyridazine, pyrimidine, pyrrole, thiazole, thiophene, triazine, 1,2,3-triazole or unsubstituted pyridine;

R$_3$ is selected from the group consisting of hydrogen, halo, haloalkyl, haloalkoxy, haloalkylthio, R$_a$R$_b$N—, R$_a$R$_b$Ncarbonyl, R$_a$R$_b$Ncarbonylalkyl, R$_a$R$_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

R$_4$ is selected from the group consisting of hydrogen, halo, haloalkyl, haloalkoxy, haloalkylthio, R$_a$R$_b$N—, R$_a$R$_b$Ncarbonyl, R$_a$R$_b$Ncarbonylalkyl, R$_a$R$_b$Nsulfonyl, alkoxy, alkoxyalkoxy, alkoxyalkyl, alkoxycarbonyl, alkoxy cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

with the proviso that if R$_1$ and R$_2$ and the carbon atoms to which they are attached form a benzene ring, then R$_4$ is not carboxylic acid; and R$_a$ and R$_b$ are independently selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl.

6. The compound according to claim 1, wherein

A is

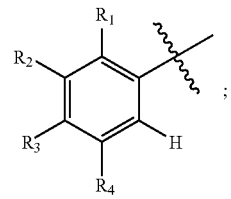
;

R$_1$ and R$_2$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, naphthalene, furan, imidazole, isothiazole, isoxazole, 1,3-dioxolane, 1,2,3-oxadiazole, 1,2,5-oxadiazole, oxazole, pyrazine, pyrazole, pyridazine, pyrimidine, pyrrole, thiazole, thiophene, triazine, 1,2,3-triazole or unsubstituted pyridine;

R$_3$ is selected from the group consisting of hydrogen, halo, haloalkyl, haloalkoxy, R$_a$R$_b$N—, R$_a$R$_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

R$_4$ is selected from the group consisting of hydrogen, halo, haloalkyl, haloalkoxy, R$_a$R$_b$N—, R$_a$R$_b$Ncarbonyl, alkoxy, alkoxycarbonyl, alkoxy cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

with the proviso that if R$_1$ and R$_2$ and the carbon atoms to which they are attached form a benzene ring, then R$_4$ is not carboxylic acid; and $R_a$ and $R_b$ are independently selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl.

7. The compound according to claim 1, wherein

A is

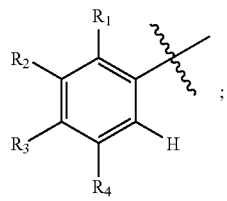

$R_1$ and $R_2$, together with the carbon atoms to which they are attached, form a substituted or unsubstituted heterocycle or a substituted or unsubstituted aryl, heteroaryl or cycloalkyl selected from the group consisting of benzene, thiophene or unsubstituted pyridine;

$R_3$ is selected from the group consisting of hydrogen, halo, haloalkyl, $R_aR_bN$—, $R_aR_b$Ncarbonyl, alkoxy, alkoxycarbonyl, cyano, carboxy, carboxyalkoxy, alkylsulfonyl, heteroaryl, heterocycle, wherein the heteroaryl is tetrazolyl;

$R_4$ is selected from the group consisting of hydrogen, $R_aR_bN$—, alkoxycarbonyl, alkoxy cyano, alkylsulfonylNH and nitro; and $R_a$ and $R_b$ are independently selected from the group consisting of hydrogen, alkyl, aryl, alkenylcarbonyl, alkoxycarbonyl, alkoxyalkylcarbonyl, alkoxyalkoxycarbonyl, alkylcarbonyl, alkylsulfonyl, arylcarbonyl, arylalkylsulfonyl, arylsulfonyl, arylNHC(O), alkylsulfonyl, cycloalkylcarbonyl, heteroaryl, and heteroarylcarbonyl.

8. The compound according to claim 1, wherein

A is

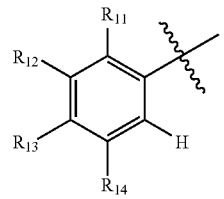

$R_{11}$ is selected from the group consisting of halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{12}$ and $R_{13}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole; and $R_{14}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl.

9. The compound according to claim 1, wherein

A is

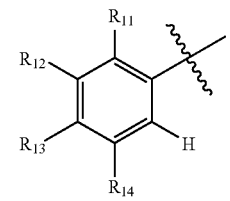

$R_{11}$ is selected from the group consisting of halo, haloalkyl, haloalkoxy, $R_aR_bN$—, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, nitro, wherein the heteroaryls are selected from the group consisting of furanyl, imidazolyl, isothiazolyl, isoxazolyl, 1,2,3-oxadiazoyl, 1,2,5oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{12}$ and $R_{13}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole;

$R_{14}$ is selected from the group consisting of hydrogen, halo, haloalkyl, haloalkoxy, $R_aR_bN$—, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl.

10. The compound according to claim 1, wherein

A is

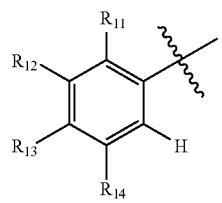

$R_{11}$ is selected from the group consisting of halo, alkoxy, cyano and carboxy;

$R_{12}$ and $R_{13}$ together with the carbon atoms to which they are attached, form a substituted or unsubstituted benzene; and $R_{14}$ is hydrogen.

11. The compound according to claim 1, wherein

A is

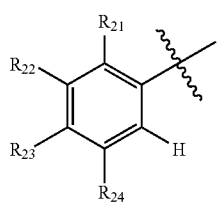

$R_{21}$ is selected from the group consisting of halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{22}$ is selected from the group consisting of hydrogen, halo, haloalkyl, haloalkoxy, haloalkylthio, $R_aR_bN-$, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{23}$ and $R_{24}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, naphthalene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazolyl.

12. The compound according to claim 1, wherein

A is

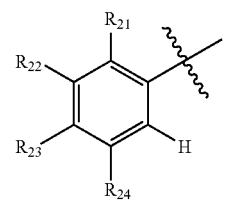

$R_{21}$ is selected from the group consisting of halo, haloalkyl, haloalkoxy, $R_aR_bN-$, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{22}$ is selected from the group consisting of hydrogen, halo, haloalkyl, haloalkoxy, $R_aR_bN-$, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{23}$ and $R_{24}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, naphthalene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazolyl.

13. The compound according to claim 1, wherein

A is

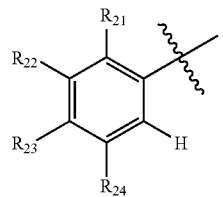

$R_{21}$ is selected from the group consisting of halo and carboxy;

$R_{22}$ is selected from the group consisting of hydrogen and halo; and $R_{23}$ and $R_{24}$ together with the carbon atoms to which they are attached, form 1,3-dioxolane.

14. The compound according to claim 1, wherein

A is

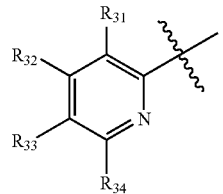

$R_{31}$ is selected from the group consisting of halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{32}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{33}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{34}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; and wherein the nitrogen of the pyridine group of A may be optionally substituted with an oxide.

15. The compound according to claim 1, wherein

A is

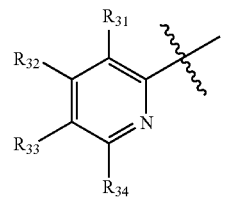

$R_{31}$ is selected from the group consisting of halo, haloalkyl, haloalkoxy, $R_aR_bN$—, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{32}$ is selected from the group consisting of hydrogen, halo, haloalkyl, haloalkoxy, $R_aR_bN$—, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{33}$ is selected from the group consisting of hydrogen, halo, haloalkyl, haloalkoxy, $R_aR_bN-$, $R_aR_bN$carbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{34}$ is selected from the group consisting of hydrogen, halo, haloalkyl, haloalkoxy, $R_aR_bN-$, $R_aR_bN$carbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; and wherein the nitrogen of the pyridine group of A may be optionally substituted with an oxide.

16. The compound according to claim 1, wherein

A is

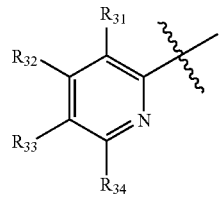

$R_{31}$ is halo;
$R_{32}$ is hydrogen;
$R_{33}$ is hydrogen,;
$R_{34}$ is hydrogen; and wherein
the nitrogen of the pyridine group of A may be optionally substituted with an oxide.

17. The compound according to claim 1, wherein

A is

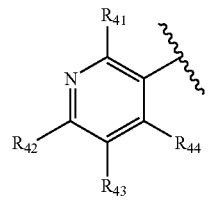

$R_{41}$ is selected from the group consisting of hydrogen, halo, haloalkyl, haloalkoxy, haloalkylthio, $R_aR_bN-$, $R_aR_bN$carbonyl, $R_aR_bN$carbonylalkyl, $R_aR_bN$sulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{42}$ is selected from the group consisting of hydrogen, halo, haloalkyl, haloalkoxy, haloalkylthio, $R_aR_bN-$, $R_aR_bN$carbonyl, $R_aR_bN$carbonylalkyl, $R_aR_bN$sulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{43}$ is selected from the group consisting of hydrogen, halo, haloalkyl, haloalkoxy, haloalkylthio, $R_aR_bN-$, $R_aR_bN$carbonyl, $R_aR_bN$carbonylalkyl, $R_aR_bN$sulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

$R_{44}$ is selected from the group consisting of hydrogen, halo, haloalkyl, haloalkoxy, haloalkylthio, $R_aR_bN-$, $R_aR_bN$carbonyl, $R_aR_bN$carbonylalkyl, $R_aR_bN$sulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; and wherein the nitrogen of the pyridine group of A may be optionally substituted with an oxide;

provided that exactly one of $R_{41}$ or $R_{44}$ is hydrogen.

18. The compound according to claim 1, wherein

A is

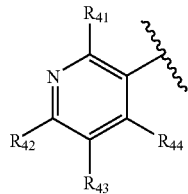

R$_{41}$ is selected from the group consisting of hydrogen, halo, haloalkyl, haloalkoxy, R$_a$R$_b$N—, R$_a$R$_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

R$_{42}$ is selected from the group consisting of hydrogen, halo, haloalkyl, haloalkoxy, R$_a$R$_b$N—, R$_a$R$_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazol:A, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

R$_{43}$ is selected from the group consisting of hydrogen, halo, haloalkyl, haloalkoxy, R$_a$R$_b$N—, R$_a$R$_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

R$_{44}$ is selected from the group consisting of hydrogen, halo, haloalkyl, haloalkoxy, R$_a$R$_b$N—, R$_a$R$_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; and wherein the nitrogen of the pyridine group of A may be optionally substituted with an oxide;

provided that exactly one of R$_{41}$ or R$_{44}$ is hydrogen.

19. The compound according to claim 1, wherein

A is

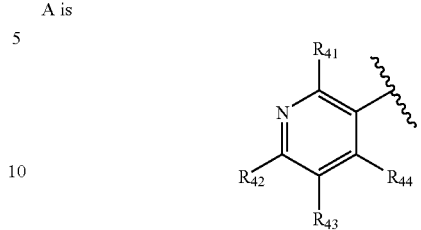

R$_{41}$ is selected from the group consisting of hydrogen, halo and carboxy;

R$_{42}$ is hydrogen;

R$_{43}$ is selected from the group consisting of hydrogen, halo, alkoxycarbonyl and carboxy;

R$_{44}$ is hydrogen; and wherein the nitrogen of the pyridine group of A may be optionally substituted with an oxide;

provided that exactly one of R$_{41}$ or R$_{44}$ is hydrogen.

20. The compound according to claim 1, wherein

A is

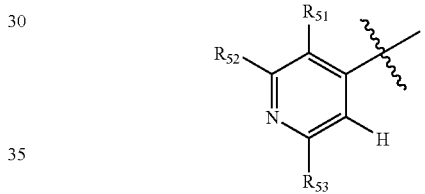

R$_{51}$ is selected from the group consisting of halo, haloalkyl, haloalkoxy, haloalkylthio, R$_a$R$_b$N—, R$_a$R$_b$Ncarbonyl, R$_a$R$_b$Ncarbonylalkyl, R$_a$R$_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

R$_{52}$ is selected from the group consisting of hydrogen, halo, haloalkyl, haloalkoxy, haloalkylthio, R$_a$R$_b$N—, R$_a$R$_b$Ncarbonyl, R$_a$R$_b$Ncarbonylalkyl, R$_a$R$_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

or $R_{51}$ and $R_{52}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole;

$R_{53}$ is selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; and wherein the nitrogen of the pyridine group of A may be optionally substituted with an oxide.

21. The compound according to claim 1, wherein

A is

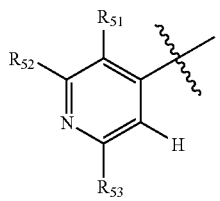

$R_{51}$ is selected from the group consisting of halo, haloalkyl, haloalkoxy, $R_aR_bN$—, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl;

$R_{52}$ is selected from the group consisting of hydrogen, halo, haloalkyl, haloalkoxy, $R_aR_bN$—, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl,heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl;

or $R_{51}$ and $R_{52}$ together with the carbon atoms to which they are attached, form a substituted or unsubstituted heterocycle or a substituted or unsubstituted aryl, heteroaryl or cycloalkyl selected from the group consisting of benzene, cyclopentane, cyclohexane, cyclopentene, cyclohexene, furan, imidazole, isothiazole, isoxazole, 1,3-dioxolane, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole;

$R_{53}$ is selected from the group consisting of hydrogen, halo, haloalkyl, haloalkoxy, $R_aR_bN$—, $R_aR_b$Ncarbonyl, alkoxy, alkoxycarbonyl, cyano, hydroxy, hydroxyalkyl, alkyl, alkenyl, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, nitro, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyridazinyl, pyridinyl, pyrimidinyl, pyrrolyl, tetrazolyl, thiazolyl, thiophenyl, triazinyl and 1,2,3-triazolyl; and wherein the nitrogen of the pyridine group of A may be optionally substituted with an oxide.

22. The compound according to claim 1, wherein

A is

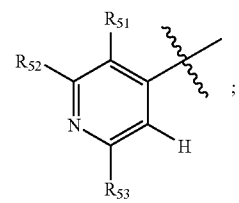

$R_{51}$ and $R_{52}$ together with the carbon atoms to which they are attached, form a benzene;

$R_{53}$ is hydrogen.

23. The compound according to claim 1, wherein

A is

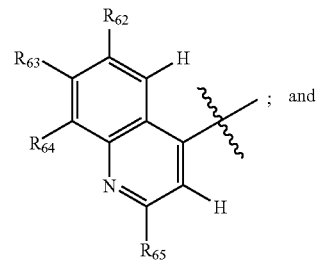

$R_{62}$, $R_{63}$, $R_{64}$ and $R_{65}$ are each independently selected from the group consisting of hydrogen, halo, haloalkyl, haloalkoxy, haloalkylthio, $R_aR_bN$—, $R_aR_b$Ncarbonyl, $R_aR_b$Ncarbonylalkyl, $R_aR_b$Nsulfonyl, alkoxy, alkoxyalkoxy, alkoxyalkyl, alkoxycarbonyl, cyano, cyanoalkyl, hydroxy, hydroxyalkyl, alkyl, alkenyl, alkynyl, alkylthio, carboxy, carboxyalkyl, carboxyalkoxy, alkylcarbonyl, alkylsulfonyl, aryl, heteroaryl, heterocycle, cycloalkyl, arylalkyl, heteroarylalkyl, heterocyclealkyl, cycloalkylalkyl, formyl, formylalkyl, nitro, mercapto and mercaptoalkyl, wherein the heteroaryls are selected from the group consisting of furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl.

24. The compound according to claim 1, wherein

A is

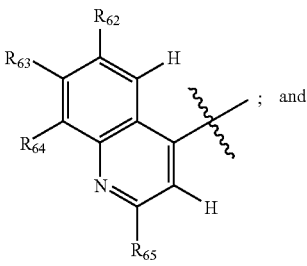 ; and $R_{62}$, $R_{63}$, $R_{64}$ and $R_{65}$ are hydrogen.

25. The compound according to claim 1, that is selected from the group consisting of (2S)-1-{(5R)-5-((2-chlorophenoxy)methyl)-L-prolyl}pyrrolidine-2-carbonitrile;
(2S)-1-{(5R)-5-(naphthalen-1-yloxymethyl)-L-prolyl}-pyrrolidine-2-carbonitrile;
(2S)-1-{(5R)-5-((4-cyano-2-methoxyphenoxy)-methyl)-L-prolyl}-pyrrolidine-2-carbonitrile;
(2S)-1-{(5R)-5-((2-cyano-4-trifluoromethylphenoxy)-methyl)-L-prolyl}-pyrrolidine-2-carbonitrile;
(2S)-1-{(5R)-5-((2-chloro-4-cyanophenoxy)-methyl)-L-prolyl}-pyrrolidine-2-carbonitrile;
(2S)-1-{(5R)-5-((2-chloropyridyl-3-oxy)-methyl)-L-prolyl}-pyrrolidine-2-carbonitrile;
(2S)-1-{(5R)-5-((4-carboxy-2-methoxyphenoxy)-methyl)-L-prolyl}-pyrrolidine-2-carbonitrile;
(2S)-1-{(5R)-5-((4-carboxy-2-tert-butylphenoxy)-methyl)-L-prolyl}-pyrrolidine-2-carbonitrile;
(2S)-1-{(5R)-5-((4-carboxy-2-chlorophenoxy)-methyl)-L-prolyl}-pyrrolidine-2-carbonitrile;
(2S)-1-{(5R)-5-((4-carboxy-2-iso-propylphenoxy)-methyl)-L-prolyl}-pyrrolidine-2-carbonitrile;
(2S)-1-{(5R)-5-([4-(tetrazol-5-yl)-2-chlorophenoxy]-methyl) L-prolyl}-pyrrolidin-2-carbonitrile;
(2S)-1-{(5R)-5-((5-carboxy-2-chlorophenoxy)-methyl)-L-prolyl}-pyrrolidine-2-carbonitrile;
(2S)-1-{(5R)-5-((5-carboxy-2-chloropyridyl-3-oxy)-methyl)-L-prolyl}-pyrrolidine-2-carbonitrile;
(2S)-1-{(5R)-5-(5-carboxynaphthalen-1-yloxymethyl)-L-prolyl}-pyrrolidine-2-carbonitrile;
(2S)-1-{(5R)-5-((4-carboxynaphthalen-1-yloxy)methyl)-L-prolyl}-pyrrolidine-2-carbonitrile;
(2S)-1-{(5R)-5-((5-carboxy-3-chloropyridyl-2-oxy)-methyl)-L-prolyl}-pyrrolidine-2-carbonitrile;
(2S)-1-{(5R)-5-((5-carboxy-2-bromophenoxy)-methyl)-L-prolyl}-pyrrolidine-2-carbonitrile;
(2S)-1-({(2S,5R)-5-[(2-methylphenoxy)methyl]pyrrolidin-2-yl}carbonyl)pyrrolidine-2-carbonitrile;
(2S)-1-({(2S,5R)-5-[(2-methoxyphenoxy)methyl]pyrrolidin-2-yl}carbonyl)pyrrolidine-2-carbonitrile;
(2S)-1-({(2S,5R)-5-[(2,4-dichlorophenoxy)methyl]pyrrolidin-2-yl}carbonyl)pyrrolidine-2-carbonitrile;
(2S)-1-[((2S,5R)-5-{[2-bromo-4-(trifluoromethyl)phenoxy]methyl}pyrrolidin-2-yl)carbonyl]pyrrolidine-2-carbonitrile;
(2S)-1-({(2S,5R)-5-[(4-bromo-2-methoxyphenoxy)methyl]pyrrolidin-2-yl}carbonyl)pyrrolidine-2-carbonitrile;
(2S)-1-({(2S,5R)-5-[(2-chloro-4-methoxyphenoxy)methyl]pyrrolidin-2-yl}carbonyl)pyrrolidine-2-carbonitrile;
(2S)-1-({(2S,5R)-5-[(4-bromo-2-chlorophenoxy)methyl]pyrrolidin-2-yl}carbonyl)pyrrolidine-2-carbonitrile;
(2S)-1-[((2S,5R)-5-{[(4-chloro-1-naphthyl)oxy]methyl}pyrrolidin-2-yl)carbonyl]pyrrolidine-2-carbonitrile;
(2S)-1-({(2S,5R)-5-[(quinolin-4-yloxy)methyl]pyrrolidin-2-yl}carbonyl)pyrrolidine-2-carbonitrile;
(2S)-1-({(2S,5R)-5-[(quinolin-5-yloxy)methyl]pyrrolidin-2-yl}carbonyl)pyrrolidine-2-carbonitrile;
(2S)-1-[((2S,5R)-5-{[4-bromo-2-(1H-pyrazol-3-yl)phenoxy]methyl}pyrrolidin-2-yl)carbonyl]pyrrolidine-2-carbonitrile;
(2S)-1-({(2S,5R)-5-[(2-tert-butylphenoxy)methyl]pyrrolidin-2-yl}carbonyl)pyrrolidine-2-carbonitrile;
(2S)-1-({(2S,5R)-5-[(2-tert-butyl-4-cyanophenoxy)methyl]pyrrolidin-2-yl}carbonyl)pyrrolidine-2-carbonitrile;
(2S)-1-({(2S,5R)-5-[(4-bromo-2-tert-butylphenoxy)methyl]pyrrolidin-2-yl}carbonyl)pyrrolidine-2-carbonitrile;
(2S)-1-({(2S,5R)-5-[(2-isopropylphenoxy)methyl]pyrrolidin-2-yl}carbonyl)pyrrolidine-2-carbonitrile;
ethyl 3-tert-butyl-4-[((2R,5S)-5-{[(2S)-2-cyanopyrrolidin-1-yl]carbonyl}pyrrolidin-2-yl)methoxy]benzoate;
{3-tert-butyl-4-[((2R,5S)-5-{[(2S)-2-cyanopyrrolidin--1 yl]carbonyl}pyrrolidin-2-yl)methoxy]phenoxy}acetic acid;
(2S)-1-[((2S,5R)-5-{[2-methoxy-4-(1H-tetraazol-5-yl)phenoxy]methyl}pyrrolidin-2-yl)carbonyl]pyrrolidine-2-carbonitrile;
3-tert-butyl-4-[((2R,5S)-5-{[(2S)-2-cyanopyrrolidin-1-yl]carbonyl}pyrrolidin-2-yl)methoxy]benzamide;
(2S)-1-[((2S,5R)-5-{[2-isopropyl-4-(1H-tetraazol-5-yl)phenoxy]methyl}pyrrolidin-2-yl)carbonyl]pyrrolidine-2-carbonitrile;
3-[((2R,5S)-5-{[(2S)-2-cyanopyrrolidin-1-yl]carbonyl}pyrrolidin-2-yl)methoxy]pyrrolidine-2-carboxylic acid;
(2S)-1-[((2S,5R)-5-{[4-(1-tert-butyl-1H-tetraazol-5-yl)-2-isopropylphenoxy]methyl}pyrrolidin-2-yl)carbonyl]pyrrolidine-2-carbonitrile;
(2S)-1-[((2S,5R)-5-{[4-(1-tert-butyl-1H-tetraazol-5-yl)-2-chlorophenoxy]methyl}pyrrolidin-2-yl)carbonyl]pyrrolidine-2-carbonitrile;
5-chloro-2-[((2R,5S)-5-{[(2S)-2-cyanopyrrolidin-1-yl]carbonyl}pyrrolidin-2-yl)methoxy]benzoic acid;
{2-[((2R,5S)-5-{[(2S)-2-cyanopyrrolidin-1-yl]carbonyl}pyrrolidin-2-yl)methoxy]phenyl}acetic acid;
3-[((2R,5S)-5-{[(2S)-2-cyanopyrrolidin-1-yl]carbonyl}pyrrolidin-2-yl)methoxy]-4-fluorobenzoic acid;
3-[((2R,5S)-5-{[(2S)-2-cyanopyrrolidin-1-yl]carbonyl}pyrrolidin-2-yl)methoxy]-4-isopropylbenzoic acid;
2-[((2R,5S)-5-{[(2S)-2-cyanopyrrolidin-1-yl]carbonyl}pyrrolidin-2-yl)methoxy]-1-naphthoic acid;
3-chloro-4-[((2R,5S)-5-{[(2S)-2-cyanopyrrolidin-1-yl]carbonyl}pyrrolidin-2-yl)methoxy]-N,N-dimethylbenzamide;

(2S)-1-[((2S,5R)-5-{[(2-chloro-1-oxidopyridin-3-yl)oxy]methyl}pyrrolidin-2-yl)carbonyl]pyrrolidine-2-carbonitrile;
(2S)-1-({(2S,5R)-5-[(2-chloro-4-morpholin-4-ylphenoxy)methyl]pyrrolidin-2-yl}carbonyl)pyrrolidine-2-carbonitrile;
(2S)-1-({(2S,5R)-5-[(4-amino-2-chlorophenoxy)methyl]pyrrolidin-2-yl}carbonyl)pyrrolidine-2-carbonitrile;
3-bromo-4-[((2R,5S)-5-{[(2S)-2-cyanopyrrolidin-1-yl]carbonyl}pyrrolidin-2-yl)methoxy]benzoic acid;
6-chloro-5-[((2R,5S)-5-{[(2S)-2-cyanopyrrolidin-1-yl]carbonyl}pyrrolidin-2-yl)methoxy]nicotinic acid 1-oxide;
6-[((2R,5S)-5-{[(2S)-2-cyanopyrrolidin-1-yl]carbonyl}pyrrolidin-2-yl)methoxy]-2-naphthoic acid;
(2S)-1-[((2S,5R)-5-{[2-chloro-4-(methylsulfonyl)phenoxy]methyl}pyrrolidin-2-yl)carbonyl]pyrrolidine-2-carbonitrile;
(2S)-1-[((2S,5R)-5-{[4-chloro-2-(hydroxymethyl)phenoxy]methyl}pyrrolidin-2-yl)carbonyl]pyrrolidine-2-carbonitrile;
5-chloro-6-[((2R,5S)-5-{[(2S)-2-cyanopyrrolidin-1-yl]carbonyl}pyrrolidin-2-yl)methoxy]-2-naphthoic acid;
(2S)-1-[((2S,5R)-5-{[(6-chloro-1,3-benzodioxol-5-yl)oxy]methyl}pyrrolidin-2-yl)carbonyl]pyrrolidine-2-carbonitrile;
N-{4-[((2R,5S)-5-{[(2S)-2-cyanopyrrolidin-1-yl]carbonyl}pyrrolidin-2-yl)methoxy]-1-naphthyl}methanesulfonamide;
(2S)-1-[((2S,5R)-5-{[2-bromo-4-(methylsulfonyl)phenoxy]methyl}pyrrolidin-2-yl)carbonyl]pyrrolidine-2-carbonitrile;
(2S)-1-[((2S,5R)-5-{[(6-bromo-1,3-benzodioxol-5-yl)oxy]methyl}pyrrolidin-2-yl)carbonyl]pyrrolidine-2-carbonitrile;
2-chloro-N-{3-chloro-4-[((2R,5S)-5-{[(2S)-2-cyanopyrrolidin-1-yl]carbonyl}pyrrolidin-2-yl)methoxy]phenyl}benzenesulfonamide;
N-{3-chloro-4-[((2R,5S)-5-{[(2S)-2-cyanopyrrolidin-1-yl]carbonyl}pyrrolidin-2-yl)methoxy]phenyl}methanesulfonamide;
N-{3-chloro-4-[((2R,5S)-5-{[(2S)-2-cyanopyrrolidin-1-yl]carbonyl}pyrrolidin-2-yl)methoxy]phenyl}acetamide;
(2S)-1-({(2S,5R)-5-[(1-benzothien-4-yloxy)methyl]pyrrolidin-2-yl}carbonyl)pyrrolidine-2-carbonitrile;
(2S)-1-[((2S,5R)-5-{[4-bromo-2-(methylsulfonyl)phenoxy]methyl}pyrrolidin-2-yl)carbonyl]pyrrolidine-2-carbonitrile;
N-{3-bromo-4-[((2R,5S)-5-{[(2S)-2-cyanopyrrolidin-1-yl]carbonyl}pyrrolidin-2-yl)methoxy]phenyl}acetamide;
N-{3-bromo-4-[((2R,5S)-5-{[(2S)-2-cyanopyrrolidin-1-yl]carbonyl}pyrrolidin-2-yl)methoxy]phenyl}methanesulfonamide;
N-{3-bromo-4-[((2R,5S)-5-{[(2S)-2-cyanopyrrolidin-1-yl]carbonyl}pyrrolidin-2-yl)methoxy]phenyl}benzenesulfonamide;
N-{3-bromo-4-[((2R,5S)-5-{[(2S)-2-cyanopyrrolidin-1-yl]carbonyl}pyrrolidin-2-yl)methoxy]phenyl}-2-chlorobenzenesulfonamid;
methyl 2,3-dichloro-4-[((2R,5S)-5-{[(2S)-2-cyanopyrrolidin-1-yl]carbonyl}pyrrolidin-2-yl)methoxy]benzoate;
3-[((2R,5S)-5-{[(2S)-2-cyanopyrrolidin-1-yl]carbonyl}pyrrolidin-2-yl)methoxy]-4-methoxybenzoic acid;
2,3-dichloro-4-[((2R,5S)-5-{[(2S)-2-cyanopyrrolidin-1-yl]carbonyl}pyrrolidin-2-yl)methoxy]benzoic acid;
(2S)-1-({(2S,5R)-5-[(2,4-dichloro-5-nitrophenoxy)methyl]pyrrolidin-2-yl}carbonyl)pyrrolidine-2-carbonitrile;
tert-butyl 2,3-dichloro-4-[((2R,5S)-5-{[(2S)-2-cyanopyrrolidin-1-yl]carbonyl}pyrrolidin-2-yl)methoxy]benzoate;
ethyl 4-chloro-3-[((2R,5S)-5-{[(2S)-2-cyanopyrrolidin-1-yl]carbonyl}pyrrolidin-2-yl)methoxy]benzoate;
isopropyl 4-chloro-3-[((2R,5S)-5-{[(2S)-2-cyanopyrrolidin-1-yl]carbonyl}pyrrolidin-2-yl)methoxy]benzoate;
N-{2,4-dichloro-5-[((2R,5S)-5-{[(2S)-2-cyanopyrrolidin-1-yl]carbonyl}pyrrolidin-2-yl)methoxy]phenyl}acetamide;
N-{2,4-dichloro-5-[((2R,5S)-5-{[(2S)-2-cyanopyrrolidin-1-yl]carbonyl}pyrrolidin-2-yl)methoxy]phenyl}acrylamide;
N-{2,4-dichloro-5-[((2R,5S)-5-{[(2S)-2-cyanopyrrolidin-1-yl]carbonyl}pyrrolidin-2-yl)methoxy]phenyl}benzamide;
N-{2,4-dichloro-5-[((2R,5S)-5-{[(2S)-2-cyanopyrrolidin-1-yl]carbonyl}pyrrolidin-2-yl)methoxy]phenyl}-2-methoxyacetamide;
N-{2,4-dichloro-5-[((2R,5S)-5-{[(2S)-2-cyanopyrrolidin-1-yl]carbonyl}pyrrolidin-2-yl)methoxy]phenyl}-2-(2-methoxyethoxy)acetamide;
N-{2,4-dichloro-5-[((2R,5S)-5-{[(2S)-2-cyanopyrrolidin-1-yl]carbonyl}pyrrolidin-2-yl)methoxy]phenyl}cyclopropanecarboxamide;
ethyl 2,4-dichloro-5-[((2R,5S)-5-{[(2S)-2-cyanopyrrolidin-1-yl]carbonyl}pyrrolidin-2-yl)methoxy]phenylcarbamate;
bis-[N-{2,4-dichloro-5-[((2R,5S)-5-{[(2S)-2-cyanopyrrolidin-1-yl]carbonyl}pyrrolidin-2-yl)methoxy]phenyl}]methanesulfonamide;
N-{2,4-dichloro-5-[((2R,5S)-5-{[(2S)-2-cyanopyrrolidin-1-yl]carbonyl}pyrrolidin-2-yl)methoxy]phenyl)}-1-phenylmethanesulfonamide;
N-{2,4-dichloro-5-[((2R,5S)-5-{[(2S)-2-cyanopyrrolidin-1-yl]carbonyl}pyrrolidin-2-yl)methoxy]phenyl}-N'-phenylurea;
N-{2,4-dichloro-5-[((2R,5S)-5-{[(2S)-2-cyanopyrrolidin-1-yl]carbonyl}pyrrolidin-2-yl)methoxy]phenyl}-N'-(3,5-dimethoxyphenyl)urea;
N-{2,4-dichloro-5-[((2R,5S)-5-{[(2S)-2-cyanopyrrolidin-1-yl]carbonyl}pyrrolidin-2-yl)methoxy]phenyl}-N'-(4-nitrophenyl)urea;
(2S)-1-({(2S,5R)-5-[(5-amino-2,4-dichlorophenoxy)methyl]pyrrolidin-2-yl}carbonyl)pyrrolidine-2-carbonitrile;
isopropyl 6-chloro-5-[((2R,5S)-5-{[(2S)-2-cyanopyrrolidin-1-yl]carbonyl}pyrrolidin-2-yl)methoxy]nicotinate;
(2S)-1-[((2S,5R)-5-{[2-chloro-3-(methylsulfonyl)phenoxy]methyl}pyrrolidin-2-yl)carbonyl]pyrrolidine-2-carbonitrile;
ethyl 3-[((2R,5S)-5-{[(2S)-2-cyanopyrrolidin-1-yl]carbonyl}pyrrolidin-2-yl)methoxy]-4,5-difluorobenzoate;
3-[((2R,5S)-5-{[(2S)-2-cyanopyrrolidin-1-yl]carbonyl}pyrrolidin-2-yl)methoxy]-4,5-difluorobenzoic acid; and
tert-butyl 3-[((2R,5S)-5-{[(2S)-2-cyanopyrrolidin-1-yl]carbonyl}pyrrolidin-2-yl)methoxy]-4,5-difluorobenzoate.

\* \* \* \* \*

UNITED STATES PATENT AND TRADEMARK OFFICE
CERTIFICATE OF CORRECTION

PATENT NO. : 7,205,409 B2  
APPLICATION NO. : 10/935053  
DATED : April 17, 2007  
INVENTOR(S) : Zhonghua Pei et al.

It is certified that error appears in the above-identified patent and that said Letters Patent is hereby corrected as shown below:

Column 33, line 44, "Alzheimer's Disease" to read as --Alzheimer's disease--

Column 33, line 48 to 51, Delete: "DEFINITIONS As used throughout this specification and the appended claims, the following terms have the following meanings:"

Column 36, line 55, "group, as definedherein." to read as --group, as defined herein.--

Column 39, line 22, "an carbonyl group" to read as --a carbonyl group--

Column 43, line 20, "0.3 ug/mL" to be read as --0.3μg/mL--

Column 49, line 22, "important fuctions" to read as --important functions--

Column 49, line 27, "stimulationwith" to read as --stimulation with--

Column 49, line 32, "costimulatorymolecule CD86" to read as --costimulatory molecule CD86--

Column 50, line 31, "Alzheimer's Disease" to read as --Alzheimer's disease--

Column 62, line 25, "MS (ESI) nl/z 170 (M+Ht.)" to read as --MS (ESI) m/z 170 (M+Ht.)--

Column 62, line 63, "concentratedin vacuo" to read as --concentrated in vacuo--

Column 63, line 16, "was trigered" to read as --was triggered--

Column 63, line 51, "(2S)-4,4-difluoro-1-((5!)-5-methyl-L- prolyl)pyrrolidine-2-carbonitrile" to read as --(2S)-4,4-difluoro-1-((5S)-5-methyl-L- prolyl)pyrrolidine-2-carbonitrile--

Column 69, line 26 and 27, "(6.9 g, 27.2 mmol) was was dissolved" to read as --(6.9 g, 27.2 mmol) was dissolved--

Signed and Sealed this

Nineteenth Day of October, 2010

David J. Kappos  
*Director of the United States Patent and Trademark Office*

Column 82, line 40, "carbonitril" to read as --carbonitrile--

Column 84, line 61, "The Boc group was removed using precedure as described" to read as --The Boc group was removed using procedure as described--

Column 90, line 31, "was hydgrogenated" to read as --was hydrogenated--

Column 93, line 23, "The mixture was filted" to read as --The mixture was filtered--

Column 100, line 63, "stirred for 1 hour and lo concentrated in vacuo" to read as --stirred for 1 hour and concentrated in vacuo--

Column 110, line 31, "for overnight." to read as --overnight.--